(12) United States Patent
Wood et al.

(10) Patent No.: US 7,105,328 B2
(45) Date of Patent: Sep. 12, 2006

(54) METHODS FOR SCREENING FOR COMPOUNDS THAT MODULATE PD-1 SIGNALING

(75) Inventors: Clive Wood, Boston, MA (US); Gordon J. Freeman, Brookline, MA (US); Divya Chaudhary, Andover, MA (US)

(73) Assignees: Dana-Farber Cancer Institute, Boston, MA (US); Wyeth, Madison, NJ (US)

( * ) Notice: Subject to any disclaimer, the term of this patent is extended or adjusted under 35 U.S.C. 154(b) by 314 days.

(21) Appl. No.: 10/115,615

(22) Filed: Apr. 2, 2002

(65) Prior Publication Data

US 2003/0044768 A1    Mar. 6, 2003

Related U.S. Application Data

(60) Provisional application No. 60/281,064, filed on Apr. 2, 2001.

(51) Int. Cl.
*C12N 9/12* (2006.01)
*G01N 33/567* (2006.01)

(52) U.S. Cl. ...................... 435/194; 435/7.21
(58) Field of Classification Search ............... 435/7.21, 435/194
See application file for complete search history.

(56) References Cited

U.S. PATENT DOCUMENTS 6,040,152 A    3/2000   Kupfer et al.

6,576,236 B1 *  6/2003   Boussiotis et al. ......... 424/154.1

OTHER PUBLICATIONS

Kurita-Ochiai et al., Journal of Immunology, 2003, vol. 171, pp. 3576-3584.*

Latchman et al., Nature Immunology, Mar. 2001, vol. 2, pp. 261-268.*

Adachi, T., et al. "CD72 negatively regulates signaling through the antigen receptor of B cells." *J Immunol.* Feb. 1, 2000, 164(3):1223-9.

Freeman, G.J., et al. "Engagement of the PD-1 immunoinhibitory receptor by a novel B7 family member leads to negative regulation of lymphocyte activation." *J Exp Med.* Oct. 2, 2000, 192(7):1027-34.

Liu, Y., et al. "Phosphorylation of the protein kinase C-theta activation loop and hydrophobic motif regulates its kinase activity, but only activation loop phosphorylation is critical to *in vivo* nuclear-factor-κB induction." *Biochem J.* Jan. 15, 2002, 361:255-65.

* cited by examiner

*Primary Examiner*—Phillip Gambel
*Assistant Examiner*—Ilia Ouspenski
(74) *Attorney, Agent, or Firm*—Foley Hoag, LLP

(57) ABSTRACT

Disclosed are screening assays for identifying compounds which modulate the activity of, or signaling via, B7-4, or PD-1, especially which modulate the binding of B7-4 or PD-1 to a target molecule Further disclosed are a vaccine and also other compositions which contain agents that modulate signaling via PD-1.

6 Claims, 41 Drawing Sheets

FIG. 1

GCTTCCCGAGGCTCCGCACCAGCCGGCGGCTTCTGTCCGCCTGCAGGGCATTCCA
GAAAGATGAGGATATTTGCTGTCTCTTTATATTCATGACCTACTGGCATTGCTG
AACGCATTACTGTCACGGTTCCCAAGGACCTATATGTGGTAGAGTATGGTA
GCAATATGACAATTGAATGCAAATTCCCAGTAGAAAACAATTAGACCTGGC
TGCACTAATTGTCTATTGGGAAATGGAGGATAAGAACATTATTCAATTTGTGC
ATGGAGAGGAAGACCTGAAGGTTCAGCATAGTAGCTACAGACAGAGGCCC
GGCTGTTGAAGGACCAGCTCTCCCTGGGAAATGCTGCACTTCAGATCACAGA
TGTGAAATTGCAGGATGCAGGGGTGTACCGCTGCATGATCAGCTATGGTGGT
GCCGACTACAAGCGAATTACTGTGAAAGTCACAACAACAAATCA
ACCAAAGAATTTGGTTGTGGATCCAGTCACCTCTGAACATGAACTGACATGT
CAGGCTGAGGGCTACCCCCAAGGCCGAAGTCATCTGGACAAGCAGTGACCATC
AAGTCCTGAGTGGTAAGACCACCACCACTGAGAATCAACACAACAACTAATGAGATTT
TTTCAATGTGCACTTTTAGGAGATTAGATCCTGAGGAAAACCATACAGCTGAATTG
CTACTGCACTTTAGGAGATTAGATCCTGAGGAAAACCATACAGCTGAATTG
GTCATCCCAGGTAATATTCTGAATGTCCATTAAATATGTCTAACACTGTC
CCCTAGCACCTAGCATGATGTCTGCCTATCATAGTCATTCAGTGATTGTTGAA
TAAATGAATGAATAACACTATGTTACAAATATATCCTAATTCCTCAC
CTCCATTCATCCAAACCATATTGTTACTTAATAAACATTCAGCAGATATTTAT
GGAATAAAAAAAAAAAAAAAAA

FIG. 2

```
CGAGGCTCCGCACCAGCCGCGCTTCTGTCCGCCTGCAGGGCATTCCAGAAAGA
TGAGGATATTTGCTGTCTTTATATTCATGACCTACTGGCATTTGCTGAACGCATT
TACTGTCACGGTTCCCAAGGACCTATATGTGGTAGAGTATGGTAGCAATATGAC
AATTGAATGCAAATTCCCAGTAGAAAACAATTAGACCTGGCTGCACTAATTGT
CTATTGGGAAATGGAGGATAAGAACATTATTCAATTTGTGCATGGAGAGGAAG
ACCTGAAGGTTCAGCATAGTAGCTACAGACAGAGGGCCCGGCTGTTGAAGGAC
CAGCTCTCCTGGGAAATGCTGCACTTCAGATCACAGATGTGAAATTGCAGGAT
GCAGGGGTGTACCGCTGCATGATCAGCTATGGTGGTGCCGACTACAAGCGAAT
TACTGTGAAAGTCAATGCCCCATACAACAAAATCAACCAAAGAATTTTGGTTGT
GGATCCAGTCACCTCTGAACATGAACTGACATGTCAGGCTGAGGGCTACCCCA
AGGCCGAAGTCATCTGGACAAGCAGTGACCATCAAGTCCTGAGTGGTAAGACC
ACCACCACCAATTCCAAGAGAGAGGAGAAGCTTTTCAATGTGACCAGCACACT
GAGAATCAACACAACAACTAATGAGATTTTCTACTGCACTTTTAGGAGATTAGA
TCCTGAGGAAAACCATACAGCTGAATTGGTCATCCCAGAACTACCTCTGGCACA
TCCTCCAAATGAAAGGACTCACTTGGTAATTCTGGGAGCCATCTTATTATGCCTT
GGTGTAGCACTGACATTCATCTTCCGTTTAAGAAAAGGGAGAATGATGGATGT
GAAAAAATGTGGCATCCAAGATACAAACTCAAAGAAGCAAAGTGATACACATTT
GGAGGAGACGTAATCCAGCATTGGAACTTCTGATCTTCAAGCAGGGATTCTCA
ACCTGTGGTTTAGGGGTTCATCGGGGCTGAGCGTGACAAGAGGAAGGAATGG
GCCCGTGGGATGCAGGCAATGTGGGACTTAAAAGGCCCAAGCACTGAAAATG
GAACCTGGCGAAAGCAGAGGAGGAGAATGAAGAAAGATGGAGTCAAACAGGG
AGCCTGGAGGGAGACCTTGATACTTTCAAATGCCTGAGGGGCTCATCGACGCC
TGTGACAGGGAGAAAGGATACTTCTGAACAAGGAGCCTCCAAGCAAATCATCC
ATTGCTCATCCTAGGAAGACGGGTTGAGAATCCCTAATTTGAGGGTCAGTTCCT
GCAGAAGTGCCCTTTGCCTCCACTCAATGCCTCAATTTGTTTTCTGCATGACTGA
GAGTCTCAGTGTTGGAACGGGACAGTATTTATGTATGAGTTTTTCCTATTTATTT
TGAGTCTGTGAGGTCTTCTTGTCATGTGAGTGTGGTTGTGAATGATTTCTTTTGA
AGATATATTGTAGTAGATGTTACAATTTTGTCGCCAAACTAAACTTGCTGCTTAA
TGATTTGCTCACATCTAGTAAAACATGGAGTATTTGTAAAAAAAAAAAAAAA
```

FIG. 3

292 secreted (245 amino acids)

Signal/IgV/IgC/hydrophilic tail
  (a)    (b)   (c)      (d)

Ig cysteines in large bold

MRIFAVFIFMTYWHLLNA (signal)

FTVTVPKDLYVVEYGSNMTIECKFPVEKQLDLAALIVYWEMEDKN
IIQFVHGEEDLKVQHSSYRQRARLLKDQLSLGNAALQITDVKLQD
AGVYRCMISYGGADYKRITVKVNAPY (IgV)

NKINQRILVVDPVTSEHELTCQAEGYPKAEVIWTSSDHQVLSGKT
TTTNSKREEKLFNVTSTLRINTTTNEIFYCTFRRLDPEENHTAEL
VIP (IgC)

GNILNVSIKICLTLSPST (hydrophilic tail)

FIG. 4

292 membrane   (290 amino acids)

Signal/IgV/IgC/transmembrane (underlined) plus cytoplasmic

Ig cysteines in large bold

MRIFAVFIFMTYWHLLNA   (signal)

FTVTVPKDLYVVEYGSNMTIECKFPVEKQLDLAALIVYWEMEDKN
IIQFVHGEEDLKVQHSSYRQRARLLKDQLSLGNAALQITDVKLQD
AGVYRCMISYGGADYKRITVKVNAPY   (IgV)

NKINQRILVVD PVTSEHELTCQAEGYPKAEVIWTSSDHQVLSGKT
TTTNSKREEKLFNVTSTLRINTTTNEIFYCTFRRLDPEENHTAEL
VIP   (IgC)

ELPLAHPPNER<u>THLVILGAILLCLGVALTFIFR</u>LRKGRMMDVKKC
GIQDTNSKKQSDTHLEET   (transmembrane plus cytoplasmic)

FIG. 5A

AGATAGTTCCCAAAACATGAGGATATTTGCTGGCATTATATTCACAGCCTGC
TGTCACTTGCTACGGGCGTTTACTATCACGGCTCCAAAGGACTTGTACGTG
GTGGAGTATGGCAGCAACGTCACGATGGAGTGCAGATTCCCTGTAGAACG
GGAGCTGGACCTGCTTGCGTTAGTGGTGTACTGGGAAAAGGAAGATGAGC
AAGTGATTCAGTTTGTGGCAGGAGAGGAGGACCTTAAGCCTCAGCACAGCA
ACTTCAGGGGGAGAGCCTCGCTGCCAAAGGACCAGCTTTTGAAGGGAAAT
GCTGCCCTTCAGATCACAGACGTCAAGCTGCAGGACGCAGGCGTTTACTGC
TGCATAATCAGCTACGGTGGTGCGGACTACAAGCGAATCACGCTGAAAGTC
AATGCCCCATACCGCAAAATCAACCAGAGAATTTCCGTGGATCCAGCCACTT
CTGAGCATGAACTAATATGTCAGGCCGAGGGTTATCCAGAAGCTGAGGTAA
TCTGGACAAACAGTGACCACCAACCCGTGAGTGGGAAGAGAAGTGTCACCA
CTTCCCGGACAGAGGGGATGCTTCTCAATGTGACCAGCAGTCTGAGGGTCA
ACGCCACAGCGAATGATGTTTTCTACTGTACGTTTGGAGATCACAGCCAG
GGCAAAACCACACAGCGGAGCTGATCATCCCAGAACTGCCTGCAACACATC
CTCCACAGAACAGGACTCACTGGGTGCTTCTGGGATCCATCCTGTTGTTCC
TCATTGTAGTGTCCACGGTCCTCCTCTTCTTGAGAAAACAAGTGAGAATGCT
AGATGTGGAGAAATGTGGCGTTGAAGATACAAGCTCAAAAAACCGAAATGA
TACACAATTCGAGGAGACGTAAGCAGTGTTGAACCCTCTGATCGTCGATTG
GCAGCTTGTGGTCTGTGAAAGAAAGGGCCCATGGGACATGAGTCCAAAGAC
TCAAGATGGAACCTGAGGGAGAGAACCAAGAAAGTGTTGGGAGAGGAGCC
TGGAACAACGGACATTTTTTCCAGGGAGACACTGCTAAGCAAGTTGCCCAT
CAGTCGTCTTGGGAAATGGATTGAGGGTTCCTGGCTTAGCAGCTGGTCCTT
GCACAGTGACCTTTTCCTCTGCTCAGTGCCGGGATGAGAGATGGAGTCATG
AGTGTTGAAGAATAAGTGCCTTCTATTTATTTTGAGTCTGTGTGTTCTACTT
TGGGCATGTAATTATGACTGGTGAATTCTGACGACATGATAGATCTTAAGAT
GTAGTCACCAAACTCAACTGCTGCTTAGCATCCTCCGTAACTACTGATACAA
GCAGGGAACACAGAGGTCACCTGCTTGGTTTGACAGGCTCTTGCTGTCTGA
CTCAAATAATCTTTATTTTTCAGTCCTCAAGGCTCTTCGATAGCAGTTGTTCT
GTATCAGCCTTATAGGTGTCAGGTATAGCACTCAACATCTCATCTCATTACA
ATAGCAACCCTCATCACCATAGCAACAGCTAACCTCTGTTATCCTCACTTCA
TAGCCAGGAAGCTGAGCGACTAAGTCACTTGCCCACAGAGTATCAGCTCTC
AGATTTCTGTTCTTCAGCCACTGTCCTTTCAGGATAGAATTTGTCGTTAAGAA
ATTAATTTAAAAACTGATTATTGAGTAGCATTGTATATCAATCACAACATGCC
TTGTGCACTGTGCTGGCCTCTGAGCATAAAGATGTACGCCGGAGTACCGGT
CGGACATGTTTATGTGTGTTAAATACTCAGAGAAATGTTCATTAACAAGGAG
CTTGCATTTTAGAGACACTGGAAAGTAACTCCAGTTCATTGTCTAGCATTAC
ATTTACCTCATTTGCTATCCTTGCCATACAGTCTCTTGTTCTCCATGAAGTGT
CATGAATCTTGTTGAATAGTTCTTTTATTTTTTAAATGTTTCTATTTAAATGATA
TTGACATCTGAGGCGATAGCTCAGTTGGTAAAACCCTTTCCTCACAAGTGTG
AAACCCTGAGTCTTATCCCTAGAACCCACATAAAAAACAGTTGCGTATGTTT
GTGCATGCTTTTGATCCCAGCACTAGGGAGGCAGAGGCAGGCAGATCCTG
AGCTCTCATTGACCACCCAGCCTAGCCTACATGGTTAGCTCCAGGCCTACA
GGAGCTGGCAGAGCCTGAAAAACGATGCCTAGACACACACACACACACACA
CACACACACACACACACACACACCATGTACTCATAGACCTAAGTGCACC
CTCCTACACATGCACACACATACAATTCAAACACAAATCAACAGGGAATTGT

FIG. 5B

CTCAGAATGGTCCCCAAGACAAAGAAGAAGAAAAACACCAAACCAGCTCTA
TTCCCTCAGCCTATCCTCTCTACTCCTTCCTAGAAGCAACTACTATTGTTTTT
GTATATAAATTTACCCAACGACAGTTAATATGTAGAATATATATTAAAGTGTC
TGTCAATATATATTATCTCTTTCTTTCTTTCTTCCTTTCTTTCTTTCTTTCTTTC
TTTCTTTCTTTCTTTCTTTCTTTCTTTCTTTCTTCCTTCCTTCCTTCCTTCCTTC
CTTCCTTCCTTCCTTTCTTTCTTTCTTTCTTTTTTTCTGTCTATCTGTACCTAAA
TGGTTGCTCACTATGCATTTTCTGTGCTCTTCGCCCTTTTTATTTAATGTATG
GATATTTATGCTGCTTCCAGAATGGATCTAAAGCTCTTTGTTTCTAGGTTTTC
TCCCCCATCCTTCTAGGCATCTCTCACACTGTCTAGGCCAGACACCATGTCT
GCTGCCTGAATCTGTAGACACCATTTATAAAGCACGTACTCACCGAGTTTGT
ATTTGGCTTGTTCTGTGTCTGATTAAAGGGAGACCATGAGTCCCCAGGGTA
CACTGAGTTACCCCAGTACCAAGGGGGAGCCTTGTTTGTGTCTCCATGGCA
GAAGCAGGCCTGGAGCCATTTTGGTTTCTTCCTTGACTTCTCTCAAACACAG
ACGCCTCACTTGCTCATTACAGGTTCTCCTTTGGGAATGTCAGCATTGCTCC
TTGACTGCTGGCTGCCCTGGAAGGAGCCCATTAGCTCTGTGTGAGCCCTTG
ACAGCTACTGCCTCTCCTTACCACAGGGGCCTCTAAGATACTGTTACCTAGA
GGTCTTGAGGATCTGTGTTCTCTGGGGGGAGGAAAGGAGGAGGAACCCAG
AACTTTCTTACAGTTTTCCTTGTTCTGTCACATGTCAAGACTGAAGGAACAG
GCTGGGCTACGTAGTGAGATCCTGTCTCAAAGGAAAGACGAGCATAGCCGA
ACCCCCGGTGGAACCCCTCTGTTACCTGTTCACACAAGCTTATTGATGAGT
CTCATGTTAATGTCTTGTTTGTATGAAGTTTAAGAAAATATCGGGTTGGGCAA
CACATTCTATTTATTCATTTTATTTGAAATCTTAATGCCATCTCATGGTGTTGG
ATTGGTGTGGCACTTTATTCTTTTGTGTTGTGTATAACCATAAATTTTATTTTG
CATCAGATTGTCAATGTATTGCATTAATTTAATAAATATTTTTATTTATTAAAAA
AAAAAAAAAAAAAAA

FIG. 6

MRIFAGIIFTACCHLLRAFTITAPKDLYVVEYGSNVTMECRFPVERELDLLALVVYWEKEDEQVIQFVAGEE
DLKPQHSNFRGRASLPKDQLLKGNAALQITDVKLQDAGVYCCIISYGGADYKRITLKVNAPYRKINQRISV
DPATSEHELICQAEGYPEAEVIWTNSDHQPVSGKRSVTTSRTEGMLLNVTSSLRVNATANDVFYCTFWR
SQPGQNHTAELIIPELPATHPPQNRTHWVLLGSILLFLIVVSTVLLFLRKQVRMLDVEKCGVEDTSSKNRN
DTQFEET

FIG. 7 mB7-4 vs. hB7-4

69% identity

```
mB7-4   1   MRIFAGIIFTACCHLLRAFTITAPKDLYVVEYGSNVTMECRFPVERELDLLALVVYWEKE  60
            MRIFA  IF    HLL  AFT+T PKDLYVVEYGSN+T+EC+FPVE++LDL AL+VYWE E
hB7-4   1   MRIFAVFIFMTYWHLLNAFTVTVPKDLYVVEYGSNMTIECKFPVEKQLDLAALIVYWEME  60 mB7-4  61   DEQVIQFVAGEEDLKPQHSNFRGRASLPKDQLLKGNAALQITDVKLQDAGVYCCIISYGG  120
            D+ +IQFV GEEDLK  QHS++R RA L KDQL  GNAALQITDVKLQDAGVY C+ISYGG
hB7-4  61   DKNIIQFVHGEEDLKVQHSSYRQRARLLKDQLSLGNAALQITDVKLQDAGVYRCMISYGG  120 mB7-4 121   ADYKRITLKVNAPYRKINQRI-SVDPATSEHELICQAEGYPEAEVIWTNSDHQPVSGKRS  179
            ADYKRIT+KVNAPY KINQRI  VDP TSEHEL CQAEGYP+AEVIWT+SDHQ +SGK +
hB7-4 121   ADYKRITVKVNAPYNKINQRILVVDPVTSEHELTCQAEGYPKAEVIWTSSDHQVLSGKTT  180 mB7-4 180   VTTSRTEGMLLNVTSSLRVNATANDVFYCTFWRSQPGQNHTAELIIPELPATHPPQNRTH  239
            T S+ E  L NVTS+LR+N T N++FYCTF R  P +NHTAEL+IPELP  HPP  RTH
hB7-4 181   TTNSKREEKLFNVTSTLRINTTTNEIFYCTFRRLDPEENHTAELVIPELPLAHPPNERTH  240 mB7-4 240   WVLLGSILLFLIVVSTVLLFLRKQVRMLDVEKCGVEDTSSKNRNDTQFEET  290
            V+LG+ILL  L V  T +  LRK   RM+DV+KCG++DT+SK ++DT  EET
hB7-4 241   LVILGAILLCLGVALTFIFRLRKG-RMMDVKKCGIQDTNSKKQSDTHLEET  290
```

FIG. 9
IgG
mICOS-his
Vector
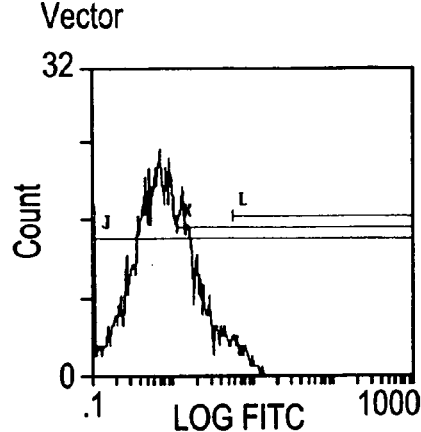
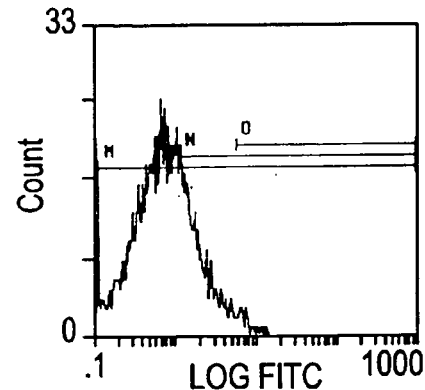
B7-1
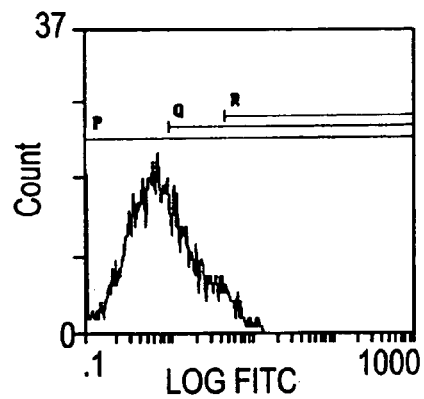
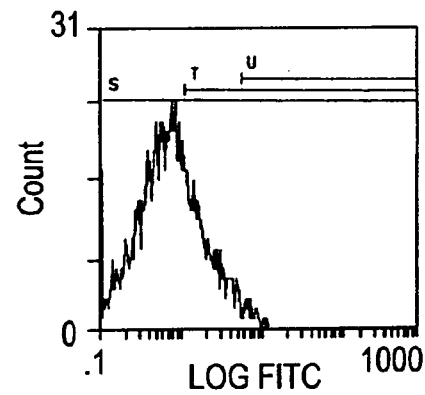
292
B7-4
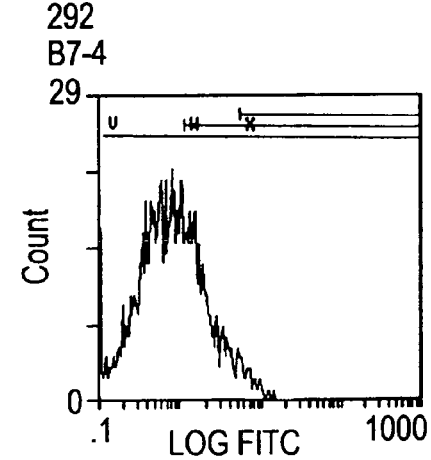
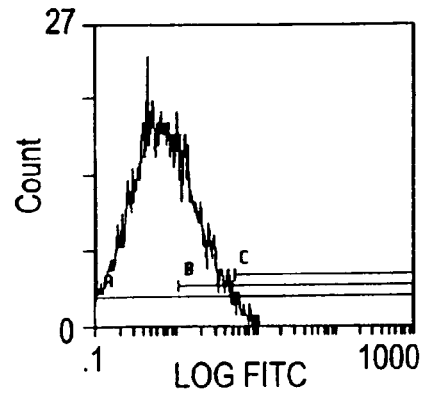

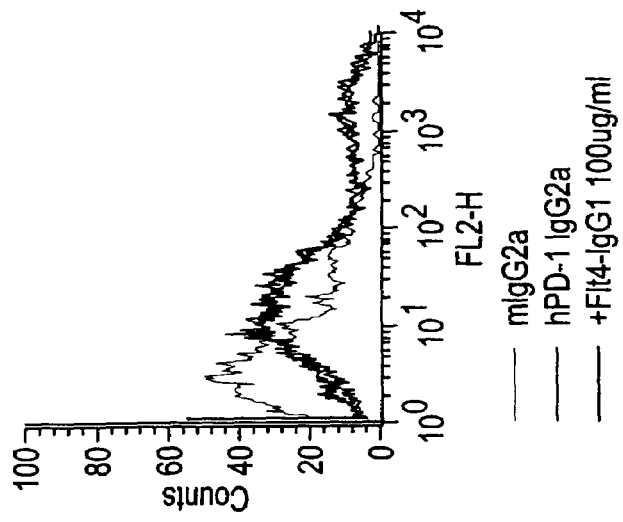
FIG. 14D  FIG. 14E  FIG. 14F
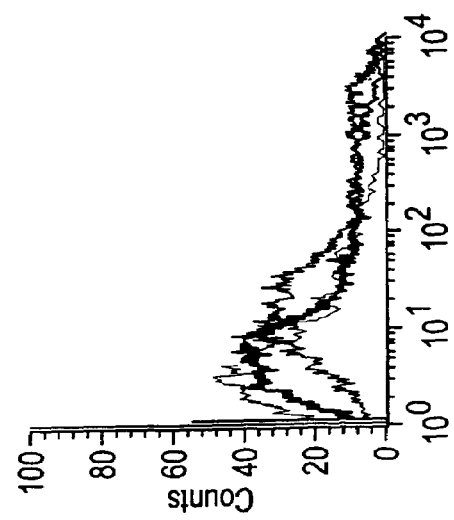

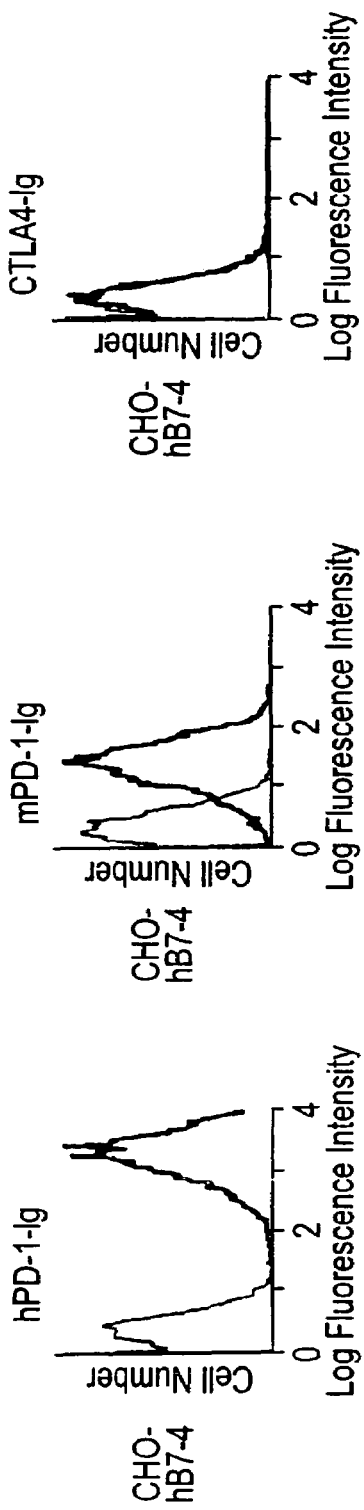
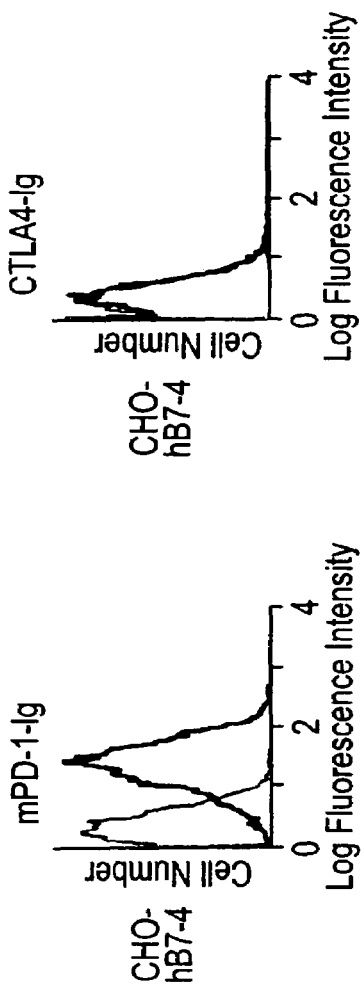
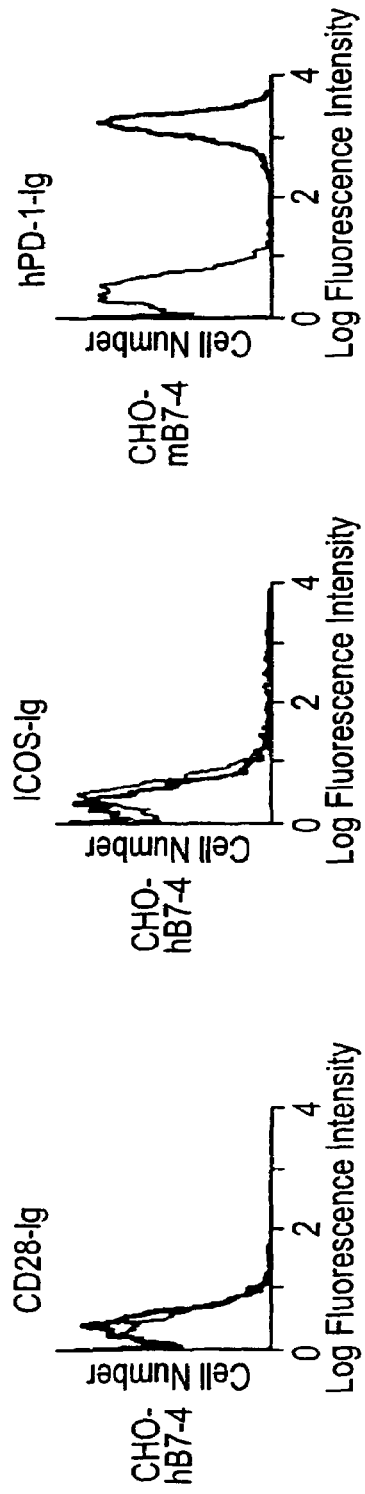
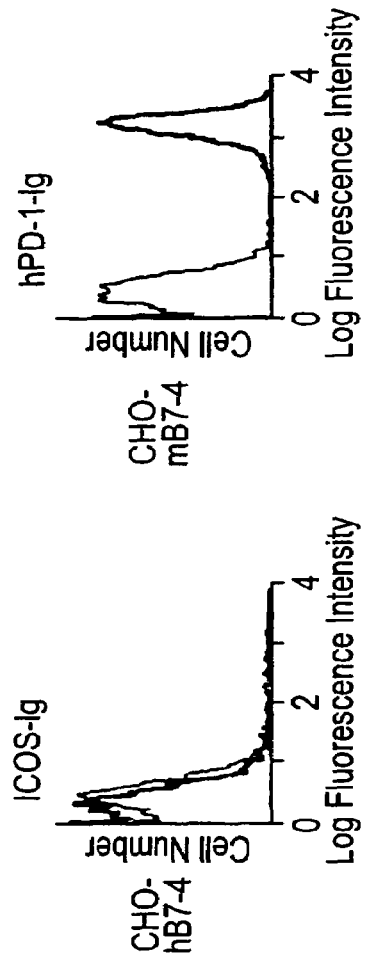
FIG. 15A, FIG. 15B, FIG. 15C, FIG. 15D, FIG. 15E, FIG. 15F B7-4-COS Inhibits IL-2 Production by Jurkats

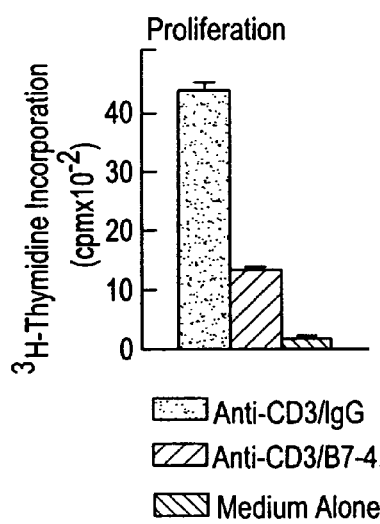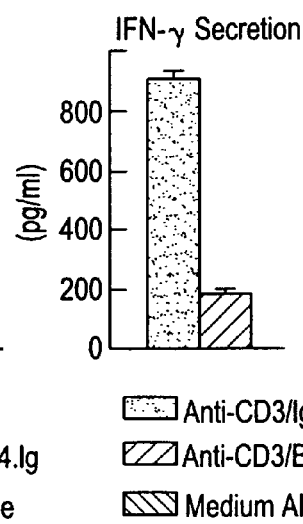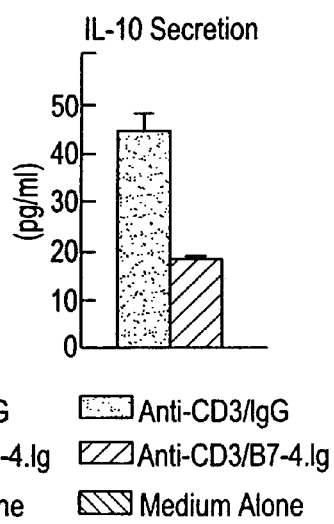

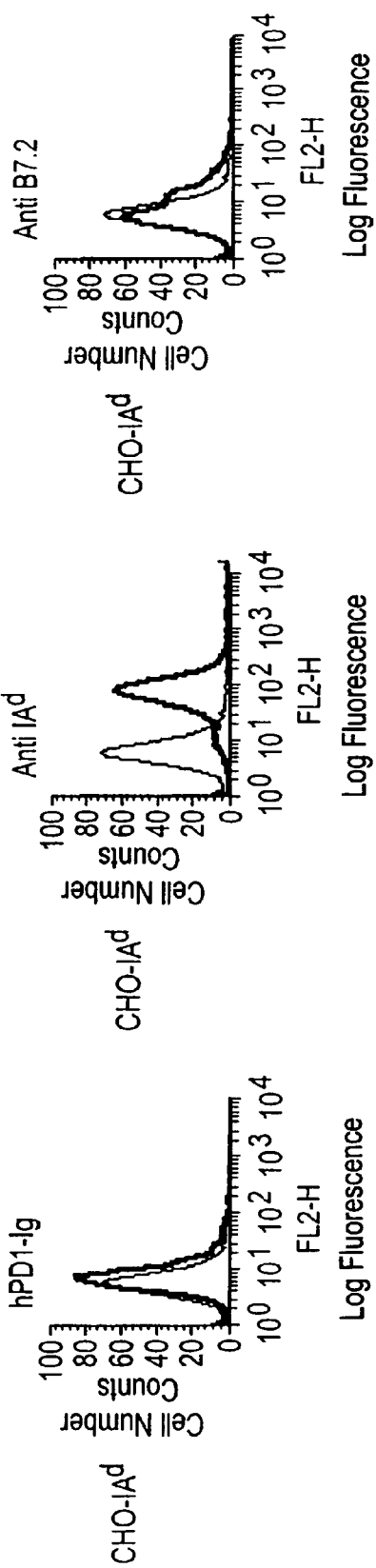

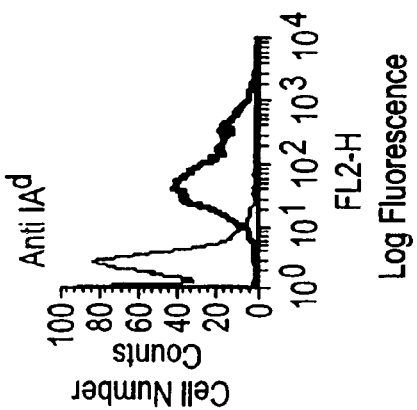
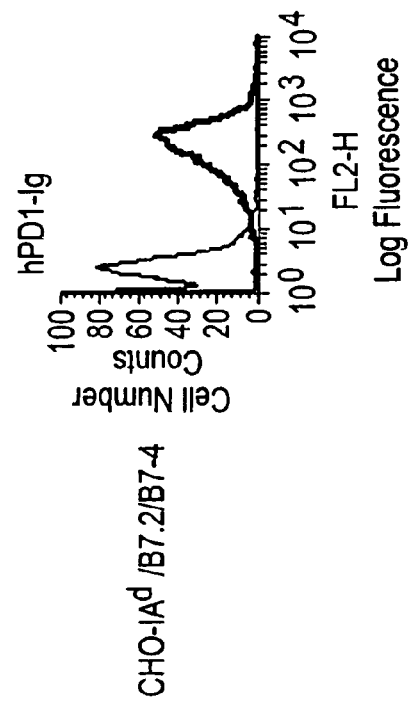
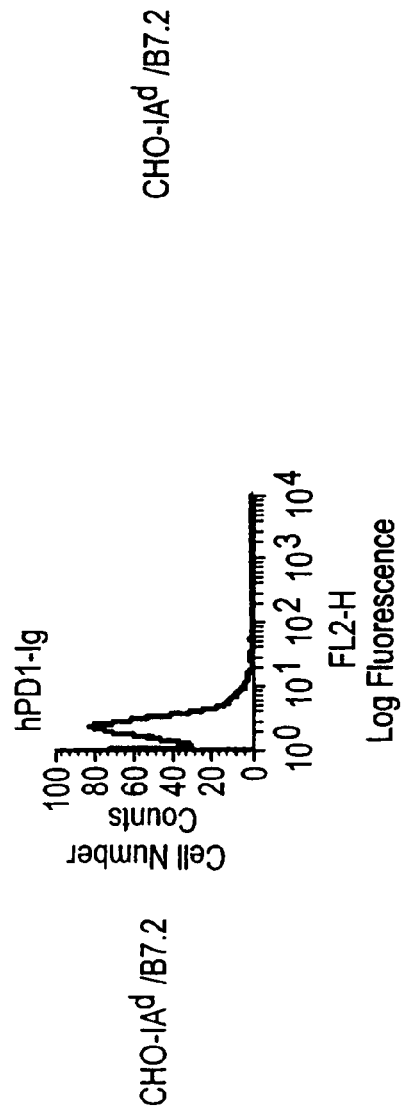
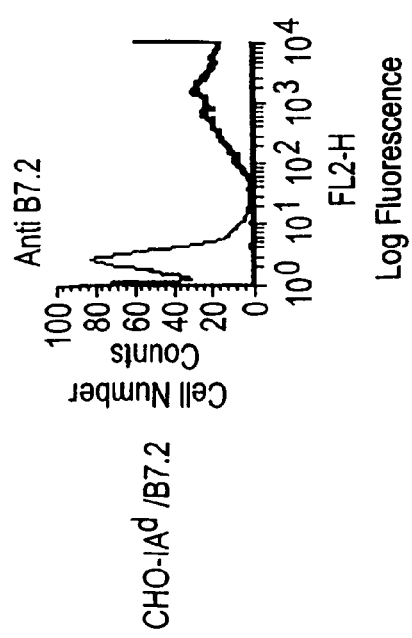

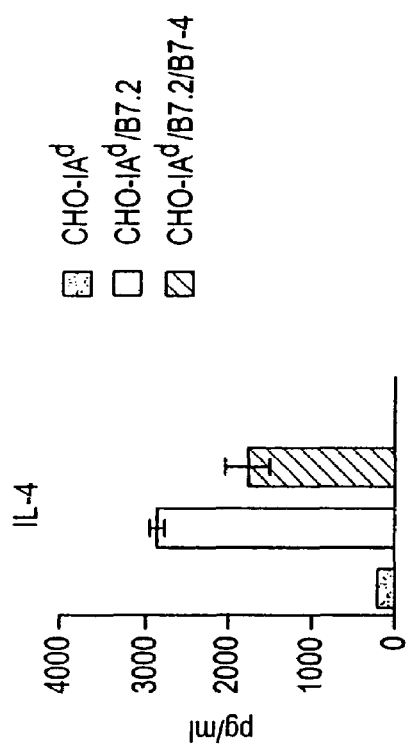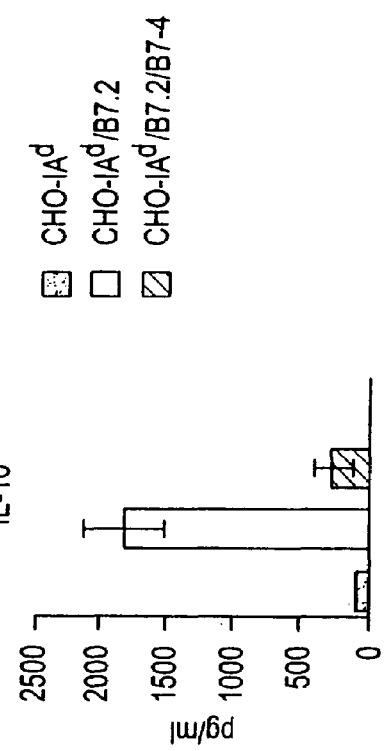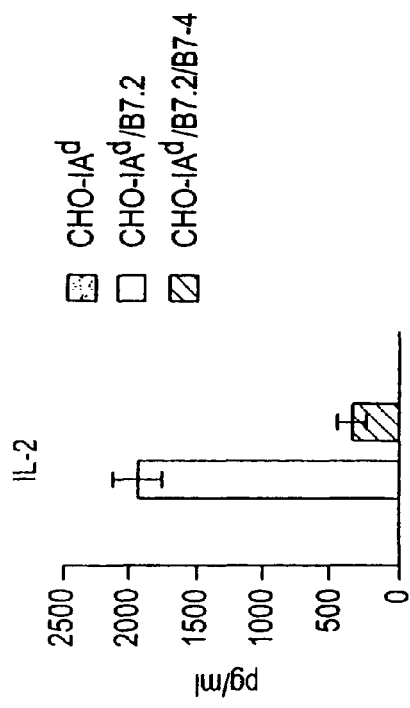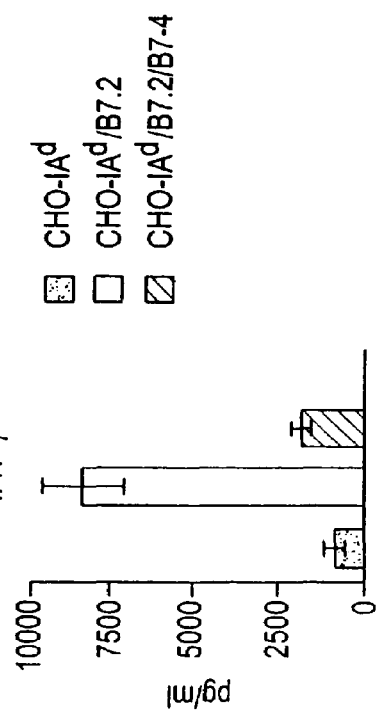

CHO-IA$^d$

CHO-IA$^d$/B7.2

CHO-IA$^d$/B7.2/B7-4

Inhibition of B7-4 binding by PD-1 clone 17

Fig. 31B

```
hPD-1  LVVGVVGGLLG. .SLVLLLVWVL AVICSRAARG TIGARRTGQP
mPD-1  MVIGIMSALVGI PVLLLLAWAL AVFCSTSMSE ARGAGSKDDT
                                                    Y        Y(p)
                                                    ────     ────
                                                    F        Y(p)
                                                             ────
                                                             F hPD-1  LKEDPSAVPV FSVDYGEL DF QWREKTPEPP VPCVPEQTEY
                  ────    ──────        ──────    ──────
mPD-1  LKEEPSAAPV PSVAYEEL DF QGREKTPELP TACV..HTEY hPD-1  ATIVFPSGMG TSSPARRGSA DGPRSAQPLR PEDGHCSWPL
       ──────                                     ──────
mPD-1  ATIVFTEGLG ASAMGRRGSA DGLQGPRPPR HEDGHCSWPL
```

ITIM Peptides
PD-1_pY1    biotin- KEDPSAVPVFSVDY(PO4)GELDFQWRE-amide
PD-1_Y1F    biotin- KEDPSAVPVFSVDFGELDFQWRE-amide
PD-1_Y1     biotin- KEDPSAVPVFSVDYGELDFQWRE-amide
PD-1_pY2    biotin- KTPEPPVPSVPEQTEY(PO4)ATIVFPSGMGTSS-amide
PD-1_Y2F    biotin- KTPEPPVPSVPEQTEFATIVFPSGMGTSS-amide
PD-1_Y2     biotin- KTPEPPVPSVPEQTEYATIVFPSGMGTSS-amide Other Peptides
PD-1_K212   biotin-RGTIGARRTGQP LKEDPSAVPVFS
PD-1_K212D  biotin-RGTIGARRTGQP LDEDPSAVPVFS
PD-1_K335   biotin-DFQWREKTPEPP VPCVPEQ
PD-1_K335D  biotin-DFQWREDTPEPP VPCVPEQ
PD-1_Ctail1 biotin-VFPSGMGTSSPARRGSADGPRSA
PD-1_Ctail2 biotin-ARRGSADGPRSAQPLRPEDGHCSWPL

METHODS FOR SCREENING FOR COMPOUNDS THAT MODULATE PD-1 SIGNALING

RELATED APPLICATIONS

This claims priority to U.S. Ser. No. 60/281,064 filed on Apr. 2, 2001. This application is incorporated herein in its entirety by this reference.

GOVERNMENT FUNDING

Work described herein was supported under AI 39671, AI 44690, CA 84500 and AI 41584 awarded by the National Institutes of Health. The U.S. government, therefore, may have certain rights in this invention.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165:302–319; Mueller, D. L. et al. (1990) *J. Immunol.* 144:3701–3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC restricted and is thought to be provided by one or more distinct cell surface molecules expressed by APCs (Jenkins, M. K. et al. (1988) *J. Immunol.* 140:3324–3330; Linsley, P. S. et al. (1991) *J. Exp. Med.* 173:721–730; Gimmi, C. D. et al. 1991 *Proc. Natl. Acad. Sci. USA* 88:6575–6579; Young, J. W. et al. (1992) *J. Clin. Invest.* 90:229–237; Koulova, L. et al. (1991) *J. Exp. Med.* 173: 759–762; Reiser, H. et al. (1992) *Proc. Natl. Acad. Sci. USA* 89:271–275; van-Seventer, G. A. et al. (1990) *J. Immunol.* 144:4579–4586; LaSalle, J. M. et al. (1991) *J. Immunol.* 147:774–80; Dustin, M. I. et al. (1989) *J. Exp. Med.* 169: 503; Armitage, R. J. et al. (1992) *Nature* 357:80–82; Liu, Y. et al. (1992) *J. Exp. Med.* 175:437–445).

The CD80 (B7-1) and CD86 (B7-2) proteins, expressed on APCs, are critical costimulatory molecules (Freeman et al. (1991) *J. Exp. Med.* 174:625; Freeman et al. (1989) *J. Immunol.* 143:2714; Azuma et al. (1993) *Nature* 366:76; Freeman et al. (1993) *Science* 262:909). B7-2 appears to play a predominant role during primary immune responses, while B7-1, which is upregulated later in the course of an immune response, may be important in prolonging primary T cell responses or costimulating secondary T cell responses (Bluestone (1995) *Immunity* 2:555).

One receptor to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S. et al. (1991) *J. Exp. Med.* 173:721–730; Gimmi, C. D. et al. (1991) *Proc. Natl. Acad. Sci. USA* 88:6575–6579; June, C. H. et al. (1990) *Immunol. Today.* 11:211–6; Harding, F. A. et al. (1992) *Nature* 356:607–609). A second receptor, termed CTLA4 (CD152) is homologous to CD28 but is not expressed on resting T cells and appears following T cell activation (Brunet, J. F. et al. (1987) *Nature* 328:267–270). CTLA4 appears to be critical in negative regulation of T cell responses (Waterhouse et al. (1995) *Science* 270:985). Blockade of CTLA4 has been found to remove inhibitory signals, while aggregation of CTLA4 has been found to provide inhibitory signals that downregulate T cell responses (Allison and Krummel (1995) *Science* 270:932). The B7 molecules have a higher affinity for CTLA4 than for CD28 (Linsley, P. S. et al. (1991) *J. Exp. Med.* 174:561–569) and B7-1 and B7-2 have been found to bind to distinct regions of the CTLA4 molecule and have different kinetics of binding to CTLA4 (Linsley et al. (1994) *Immunity* 1:793). A new molecule related to CD28 and CTLA4, ICOS, has been identified and seems to be important in IL-10 production (Hutloff et al. (1999) *Nature* 397: 263; WO 98/38216), as has its ligand, which is a new B7 family member (Aicher A. et al. (2000) *J. Immunol.* 164: 4689–96; Mages H. W. et al. (2000) *Eur. J. Immunol.* 30:1040-7; Brodie D. et al. (2000) *Curr. Biol.* 10:333–6; Ling V. et al. (2000) *J. Immunol.* 164:1653–7; Yoshinaga S. K. et al. (1999) *Nature* 402:827–32). If T cells are only stimulated through the T cell receptor, without receiving an additional costimulatory signal, they become nonresponsive, anergic, or die, resulting in downmodulation of the immune response.

The importance of the B7:CD28/CTLA4 costimulatory pathway has been demonstrated in vitro and in several in vivo model systems. Blockade of this costimulatory pathway results in the development of antigen specific tolerance in murine and human systems (Harding, F. A. et al. (1992) *Nature* 356:607–609; Lenschow, D. J. et al. (1992) *Science* 257:789–792; Turka, L. A. et al. (1992) *Proc. Natl. Acad. Sci. USA* 89:11102–11105; Gimmi, C. D. et al. (1993) *Proc. Natl. Acad. Sci. USA* 90:6586–6590; Boussiotis, V. et al. (1993) *J. Exp. Med.* 178:1753–1763). Conversely, expression of B7 by B7 negative murine tumor cells induces T-cell mediated specific immunity accompanied by tumor rejection and long lasting protection to tumor challenge (Chen, L. et al. (1992) *Cell* 71:1093–1102; Townsend, S. E. and Allison, J. P. (1993) *Science* 259:368–370; Baskar, S. et al. (1993) *Proc. Natl. Acad. Sci.* 90:5687–5690.). Therefore, manipulation of the costimulatory pathways offers great potential to stimulate or suppress immune responses in humans.

SUMMARY OF THE INVENTION

The present invention is based, at least in part, on the discovery that PD-1 is a receptor for B7-4 molecules expressed on antigen presenting cells. PD-1 transmits a negative signal to immune cells, similar to CTLA4. B7-4 molecules are expressed on the surface of antigen presenting cells and provide a costimulatory signal to immune cells and can transmit downmodulatory signals to immune cells, depending upon the molecule to which they bind. Thus, modulation of PD-1, B7-4, and/or the interaction between B7-4 and PD-1 results in modulation of the immune response.

Accordingly, in one aspect, the invention relates to a method for modulating an immune response comprising contacting an immune cell with an agent that modulates signaling via PD-1 to thereby modulate the immune response. The immune cell may be, for instance, a T cell, a B cell, or a myeloid cell. In one embodiment, the step of contacting occurs in vivo. In another embodiment, the step of contacting occurs in vitro.

In one embodiment, the immune response is downregulated. This may occur, for instance by stimulating signaling via PD-1 using an agent selected from the group consisting of: an activating antibody that recognizes PD-1, a form of B7-4 that binds to an inhibitory receptor, and a small molecule that binds to PD-1.

In one embodiment, the stimulation of signaling via PD-1 induces anergy in the immune cell.

The method may further comprise contacting the immune cell with an additional agent that downregulates an immune response.

In yet another embodiment, the immune response is upregulated by inhibiton of signaling via PD-1. Signaling via PD-1 may be inhibited using an agent selected from the group consisting of: a blocking antibody that recognizes PD-1, a non-activating form of B7-4, an antibody that recognizes B7-4, and a soluble form of PD-1.

In another aspect, the invention pertains to a method for modulating the interaction of B7-4 with an inhibitory receptor on an immune cell comprising contacting an antigen presenting cell which expresses B7-4 with an agent selected from the group consisting of: a form of B7-4, a form of PD-1, or an agent that modulates the interaction of B7-4 and PD-1 such that the interaction of B7-4 with an inhibitory receptor on an immune cell is modulated. The immune cell may be, for instance, a T cell, a B cell, or a myeloid cell. In one embodiment, the step of contacting is performed in vitro. In another embodiment, the step of contacting is performed in vivo. The method may further comprise contacting the immune cell or the antigen presenting cell with an additional agent that modulates an immune response.

In another aspect, the invention pertains to a method for inhibiting activation of an immune cell via a non-apoptotic mechanism comprising increasing the activity or expression of PD-1 in the immune cell such that immune cell activation is inhibited.

In another aspect, the invention pertains to a vaccine comprising an antigen and an agent that inhibits signaling via PD-1 in an immune cell.

In another aspect, the invention pertains to a composition comprising an antigen and an agent that promotes signaling via PD-1 in an immune cell.

In another aspect, the invention pertains to a method for treating a subject having a condition that would benefit from upregulation of an immune response comprising administering an agent that inhibits signaling via PD-1 in an immune cell of the subject such that a condition that would benefit from upregulation of an immune response is treated. The condition may be, for instance, a tumor, a neurological disease or an immunosuppressive disease. In one embodiment, the agent that inhibits signaling via PD-1 comprises a soluble form of PD-1 or B7-4. In one embodiment, the method further comprises administering a second agent that upregulates an immune response to the subject.

In another aspect, the invention pertains to a method for treating a subject having a condition that would benefit from downregulation of an immune response comprising administering an agent that stimulates signaling via PD-1 in a immune cell of the subject such that a condition that would benefit from downregulation of an immune response is treated. The condition may be, for instance, a transplant, an allergy, or an autoimmune disorder. In one embodiment, the agent that stimulates signaling via PD-1 is an antibody that stimulates signaling via PD-1, a bispecific antibody, or soluble B7-4. The method may further comprise administering a second agent to the subject that downregulates an immune response.

In another aspect, the invention pertains to a cell-based assay for screening for compounds which modulate the activity of B7-4 or PD-1 comprising contacting a cell expressing a B7-4 target molecule or PD-1 target molecule with a test compound and determining the ability of the test compound to modulate the activity of the B7-4 or PD-1 target molecule.

In yet another aspect, the invention pertains to a cell-free assay for screening for compounds which modulate the binding of B7-4 or PD-1 to a target molecule comprising contacting a B7-4 or PD-1 protein or biologically active portion thereof with a test compound and determining the ability of the test compound to bind to the B7-4 or PD-1 protein or biologically active portion thereof.

BRIEF DESCRIPTION OF THE DRAWINGS

FIG. 1 depicts the nucleotide sequence encoding a human secreted B7-4, B7-4S (SEQ ID NO: 1).

FIG. 2 depicts the nucleotide sequence encoding a human B7-4, B7-4M (SEQ ID NO: 3).

FIG. 3 depicts the amino acid sequence of human B7-4S (SEQ ID NO: 2) and illustrates the signal, IgV, IgC, and hydrophilic tail domains.

FIG. 4 depicts the amino acid sequence of human B7-4M (SEQ ID NO: 4) and illustrates the signal, IgV, IgC, and transmembrane and cytoplasmic domains.

FIGS. 5A–5B depict the nucleotide sequence of murine B7-4 (SEQ ID NO: 22).

FIG. 6 depicts the amino acid sequence of murine B7-4 (SEQ ID NO: 23).

FIG. 7 depicts an alignment of the human B7-4M and murine B7-4 amino acid sequences (SEQ ID NO: 4 and 23 respectively).

FIG. 9 illustrates the results of FACS analysis of binding of IgG and murine ICOS-his fusion protein by B7-4M-transfected COS cells.

FIGS. 14A–14F illustrate the ability of added PD-1 and not Flt4 to compete for the binding of PD-1 to B7-4M transfected COS cells.

FIGS. 15A–15L illustrate the ability of PD-1 to bind to B7-4 transfected CHO cells, as determined by flow cytometry.

FIGS. 18A–18C illustrate the inhibition of T cell proliferation and cytokine production in human T cell stimulated in the presence of B7-4.

FIGS. 20A–20I illustrate the binding of PD-1 to CHO cells expressing B7-4.

FIGS. 22A–22D illustrate the inhibition of cytokine production by the PD-1:B7-4 pathway, as measured by cytokine ELISA.

FIG. 28A: CD4+ T cells. FIG. 28B: CD8+ T cells. PD-1:B7-4 interaction results in decreased mitotic divisions of both CD4+ and CD8+ T cells.

FIG. 29A illustrates schematically the cell lines and the experimental design. Stable antigen presenting cell (APC) lines were engineered to express GFP or mB7-4/GFP using retroviral technology. 5×10$^4$ purified LN T cells from TCR transgenic (Tg) mice were stimulated with APC plus peptide for 2, 2–3, 3, or 4 days. For experiments involving CD4+ T cells, the APC:T cell ratio was 1:10 with 10 µM PCCF peptide. For experiments involving CD8+ T cells, the APC:T cell ratio was 1:1 with 1 mM p2Ca peptide. FIG. 29B illustrates the inhibition of proliferation of CD4+ T cells by PD-1:B7-4 interaction. FIG. 29C illustrates the inhibition of proliferation of CD8+ T cells by PD-1:B7-4 interaction.

FIG. 30A: CD4+ T cells. FIG. 30B: CD8+ T cells.

FIGS. 31A–31B illustrate schematically a screening assay used to identify proteins involved in the PD-1 signaling pathway. FIG. 31A depicts a schematic of the steps of the assay. FIG. 31B depicts the sequences of a fragment of human PD-1 (SEQ ID NO: 24), a fragment of mouse PD-1 (SEQ ID NO: 25) and the peptides used in the assay. Peptides used in the assay are the ITIM peptides: PD-1_Py1 (SEQ ID NO: 26); PD-1_Y1F (SEQ ID NO: 27); PD-1_Y1 (SEQ ID NO: 28); PD-1_Py2 (SEQ ID NO: 29); PD-1_Y2F (SEQ ID NO: PD-1_Y2 (SEQ ID NO: 31); and Other Peptides: PD-1_K212_(SEQ ID NO: 32); PD-1_K212D (SEQ ID NO: 33); PD-1_K335 (SEQ ID NO: 34); PD-1_K335D (SEQ ID NO: 35); PD-1_Ctail1 (SEQ ID NO: 36); and PD-1_Ctail2 (SEQ ID NO: 37).

DETAILED DESCRIPTION OF THE INVENTION

Figure 8:
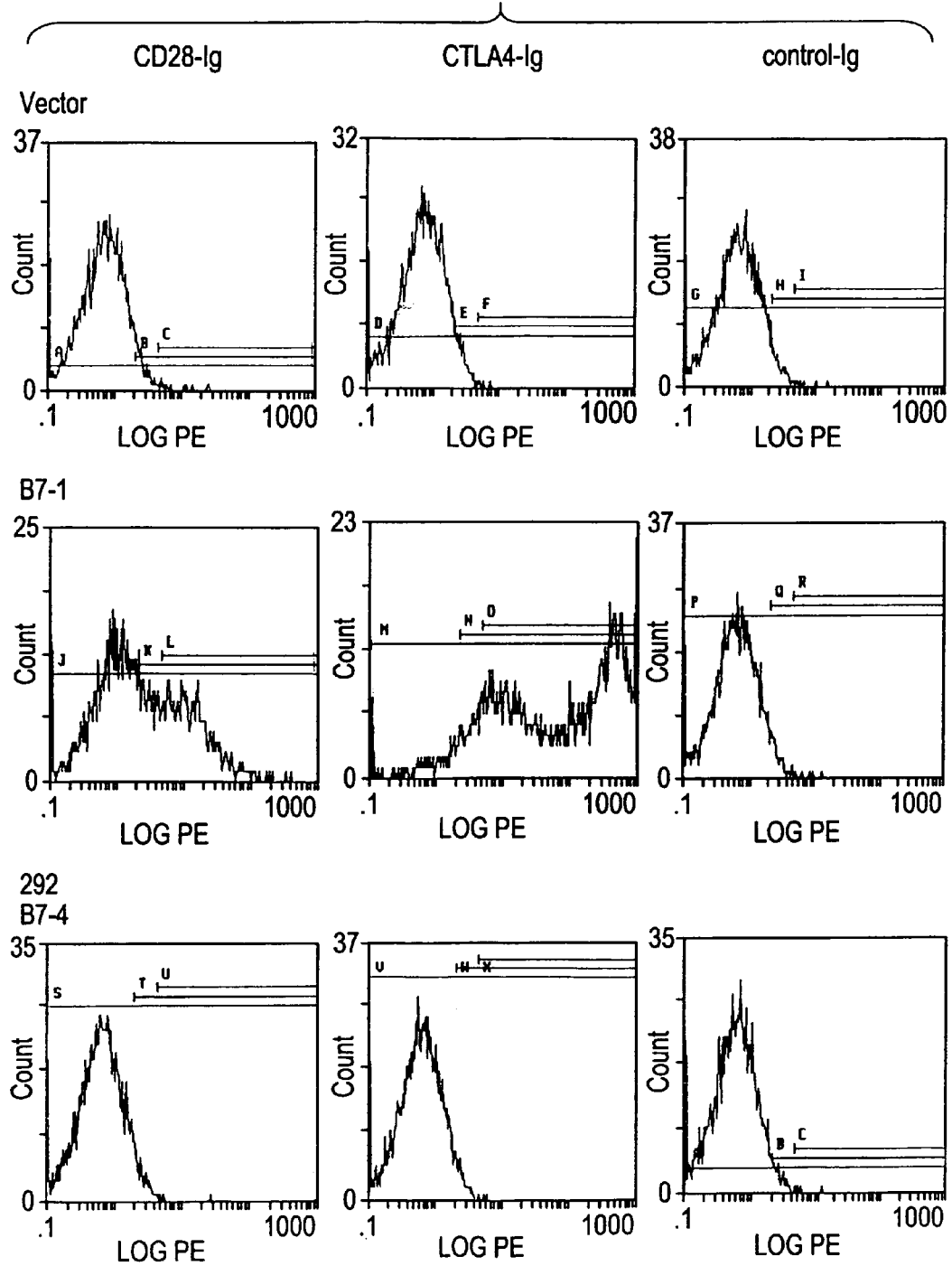
FIG. 8 illustrates the results of FACS analysis of binding of CD28Ig, CTLA4-Ig, and control Ig by B7-4M-transfected COS cells.

In addition to the previously characterized B lymphocyte activation antigens, e.g., B7-1 and B7-2, there are other an costimulation of immune cells. For example, B7-4 polypeptides have been isolated from keratinocyte and placental cDNA libraries. B7-4 has also been found to costimulate or inhibit T cells. The present invention identifies PD-1 as a receptor for B7-4.

Immune cells have receptors that transmit activating signals. For example, T cells have T cell receptors and the CD3 complex, B cells have B cell receptors, and myeloid cells have Fe receptors. In addition, immune cells bear receptors that transmit signals that provide costimulatory signals, or receptors that transmit signals that inhibit receptor-mediated signaling. For example, CD28 transmits a costimulatory signal to T cells. After ligation of the T cell receptor, ligation of CD28 results in a costimulatory signal characterized by, e.g., upregulation of IL-2rα, IL-2rβ, and IL-2rγ receptor, increased transcription of IL-2 messenger RNA, and increased expression of cytokine genes (including IL-2, IFN-γ, GM-CSF, and TNF-α). Transmission of a costimulatory signal allows the cell to progress through the cell cycle and, thus, increases T cell proliferation (Greenfield et al. (1998) *Crit. Rev. Immunol.* 18:389). Binding of a receptor on a T cell which transmits a costimulatory signal to the cell (e.g., ligation of a costimulatory receptor that leads to cytokine secretion and/or proliferation of the T cell) by a B7 family molecule, such as B7-4, results in costimulation. Thus, inhibition of an interaction between a B7 family molecule, such as B7-4, and a receptor that transmits a costimulatory signal on an immune cell results in a downmodulation of the immune response and/or specific unresponsiveness, termed immune cell anergy. Inhibition of this interaction can be accomplished using, e.g., anti-CD28 Fab fragments, antibodies to B7-1, B7-2 and/or B7-4, or by using a soluble form of a receptor to which a B7 family member molecule can bind as a competitive inhibitor (e.g., CTLA4Ig).

Inhibitory receptors that bind to costimulatory molecules have also been identified on immune cells. Activation of CTLA4, for example, transmits a negative signal to a T cell. Engagement of CTLA4 inhibits IL-2 production and can induce cell cycle arrest (Krummel and Allison (1996) *J. Exp. Med.* 183:2533). In addition, mice that lack CTLA4 develop lymphoproliferative disease (Tivol et al. (1995) *Immunity* 3:541; Waterhouse et al. (1995) *Science* 270:985). The blockade of CTLA4 with antibodies can block an inhibitory signal, whereas aggregation of CTLA4 with antibody transmits an inhibitory signal. Therefore, depending upon the receptor to which a costimulatory molecule binds (i.e., a costimulatory receptor such as CD28 or an inhibitory receptor such as CTLA4), certain B7 molecules including B7-4 can promote T cell costimulation or inhibition.

PD-1 is a member of the immunoglobulin family of molecules (Ishida et al. (1992) *EMBO J.* 11:3887; Shinohara et al. (1994) *Genomics* 23:704). PD-1 was previously identified using a subtraction cloning based approach designed to identify modulators of programmed cell death (Ishida et al. (1992) *EMBO J.* 11:3887–95; Woronicz et al. (1995) *Curr. Top. Microbiol. Immunol.* 200:137). PD-1 is believed to play a role in lymphocyte survival, e.g., during clonal selection (Honjo (1992) *Science* 258:591; Agata et al. (1996) *Int.*

*Immunology.* 8:765; Nishimura et al. (1996) *Int. Immunology* 8:773). PD-1 was also implicated as a regulator of B cell responses (Nishimura (1998) *Int. Immunology* 10:1563). Unlike CTLA4, which is found only on T cells, PD-1 is also found on B cells and myeloid cells.

The instant discovery that PD-1 binds to B7-4 places PD-1 in a family of inhibitory receptors with CTLA4. While engagement (to produce activation) of a costimulatory receptor results in a costimulatory signal in an immune cell, engagement of an inhibitory receptor, e.g., CTLA4 or PD-1 (for example by crosslinking or by aggregation), leads to the transmission of an inhibitory signal in an immune cell, resulting in downmodulation of immune cell responses and/or in immune cell anergy. While transmission of an inhibitory signal leads to downmodulation in immune cell responses (and a resulting downmodulation in the overall immune response), the prevention of an inhibitory signal (e.g., by using a non-activating antibody against PD-1) in immune cells leads to upmodulation of immune cell responses (and a resulting upmodulation of an immune response).

The instant invention makes available agents useful for modulating the activity and/or expression of PD-1; the interaction between PD-1 and its natural ligand(s), (e.g., B7-4); and agents for modulating the immune response via modulation of the interaction between PD-1 and its natural ligand, e.g., B7-4, also known as PD-L1. Exemplary modulatory agents for use in these methods are described further as follows.

B7-4 and PD-1 Nucleic Acid and Polypeptide Molecules

In one embodiment, a modulatory agent useful for modulating the activity and/or expression of PD-1 is a B7-4 and/or PD-1 nucleic acid molecule, preferably a human B7-4 and/or PD-1 nucleic acid molecule.

In one embodiment, the isolated nucleic acid molecules of the present invention encode eukaryotic B7-4 or PD-1 polypeptides. The B7-4 family of molecules share a number of conserved regions, including signal domains, IgV domains and the IgC domains. IgV domains and the IgC domains are art recognized Ig superfamily member domains. These domains correspond to structural units that have distinct folding patterns called Ig folds. Ig folds are comprised of a sandwich of two β sheets, each consisting of antiparallel β strands of 5–10 amino acids with a conserved disulfide bond between the two sheets in most, but not all, domains. IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than C-domains and form an additional pair of β strands.

Two forms of human B7-4 molecules have been identified. One form is a naturally occurring B7-4 soluble polypeptide, i.e., having a short hydrophilic domain and no transmembrane domain, and is referred to herein as B7-4S (shown in SEQ ID NO:2). The second form is a cell-associated polypeptide, i.e., having a transmembrane and cytoplasmic domain, referred to herein as B7-4M (shown in SEQ ID NO:4).

B7-4 proteins comprise a signal sequence, and an IgV domain and an IgC domain. The signal sequence of SEQ ID NO:2 is shown from about amino acid 1 to about amino acid 18. The signal sequence of SEQ ID NO:4 is shown from about amino acid 1 to about amino acid 18. The IgV domain of SEQ ID NO:2 is shown from about amino acid 19 to about amino acid 134 and the IgV domain of SEQ ID NO:4 is shown from about amino acid 19 to about amino acid 134. The IgC domain of SEQ ID NO:2 is shown from about amino acid 135 to about amino acid 227 and the IgC domain of SEQ ID NO:4 is shown from about amino acid 135 to about amino acid 227. The hydrophilic tail of the B7-4 exemplified in SEQ ID NO:2 comprises a hydrophilic tail shown from about amino acid 228 to about amino acid 245. The B7-4 polypeptide exemplified in SEQ ID NO:4 comprises a transmembrane domain shown from about amino acids 239 to about amino acid 259 of SEQ ID NO:4 and a cytoplasmic domain shown from about amino acid 260 to about amino acid 290 of SEQ ID NO:4.

Murine B7-4 molecules are also identified. The murine cDNA sequence is presented in FIGS. 5A–5B and the murine B7-4 amino acid sequence is presented in FIG. 6. The present invention also pertains to these murine B7-4 molecules.

PD-1 is identified herein as a receptor which binds to B7-4. PD-1 molecules are members of the immunoglobulin gene superfamily. PD-1 (Ishida et al. (1992) *EMBO J.* 11:3887; Shinohara et al. (1994) *Genomics* 23:704; U.S. Pat. No. 5,698,520) has an extracellular region containing immunoglobulin superfamily domain, a transmembrane domain, and an intracellular region including an immunoreceptor tyrosine-based inhibitory motif (ITIM). These features also define a larger family of molecules, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC molecules, for example the KIRs, and CTLA4 bind to B7-1 and B7–2. It has been proposed that there is a phylogenetic relationship between the MHC and B7 genes (Henry et al. (1999) *Immunol. Today* 20(6): 285–8).

The nucleotide sequence of PD-1 is shown in SEQ ID NO:10 and 11 and the amino acid sequence of PD-1 is shown in SEQ ID NO:12 (see also Ishida et al. (1992) *EMBO J.* 11:3887; Shinohara et al. (1994) *Genomics* 23:704; U.S. Pat. No. 5,698,520). PD-1 was previously identified using a subtraction cloning based approach to select for proteins involved in apoptotic cell death. PD-1 is identified herein as a member of the CD28/CTLA-4 family of molecules based on its ability to bind to B7-4. Like CTLA4, PD-1 is rapidly induced on the surface of T-cells in response to anti-CD3 (Agata et al. (1996) *Int. Immunol.* 8:765). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773). The instant invention identifies B7-4 as a ligand of PD-1.

Various aspects of the invention are described in further detail in the following subsections:

I. Definitions

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

As used herein, the term "T cell" includes cells bearing a T cell receptor (TCR). Preferably, the term "T cell" inculdes CD4+ T cells and/or CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4 or PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory molecules (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis.

As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

Depending upon the form of the B7-4 molecule that binds to a receptor, either a signal can be transmitted or stimulated (e.g., by a multivalent form of a B7-4 molecule that results in crosslinking of receptor) or a signal can be inhibited (e.g., by a soluble, monovalent form of a B7-4 molecule), e.g., by competing with activating forms of B7-4 molecules for binding to the receptor. However, there are instances in which a soluble molecule can be stimulatory. The effects of the various modulatory agents can be easily demonstrated using routine screening assays as described herein.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "activating receptor" includes immune cell receptors that bind antigen, complexed antigen (e.g., in the context of MHC molecules), or bind to antibodies. Such activating receptors include T cell receptors (TCR), B cell receptors (BCR), cytokine receptors, LPS receptors, complement receptors, and Fc receptors.

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

B cell receptors are present on B cells. B cell antigen receptors are a complex between membrane Ig (mIg) and other transmembrane polypeptides (e.g., Igα and Igβ). The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

Fc receptors are found on many cells which participate in immune responses. Fc receptors (FcRs) are cell surface receptors for the Fc portion of immunoglobulin molecules (Igs). Among the human FcRs that have been identified so far are those which recognize IgG (designated Fcγ R), IgE (Fcε R1), IgA (Fcα), and polymerized IgM/A (Fcμα R). FcRs are found in the following cell types: Fcε R I (mast cells), Fcε R.II (many leukocytes), Fcα R (neutrophils), and Fcμα R (glandular epithelium, hepatocytes) (Hogg, N. (1988) *Immunol. Today* 9:185–86). The widely studied FcγRs are central in cellular immune defenses, and are responsible for stimulating the release of mediators of inflammation and hydrolytic enzymes involved in the pathogenesis of autoimmune disease (Unkeless, J. C. et al. (1988) *Annu. Rev. Immunol.* 6:251–81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporine A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor (e.g., CTLA4 or PD-1) for a molecule on a immune cell. Such a signal antagonizes a signal produced by an activating receptor (e.g., via a TCR, CD3, BCR, or Fc molecule) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

The B7-4 protein and nucleic acid molecules comprise a family of molecules having certain conserved structural and functional features. Similarly, the PD-1 protein and nucleic acid molecules are members of a family of molecules having conserved structural and functional features. The term "family" when referring to the protein and nucleic acid molecules is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. The B7-4 molecules described herein are members of the B7 family of molecules. The term "B7 family" or "B7 molecules" as used herein includes costimulatory molecules that share sequence homology with B7 polypeptides, e.g., with B7-1, B7-2, B7-3 (recognized by the antibody BB-1), B7h (Swallow et al. (1999) *Immunity* 11:423), and/or B7-4. For example, human B7-1 and B7-2 share approximately 26% amino acid sequence identity when compared using the BLAST program at NCBI with the default parameters (Blosum62 matrix with gap penalties set at existence 11 and extension 1 (See the NCBI website.)

Preferred B7 polypeptides are capable of providing costimulatory or inhibitory signals to immune cells to thereby promote or inhibit immune cell responses. For example, when bound to a costimulatory receptor, B7-4 can induce costimulation of immune cells or can inhibit immune cell costimulation, e.g., when present in soluble form. When bound to an inhibitory receptor, B7-4 molecules can transmit an inhibitory signal to an immune cell. Preferred B7 family members include B7-1, B7-2, B7-3 (recognized by the antibody BB-1), B7h, and B7-4 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Preferred PD-1 molecules are capable of transmitting an inhibitory signal to an immune cell to thereby inhibit immune cell effector function or are capable of promoting costimulation (e.g., by competitive inhibition) of immune cells, e.g., when present in soluble, monomeric form. PD-1 induced signaling (also referred to herein as signaling via PD-1) is defined herein as one or more cellular events directly or indirectly induced in an immune cell which expresses PD-1 on its cell surface, by the binding if the receptor to a ligand, or other molecule, to activate the PD-1. Activation of PD-1 triggers a secondary signaling event which results in a cellular change. Such a cellular event can be detected, for instance, by inhibition of costimulation in a T cell activation assay, or by increased phosphorylation of the SHP-2 molecule, decreased phosphorylation of the ERK1/2 molecule, or decreased phosphorylation of the PKC-θ molecule. Under the appropriate circumstances the PD-1 induced signaling results in the downmodulation of an immune response by the immune cell. Preferred PD-1 family members bind to one or more ligands, e.g., B7-1, B7-2, B7-4, and/or other molecules on antigen presenting cells, and share sequence identity with PD-1.

In addition, in one embodiment, proteins that are members of a protein family are bound by antibodies generated against one or more other family member proteins. For example, the anti-BB1 antibody recognizes B7-4 molecules.

As used herein, the term "activity" with respect to a B7-4 or PD-1 polypeptide includes activities which are inherent in the structure of a B7-4 or PD-1 protein. With regard to B7-4, the term "activity" includes the ability to modulate immune cell costimulation, e.g., by modulating a costimulatory signal in an activated immune cell, or to modulate inhibition by modulating an inhibitory signal in an immune cell, e.g., by engaging a natural receptor on a immune cell. When an activating form of the B7-4 molecule binds to a costimulatory receptor, a costimulatory signal is generated in the immune cell. When an activating form of the B7-4 molecule binds to an inhibitory receptor, an inhibitory signal is generated in the immune cell.

Modulation of a costimulatory signal results in modulation of effector function of an immune cell. Thus, the term "B7-4 activity" includes the ability of a B7-4 polypeptide to bind its natural receptor(s), the ability to modulate immune cell costimulatory or inhibitory signals, and the ability to modulate the immune response.

With respect to PD-1, the term "activity" includes the ability of a PD-1 polypeptide to modulate an inhibitory signal in an activated immune cell, e.g., by engaging a natural ligand on an antigen presenting cell. PD-1 transmits an inhibitory signal to an immune cell in a manner similar to CTLA4. Modulation of an inhibitory signal in an immune cell results in modulation of proliferation of and/or cytokine secretion by the immune cell. PD-1 can also modulate a costimulatory signal by competing with a costimulatory receptor for binding of a B7 molecule. Thus, the term "PD-1 activity" includes the ability of a PD-1 polypeptide to bind its natural ligand(s), the ability to modulate immune cell costimulatory or inhibitory signals, and the ability to modulate the immune response.

As used herein, a "naturally-occurring" nucleic acid molecule refers to an RNA or DNA molecule having a nucleotide sequence that occurs in nature (e.g., encodes a natural protein).

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein", refers to a protein that is substantially free of other proteins, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the B7-4 or PD-1 protein is derived, or substantially free from chemical precursors or other chemicals when chemically synthesized. The language "substantially free of cellular material" includes preparations of B7-4 or PD-1 protein in which the protein is separated from cellular components of the cells from which it is isolated or recombinantly produced. In one embodiment, the language "substantially free of cellular material" includes preparations of B7-4 or PD-1 protein having less than about 30% (by dry weight) of non-B7-4 or PD-1 protein (also referred to herein as a "contaminating protein"), more preferably less than about 20% of non-B7-4 or PD-1 protein, still more preferably less than about 10% of non-B7-4 or PD-1 protein, and most preferably less than about 5% non-B7-4 or PD-1 protein. When the B7-4 or PD-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of B7-4 or PD-1 protein in which the protein is separated from chemical precursors or other chemicals which are involved in the synthesis of the protein. In one embodiment, the language "substantially free of chemical precursors or other chemicals" includes preparations of B7-4 or PD-1 protein having less than about 30% (by dry weight) of chemical precursors or non-B7-4 or PD-1 chemicals, more preferably less than about 20% chemical precursors or non-B7-4 or PD-1 chemicals, still more preferably less than about 10% chemical precursors or non-B7-4 or PD-1 chemicals, and most preferably less than about 5% chemical precursors or non-B7-4 or PD-1 chemicals.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., B7-4). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHI domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883; and Osbourn et al. (1998) *Nat. Biotechnol.* 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) *Proc. Natl Acad. Sci. USA* 90:6444–6448; Poljak, R. J. et al. (1994) *Structure* 2:1121–1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93–101) and use of a cysteine residue, a marker peptide and a C-terminal polyhistidine tag to make bivalent and biotinylated scFv molecules (Kipriyanov, S. M., et al. (1994) *Mol. Immunol.* 31:1047–1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g. humanized, chimeric, etc. Preferably, antibodies of the invention bind specifically or substantially specifically to B7-4 molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds B7-4 is substantially free of antibodies that specifically bind antigens other than B7-4).

Moreover, an isolated antibody may be substantially free of other cellular material and/or chemicals.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, GAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a B7-4 or PD-1 polypeptide of the invention (or any portion thereof) can be used to derive the B7-4 or PD-1 amino acid sequence, using the genetic code to translate the DNA or RNA molecule into an amino acid sequence. Likewise, for any B7-4 or PD-1-amino acid sequence, corresponding nucleotide sequences that can encode B7-4 or PD-1 protein can be deduced from the genetic code (which, because of its redundancy, will produce multiple nucleic acid sequences for any given amino acid sequence). Thus, description and/or disclosure herein of a B7-4 or PD-1 nucleotide sequence should be considered to also include description and/or disclosure of the amino acid sequence encoded by the nucleotide sequence. Similarly, description and/or disclosure of a B7-4 or PD-1 amino acid sequence herein should be considered to also include description and/or disclosure of all possible nucleotide sequences that can encode the amino acid sequence.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

II. Isolated Nucleic Acid Molecules

In one embodiment, modulating agents for use in the claimed methods comprise isolated nucleic acid molecules that encode B7-4 or PD-1 proteins or biologically active portions thereof. Nucleic acid fragments sufficient for use as hybridization probes to identify B7-4 or PD-1-encoding nucleic acids (e.g., B7-4 or PD-1 mRNA) and fragments for use as PCR primers for the amplification or mutation of B7-4 or PD-1 nucleic acid molecules are also provided. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid) in the genomic DNA of the organism from which the nucleic acid molecule is derived. For example, in various embodiments, the isolated B7-4 or PD-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" B7-4 or PD-1 nucleic acid molecule may, however, be linked to other nucleotide sequences that do not normally flank the B7-4 or PD-1 sequences in genomic DNA (e.g., the B7-4 or PD-1 nucleotide sequences may be linked to vector sequences). In certain preferred embodiments, an "isolated" nucleic acid molecule, such as a cDNA molecule, also may be free of other cellular material. However, it is not necessary for the B7-4 or PD-1 nucleic acid molecule to be free of other cellular material to be considered "isolated" (e.g., a B7-4 or PD-1 DNA molecule separated from other mammalian DNA and inserted into a bacterial cell would still be considered to be "isolated").

A nucleic acid molecule of the present invention, e.g., a nucleic acid molecule having the nucleotide sequence of SEQ ID NO:1, 3, 10, or 11 or a portion thereof, can be isolated using standard molecular biology techniques and the sequence information provided herein. For example, using all or portion of the nucleic acid sequence of SEQ ID NO:1, 3, 10, or 11, as a hybridization probe, B7-4 or PD-1 nucleic acid molecules can be isolated using standard hybridization and cloning techniques (e.g., as described in Sambrook, J. et al. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 3, 10, or 11 can be isolated by the polymerase chain reaction (PCR) using synthetic oligonucleotide primers designed based upon the sequence of SEQ ID NO:1, 3, 10, or 11, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to B7-4 or PD-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, 3, 10, or 11.

In another preferred embodiment, an isolated nucleic acid molecule of the invention comprises a nucleic acid molecule which is a complement of the nucleotide sequence shown in SEQ ID NO:1, 3, 10, or 11, or a portion of any of these nucleotide sequences. A nucleic acid molecule which is complementary to the nucleotide sequence shown in SEQ ID NO:1, 3, 10, or 11, is one which is sufficiently complementary to the nucleotide sequence shown in SEQ ID NO:1, 3, 10, or 11, respectively, such that it can hybridize to the nucleotide sequence shown in SEQ ID NO:1, 3, 10, or 11, respectively, thereby forming a stable duplex. An exact complement is 100% homologous to a specified nucleotide sequence.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1, 3, 10, or 11, or a portion of any of these nucleotide sequences.

Moreover, the nucleic acid molecule of the invention can comprise only a portion of the nucleic acid sequence of SEQ ID NO:1, 3, 10, or 11, for example a fragment which can be used as a probe or primer or a fragment encoding a biologically active portion of a B7-4 or PD-1 protein. The nucleotide sequence determined from the cloning of the B7-4 or PD-1 genes allows for the generation of probes and primers designed for use in identifying and/or cloning other B7-4 or PD-1 family members, as well as B7-4 or PD-1 family homologues from other species. The probe/primer typically comprises a substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 10, or 11, or of a naturally occurring allelic variant or mutant of SEQ ID NO:1, 3, 10, or 11. In an exemplary embodiment, a nucleic acid molecule of the present invention comprises a nucleotide sequence which is at least 350, 400, 450, 500, 550, 600, 650, 700, 750, or 800 nucleotides in length and hybridizes under stringent hybridization conditions to a nucleic acid molecule of SEQ ID NO:1, 3, 10, or 11.

In another embodiment, a second nucleic acid molecule comprises at least about 500, 600, 700, 800, 900, or 1000 contiguous nucleotides of SEQ ID NO:1, 3, 10, or 11.

In one embodiment, a nucleic acid molecule of the invention, e.g., for use as a probe, does not include the portion of SEQ ID NO:1 from about nucleotides 815 to about 850 of SEQ ID NO:1 or about nucleotides 320 to 856 of SEQ ID NO:1. In another embodiment, a nucleic acid molecule of the invention does not include the portion of SEQ ID NO:3 from about nucleotides 314 to about 734, or from about nucleotides 835 to about 860, or from about nucleotides 1085 to about 1104 or from about nucleotides 1286 to about 1536 of SEQ ID NO:3.

In one embodiment, a nucleic acid molecule of the invention comprises at least about 500 contiguous nucleotides of SEQ ID NO:1 or SEQ ID NO:3. In a preferred embodiment, a nucleic acid molecule of the invention comprises at least about 600, at least about 700, at least about 800, at least about 900 or at least about 950 contiguous nucleotides of SEQ ID NO:1 or about 1000 contiguous nucleotides of SEQ ID NO:3. In another embodiment, a nucleic acid molecule of the invention comprises at least about 1500 or 1550 nucleotides of SEQ ID NO:3

Preferably, an isolated nucleic acid molecule of the invention comprises at least a portion of the coding region of SEQ ID NO:1 (shown in nucleotides 59–793) or SEQ ID NO:3 (shown in nucleotides 53–922). In another embodiment, a B7-4 nucleic acid molecule comprises from about nucleotide 1 to about nucleotide 319 of SEQ ID NO:1. In another embodiment, a B7-4 nucleic acid molecule comprises from about nucleotide 855 to about nucleotide 968 of SEQ ID NO:1. In another embodiment, a B7-4 nucleic acid molecule comprises from about nucleotide 1 to about nucleotide 314 of SEQ ID NO:3. In another embodiment, a B7-4 nucleic acid molecule comprises from about nucleotide 955 to about nucleotide 1285 of SEQ ID NO:3. In another embodiment, a B7-4 nucleic acid molecule comprises from about nucleotide 1535 to about nucleotide 1552 of SEQ ID NO:3.

In other embodiments, a nucleic acid molecule of the invention has at least 70% identity, more preferably 80% identity, and even more preferably 90% identity with a nucleic acid molecule comprising: at least about 500, at least about 600, at least about 700, at least about 800, at least about 900 or at least about 1000 contiguous nucleotides of SEQ ID NO:1 or SEQ ID NO:3.

Probes based on the B7-4 or PD-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a B7-4 or PD-1 protein, such as by measuring a level of a B7-4 or PD-1-encoding nucleic acid in a sample of cells from a subject e.g., detecting B7-4 or PD-1 mRNA levels or determining whether a genomic B7-4 or PD-1 gene has been mutated or deleted.

A nucleic acid fragment encoding a "biologically active portion of a B7-4 or PD-1 protein" can be prepared by isolating a portion of the nucleotide sequence of SEQ ID NO:1, 3, 10, or 11 which encodes a polypeptide having a B7-4 or PD-1 biological activity (the biological activities of the B7-4 or PD-1 proteins are described herein), expressing the encoded portion of the B7-4 or PD-1 protein (e.g., by recombinant expression in vitro) and assessing the activity of the encoded portion of the B7-4 or PD-1 protein.

Nucleic acid molecules that differ from SEQ ID NO:1, 3, 10, or 11 due to degeneracy of the genetic code, and thus encode the same B7-4 or PD-1 protein as that encoded by SEQ ID NO:1, 3, 10, or 11, are encompassed by the invention. Accordingly, in another embodiment, an isolated nucleic acid molecule of the invention has a nucleotide sequence encoding a protein having an amino acid sequence shown in SEQ ID NO:2, 4, or 12. In another embodiment, an isolated nucleic acid molecule of the invention has a nucleotide sequence encoding a B7-4 or PD-1 protein. In addition to the B7-4 or PD-1 nucleotide sequences shown in SEQ ID NO:1, 3, 10, or 11 it should be appreciated by those skilled in the art that DNA sequence polymorphisms that lead to changes in the amino acid sequences of the B7-4or PD-1 proteins may exist within a population (e.g., the human population). Such genetic polymorphism in the B7-4 or PD-1 genes may exist among individuals within a population due to natural allelic variation. As used herein, the terms "gene" and "recombinant gene" refer to nucleic acid molecules which include an open reading frame encoding a B7-4 or PD-1 protein, preferably a mammalian B7-4 or PD-1 protein, and can further include non-coding regulatory sequences, and introns. Such natural allelic variations include both functional and non-functional B7-4 or PD-1 proteins and can typically result in 1–5% variance in the nucleotide sequence of a B7-4 or PD-1 gene. Such nucleotide variations and resulting amino acid polymorphisms in B7-4 or PD-1 genes that are the result of natural allelic variation and that do not alter the functional activity of a B7-4 or PD-1 protein are intended to be within the scope of the invention.

Moreover, nucleic acid molecules encoding other B7-4 or PD-1 family members and, thus, which have a nucleotide sequence which differs from the B7-4 or PD-1 family sequences of SEQ ID NO:1, 3, 10, or 11 are intended to be within the scope of the invention. For example, another B7-4 or PD-1 cDNA can be identified based on the nucleotide sequence of human B7-4 or PD-1. Moreover, nucleic acid molecules encoding B7-4 or PD-1 proteins from different species, and thus which have a nucleotide sequence which differs from the B7-4 or PD-1 sequences of SEQ ID NO:1, 3, 10, or 11 are intended to be within the scope of the invention. For example, a mouse B7-4 or PD-1 cDNA can be identified based on the nucleotide sequence of a human B7-4 or PD-1 molecule.

Nucleic acid molecules corresponding to natural allelic variants and homologues of the B7-4 or PD-1 cDNAs of the invention can be isolated based on their homology to the B7-4 or PD-1 nucleic acids disclosed herein using the cDNAs disclosed herein, or a portion thereof, as a hybridization probe according to standard hybridization techniques. For example, a B7-4 or PD-1 DNA can be isolated from a human genomic DNA library using all or portion of SEQ ID NO:1, 3, 10, or 11 as a hybridization probe and standard hybridization techniques (e.g., as described in Sambrook, J., et al. *Molecular Cloning: A Laboratory Manual.* 2nd, ed., Cold Spring Harbor Laboratory, Cold Spring Harbor, N.Y., 1989). Moreover, a nucleic acid molecule encompassing all or a portion of a B7-4 or PD-1 gene can be isolated by the polymerase chain reaction using oligonucleotide primers designed based upon the sequence of SEQ ID NO:1, 3, 10, or 11. For example, mRNA can be isolated from cells (e.g., by the guanidinium-thiocyanate extraction procedure of Chirgwin et al. (1979) *Biochemistry* 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1, 3, 10, or 11. A nucleic acid molecule of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a B7-4 or PD-1 nucleotide sequence can be prepared by standard synthetic techniques, e.g., using an automated DNA synthesizer.

In another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 10, or 11. In other embodiment, the nucleic acid molecule is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, 3, 10, or 11 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). In addition to the B7-4 or PD-1 nucleotide sequences shown in SEQ ID NO:1, 3, 10, and 11, it should be appreciated by those skilled in the art that DNA sequence polymorphisms that lead to minor changes in the nucleotide or amino acid sequences of a B7-4 or PD-1 may exist within a population. Such genetic polymorphism in a B7-4 or PD-1 gene may exist among individuals within a population due to natural allelic variation. Such natural allelic variations can typically result in 1–2% variance in the nucleotide sequence of the gene. Such nucleotide variations and resulting amino acid polymorphisms in a B7-4 or PD-1 that are the result of natural allelic variation and that do not alter the functional activity of a B7-4 or PD-1 polypeptide are within the scope of the invention.

In addition to naturally-occurring allelic variants of B7-4 or PD-1 sequences that may exist in the population, the skilled artisan will further appreciate that minor changes may be introduced by mutation into nucleotide sequences, e.g., of SEQ ID NO: 1, 3, 10, or 11, thereby leading to changes in the amino acid sequence of the encoded protein, without altering the functional activity of a B7-4 or PD-1 protein. For example, nucleotide substitutions leading to amino acid substitutions at "non-essential" amino acid residues may be made in the sequence of SEQ ID NO:1, 3, 10, or 11. A "non-essential" amino acid residue is a residue that can be altered from the wild-type sequence of a B7-4 nucleic acid molecule (e.g., the sequence of SEQ ID NO:1, 3, 10, or 11) without altering the functional activity of a B7-4 or PD-1 molecule. Preferably, residues in the extracellular domain of B7-4 or PD-1 which are found to be required for binding of B7-4 to a receptor or PD-1 to a natural ligand (e.g., identified using an alanine scanning mutagenesis screen or other art recognized screening assay) are not altered. For B7-4 molecules, exemplary residues which are non-essential and, therefore, amenable to substitution, can be identified by one of ordinary skill in the art by performing an amino acid alignment of B7 family members (or of B7-4 family members) and determining residues that are not conserved. Such residues, because they have not been conserved, are more likely amenable to substitution.

Accordingly, another aspect of the invention pertains to nucleic acid molecules encoding B7-4 or PD-1 proteins that contain changes in amino acid residues that are not essential for a B7-4 or PD-1 activity. Such B7-4 or PD-1 proteins differ in amino acid sequence from SEQ ID NO: 2, 4, or 12 yet retain an inherent B7-4 activity or, in the case of PD-1, retain the ability to bind to B7-4. An isolated nucleic acid molecule encoding a non-natural variant of a B7-4 or PD-1 protein can be created by introducing one or more nucleotide substitutions, additions or deletions into the nucleotide sequence of SEQ ID NO:1, 3, 10, or 11 such that one or more amino acid substitutions, additions or deletions are introduced into the encoded protein. Mutations can be introduced into SEQ ID NO:1, 3, 10, or 11 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a B7-4 or PD-1 is preferably replaced with another amino acid residue from the same side chain family.

Alternatively, in another embodiment, mutations can be introduced randomly along all or part of a B7-4 or PD-1 coding sequence, such as by saturation mutagenesis, and the resultant mutants can be screened for their ability to bind to DNA and/or activate transcription, to identify mutants that retain functional activity. Following mutagenesis, the encoded B7-4 or PD-1 mutant protein can be expressed recombinantly in a host cell and the functional activity of the mutant protein can be determined using assays available in the art for assessing a B7-4 or PD-1 activity.

Accordingly, another aspect of the invention pertains to nucleic acid molecules encoding B7-4 or PD-1 proteins that contain changes in amino acid residues that are not essential for activity.

Yet another aspect of the invention pertains to isolated nucleic acid molecules encoding a B7-4 or PD-1 fusion proteins. Such nucleic acid molecules, comprising at least a first nucleotide sequence encoding a B7-4 or PD-1 protein, polypeptide or peptide operatively linked to a second nucleotide sequence encoding a non- a B7-4 or PD-1 protein, polypeptide or peptide, can be prepared by standard recombinant DNA techniques.

In a preferred embodiment, a mutant B7-4 protein can be assayed for the ability to: 1) costimulate (or inhibit the costimulation of, e.g., in soluble form) the proliferation and/or effector function of activated immune cells; 2) bind to an anti-B7 family- or anti B7-4-antibody; and/or 3) bind to a natural receptor(s) of B7-4 (e.g., PD-1).

In a preferred embodiment, a mutant PD-1 protein can be assayed for the ability to: 1) inhibit the costimulation of (e.g., in soluble form) the proliferation and/or effector function of activated immune cells; 2) bind to an anti-PD-1 antibody; and/or 3) bind to a natural ligand(s) of PD-1 (e.g., B7-4).

In addition to the nucleic acid molecules encoding B7-4 or PD-1 proteins described above, isolated nucleic acid molecules which are antisense thereto can be used as modulating agents. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire B7-4 or PD-1 coding strand, or only to a portion thereof. In one embodiment, an antisense nucleic acid molecule is antisense to a "coding region" of the coding strand of a nucleotide sequence encoding B7-4 or PD-1. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding B7-4 or PD-1. The term "noncoding region" refers to 5' and 3' sequences which flank the coding region that are not translated into amino acids (i.e., also referred to as 5' and 3' untranslated regions).

Given the coding strand sequences encoding B7-4 or PD-1 disclosed herein, antisense nucleic acids of the invention can be designed according to the rules of Watson and Crick base pairing. The antisense nucleic acid molecule can be complementary to the entire coding region of B7-4 or PD-1 mRNA, but more preferably is an oligonucleotide which is antisense to only a portion of the coding or noncoding region of B7-4 or PD-1 mRNA. For example, the antisense oligonucleotide can be complementary to the region surrounding the translation start site of B7-4 or PD-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid is of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a B7-4 or PD-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid molecule of the invention is a ribozyme. Ribozymes are catalytic RNA molecules with ribonuclease activity which are capable of cleaving a single-stranded nucleic acid molecule, such as an mRNA, to which they have a complementary region. Thus, ribozymes (e.g., hammerhead ribozymes (described in Haseloff and Gerlach (1988) *Nature* 334: 585–591)) can be used to catalytically cleave B7-4 or PD-1 mRNA transcripts to thereby inhibit translation of B7-4 or PD-1 mRNA. A ribozyme having specificity for a B7-4 or PD-1-encoding nucleic acid can be designed based upon the nucleotide sequence of a B7-4 or PD-1 cDNA disclosed herein (i.e., SEQ ID NO:1, 3, 10, or 11). For example, a derivative of a Tetrahymena L-19 IVS RNA can be constructed in which the nucleotide sequence of the active site is complementary to the nucleotide sequence to be cleaved in a B7-4 or PD-1-encoding mRNA. See, e.g., Cech et al. U.S. Pat. No. 4,987,071; and Cech et al. U.S. Pat. No. 5,116,742. Alternatively, B7-4 or PD-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, B7-4 or PD-1 gene expression can be inhibited by targeting nucleotide sequences complementary to the regulatory region of the B7-4 or PD-1 (e.g., the B7-4 or PD-1 promoter and/or enhancers) to form triple helical structures that prevent transcription of the B7-4 or PD-1 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioessays* 14(12):807–15.

In yet another embodiment, the B7-4 or PD-1 nucleic acid molecules of the present invention can be modified at the base moiety, sugar moiety, or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem.* 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670–675.

PNAs of B7-4 or PD-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of B7-4 or PD-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup and Nielsen (1996) supra)); or as probes or primers for DNA sequencing or hybridization (Hyrup B. and Nielsen (1996) supra; Perry-O'Keefe et al. (1996) supra).

In another embodiment, PNAs of B7-4 or PD-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of B7-4 or PD-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. and Nielsen (1996) supra). The synthesis of PNA-DNA chimeras can be performed as described in Hyrup B. and Nielsen (1996) supra and Finn P. J. et al. (1996) *Nucleic Acids Res.* 24(17):3357–63. For example, a DNA chain can be synthesized on a solid support using standard phosphoramidite coupling chemistry. Modified nucleoside analogs, (e.g., 5'-(4-methoxytrityl)amino-5'-deoxy-thymidine phosphoramidite), can be used as a linker between the PNA and the 5' end of DNA (Mag, M. et al. (1989) *Nucleic Acids Res.* 17:5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Biotechniques* 6:958–976) or intercalating agents (See, e.g., Zon (1988) *Pharm. Res.* 5:539–549). To this end, the oligonucleotide can be conjugated to another molecule, (e.g., a peptide, hybridization triggered cross-linking agent, transport agent, or hybridization-triggered cleavage agent).

III. Isolated B7-4 or PD-1 Proteins and Anti-B7-4 or PD-1 Antibodies

In addition, isolated B7-4 or PD-1 proteins, and biologically active portions thereof, as well as anti-B7-4 or PD-1 antibodies can be used as modulating agents. In one embodiment, native B7-4 or PD-1 proteins can be isolated from cells or tissue sources by an appropriate purification scheme using standard protein purification techniques. In another embodiment, B7-4 or PD-1 proteins are produced by recombinant DNA techniques. Alternative to recombinant expression, a B7-4 or PD-1 protein or polypeptide can be synthesized chemically using standard peptide synthesis techniques.

Another aspect of the invention pertains to isolated B7-4 or PD-1 proteins. Preferably, the B7-4 or PD-1 proteins comprise the amino acid sequence encoded by SEQ ID NO:1, 3, 10 or 11. In another preferred embodiment, the protein comprises the amino acid sequence of SEQ ID NO:2, 4, or 12. In other embodiments, the protein has at least 50%, at least 60% amino acid identity, more preferably 70% amino acid identity, more preferably 80%, and even more preferably, 90% or 95% amino acid identity with the amino acid sequence shown in SEQ ID NO:2, 4, or 12.

In other embodiments, the invention provides isolated portions of a B7-4 or PD-1 protein. For example, B7-4 proteins comprise a signal sequence, and an IgV domain and an IgC domain. The signal sequence of SEQ ID NO:2 is shown from about amino acid 1 to about amino acid 18. The signal sequence of SEQ ID NO:4 is shown from about amino acid 1 to about amino acid 18. The IgV domain of SEQ ID NO:2 is shown from about amino acid 19 to about amino acid 134 and the IgV domain of SEQ ID NO:4 is shown from about amino acid 19 to about amino acid 134. The IgC domain of SEQ ID NO:2 is shown from about amino acid 135 to about amino acid 227 and the IgC domain of SEQ ID NO:4 is shown from about amino acid 135 to about amino acid 227. The B7-4 molecule exemplified in SEQ ID NO:2 comprises a hydrophilic tail shown from about amino acid 228 to about amino acid 245. The B7-4 polypeptide exemplified in SEQ ID NO:4 comprises a transmembrane domain shown from about amino acid 239 to about amino acid 259 of SEQ ID NO:4 and a cytoplasmic domain shown from about amino acid 260 to about amino acid 290 of SEQ ID NO:4. The PD-1 polypeptide is 288 amino acids in length and its domain structure is known in the art (Shinohara et al. (1994) *Genomics* 23:704). The predicted mature form of the protein contains about 268 amino acids and comprises an extracellular domain (147 amino acids), a transmembrane domain (27 amino acids), a transmembrane region (27 amino acids) and a cytoplasmic domain (94 amino acids). Four potential N-glycosylation sites are found in the extracellular domain (U.S. Pat. No. 5,698,520). The 68 amino acid residues between two cysteine residues (cys 54 and cys 123) bear resemblance to a disulfide-linked immunoglobulin domain of the V-set sequences (U.S. Pat. No. 5,698,520).

The invention further pertains to soluble forms of B7-4 or PD-1 proteins. Such forms can be naturally occurring, e.g., as shown in SEQ ID NO:2 or can be engineered and can comprise, e.g., an extracellular domain of a B7-4 or PD-1 protein. Exemplary B7-4 extracellular domains comprise from about amino acids 19–238 of SEQ ID NO:4. Exemplary PD-1 extracellular domains comprise from about amino acids 21–288 of SEQ ID NO:12.

In one embodiment, the extracellular domain of a B7-4 polypeptide comprises the mature form of a B7-4 polypeptide, e.g., the IgV and IgC domains, but not the transmembrane and cytoplasmic domains of a B7-4 polypeptide (e.g., from about amino acid 19 to amino acid 238 of SEQ ID NO:4) or from about amino acid 19 to amino acid 245 of SEQ ID NO:2.

In one embodiment, the extracellular domain of a PD-1 polypeptide comprises the mature form of a PD-1 polypeptide, e.g., immunoglobulin superfamily domains (e.g., V-set sequences), but not the transmembrane and cytoplasmic domains of a PD-1 polypeptide (e.g., from about amino acid 21–288 of SEQ ID NO:12).

Biologically active portions of a B7-4 or PD-1 protein include peptides comprising amino acid sequences sufficiently homologous to or derived from the amino acid sequence of the B7-4 or PD-1 protein, which include fewer amino acids than the full length B7-4 or PD-1 proteins, and exhibit at least one activity of a B7-4 or PD-1 protein, preferably the ability to bind to a natural binding partner. Typically, biologically active portions comprise a domain or motif with at least one activity of the B7-4 or PD-1 protein. A biologically active portion of a B7-4 or PD-1 protein can be a polypeptide which is, for example, at least 10, 25, 50, 100, 150, 200 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues or nucleic acids at corresponding positions are then compared and when a position in one sequence is occupied by the same residue or nucleic acid as the corresponding position in the other sequence, then the molecules are identical at that position. The percent identity between two sequences, therefore, is a function of the number of identical positions shared by two sequences (i.e., % identity=# of identical positions/total # of positions× 100). The percent identity between the two sequences is a function of the number of identical positions shared by the sequences, taking into account the number of gaps, and the length of each gap, which need to be introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. In a preferred embodiment, the percent identity between two amino acid sequences is determined using the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to B7-4 or PD-1 nucleic acid molecules of the invention. BLAST protein searches can be performed with the XBLAST program, score=50, wordlength=3 to obtain amino acid sequences homologous to B7-4 or PD-1 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. For example, the nucleotide sequences of the invention were analyzed using the default Blastn matrix 1–3 with gap penalties set at: existence 11 and extension 1. The amino acid sequences of the invention were analyzed using the default settings: the Blosum 62 matrix with gap penalties set at existence 11 and extension 1. (See, e.g., the NCBI web page).

The invention also provides B7-4 or PD-1 chimeric or fusion proteins. As used herein, a B7-4 or PD-1 "chimeric protein" or "fusion protein" comprises a B7-4 or PD-1 polypeptide operatively linked to a non-B7-4 or PD-1 polypeptide. A "B7-4 or PD-1 polypeptide" refers to a polypeptide having an amino acid sequence corresponding to B7-4 or PD-1 polypeptide, whereas a "non-B7-4 or PD-1 polypeptide" refers to a polypeptide having an amino acid sequence corresponding to a protein which is not substantially homologous to the B7-4 or PD-1 protein, e.g., a protein which is different from the B7-4 or PD-1 protein and which is derived from the same or a different organism. Within a B7-4 or PD-1 fusion protein the B7-4 or PD-1 polypeptide can correspond to all or a portion of a B7-4 or PD-1 protein. In a preferred embodiment, a B7-4 or PD-1 fusion protein comprises at least one biologically active portion of a B7-4 or PD-1 protein, e.g., an extracellular domain of a B7-4 or PD-1 protein. Within the fusion protein, the term "operatively linked" is intended to indicate that the B7-4 or PD-1 polypeptide and the non-B7-4 or PD-1 polypeptide are fused in-frame to each other. The non-B7-4 or PD-1 polypeptide can be fused to the N-terminus or C-terminus of the B7-4 or PD-1 polypeptide.

For example, in one embodiment, the fusion protein is a GST-B7-4 or GST-PD-1 fusion protein in which the B7-4 or PD-1 sequences are fused to the C-terminus of the GST sequences. In another embodiment, the fusion protein is a B7-4 or PD-1-HA fusion protein in which the B7-4 or PD-1 nucleotide sequence is inserted in a vector such as pCEP4-HA vector (Herrscher, R. F. et al. (1995) Genes Dev. 9:3067–3082) such that the B7-4 or PD-1 sequences are fused in frame to an influenza hemagglutinin epitope tag. Such fusion proteins can facilitate the purification of a recombinant B7-4 or PD-1 protein.

A B7-4 or PD-1 fusion protein can be produced by recombinant expression of a nucleotide sequence encoding a first peptide having B7-4 activity, and a nucleotide sequence encoding a second peptide corresponding to a moiety that alters the solubility, affinity, stability or valency of the first peptide, for example, an immunoglobulin constant region. Preferably, the first peptide consists of a portion of the B7-4 polypeptide (e.g., a portion of amino acid residues 1–238 or 19–238 (after cleavage of the signal sequence) of the sequence shown in SEQ ID NO:4 that is sufficient to modulate costimulation or inhibition of activated immune cells). In another preferred embodiment, the first peptide consists of a portion of a PD-1 polypeptide (e.g., a portion of amino acid residues 1–288 (or 21–288 after cleavage of the signal peptide) of the sequence shown in SEQ ID NO:12 that is sufficient to modulate costimulation or inhibition of activated immune cells). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). A resulting fusion protein may have altered B7-4 or PD-1 solubility, binding affinity, stability and/or valency (i.e., the number of binding sites available per molecule) and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Particularly preferred B7-4 or PD-1 Ig fusion proteins include the extracellular domain portion or variable region-like domain of a human B7-4 or PD-1 coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a B7-4 or PD-1 polypeptide can be joined to DNA encoding the hinge, CH2 and CH3 regions of human IgGγ1 and/or IgGγ4 modified by site directed mutagenesis, e.g., as taught in WO 97/28267. Fusion proteins of, e.g., B7-4 and an immunoglobulin fusion protein may be referred to interchangeably herein as "B7-4.Ig" or "B7-4.Fc". Other variations which incorporate the terms "Ig" or "Fc" may also be used.

Preferably, a B7-4 or PD-1 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A B7-4 or PD-1 encoding nucleic acid can be cloned into such an expression vector such that the fusion moiety is linked in-frame to the B7-4 or PD-1 protein.

In another embodiment, the fusion protein is a B7-4 or PD-1 protein containing a heterologous signal sequence at its N-terminus. In certain host cells (e.g., mammalian host cells), expression and/or secretion of B7-4 or PD-1 can be increased through use of a heterologous signal sequence.

The B7-4 or PD-1 fusion proteins of the invention can be incorporated into pharmaceutical compositions and administered to a subject in vivo. Use of B7-4 or PD-1 fusion proteins is useful for therapeutic modulation of an immune response to, for instance, treatment of immunological disorders, e.g., autoimmune diseases, or in the case of inhibiting rejection of transplants. Moreover, the B7-4 or PD-1-fusion proteins of the invention, (e.g., full length protein or portions thereof) can be used as immunogens to produce anti-B7-4 or PD-1 antibodies in a subject, to purify B7-4 or PD-1 and in screening assays to identify molecules which inhibit the interaction of B7-4 with a B7-4 receptor, e.g., PD-1.

Preferably, a B7-4 or PD-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of nucleic acid (e.g., gene) fragments can be carried out using anchor primers which give rise to complementary overhangs between two consecutive nucleic acid fragments which can subsequently be annealed and reamplified to generate a chimeric nucleic acid sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A B7-4 or PD-1-encoding nucleic acid can be cloned into such an expression vector such that the fusion moiety is linked in-frame to the B7-4 or PD-1 protein.

The present invention also pertains to variants of the B7-4 or PD-1 proteins which function as either B7-4 or PD-1 agonists (mimetics) or as B7-4 or PD-1 antagonists. Variants of the B7-4 or PD-1 proteins can be generated by mutagenesis, e.g., discrete point mutation or truncation of a B7-4 or PD-1 protein. An agonist of the B7-4 or PD-1 proteins can retain substantially the same, or a subset, of the biological activities of the naturally occurring form of a B7-4 or PD-1 protein. An antagonist of a B7-4 or PD-1 protein can inhibit one or more of the activities of the naturally occurring form of the B7-4 or PD-1 protein by, for example, competitively modulating a cellular activity of a B7-4 or PD-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the B7-4 or PD-1 protein.

In one embodiment, variants of a B7-4 or PD-1 protein which function as either B7-4 or PD-1 agonists (mimetics) or as B7-4 or PD-1 antagonists can be identified by screening combinatorial libraries of mutants, e.g., point mutants or truncation mutants, of a B7-4 or PD-1 protein for B7-4 or PD-1 protein agonist or antagonist activity. In one embodiment, a variegated library of B7-4 or PD-1 variants is generated by combinatorial mutagenesis at the nucleic acid level and is encoded by a variegated gene library. A variegated library of B7-4 or PD-1 variants can be produced by, for example, enzymatically ligating a mixture of synthetic oligonucleotides into gene sequences such that a degenerate set of potential B7-4 or PD-1 sequences is expressible as individual polypeptides, or alternatively, as a set of larger fusion proteins (e.g., for phage display) containing the set of B7-4 or PD-1 sequences therein. There are a variety of methods which can be used to produce libraries of potential B7-4 or PD-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential B7-4 or PD-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477.

In addition, libraries of fragments of a B7-4 or PD-1 protein coding sequence can be used to generate a variegated population of B7-4 or PD-1 fragments for screening and subsequent selection of variants of a B7-4 or PD-1 protein. In one embodiment, a library of coding sequence fragments can be generated by treating a double stranded PCR fragment of a B7-4 or PD-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the B7-4 or PD-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of B7-4 or PD-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify B7-4 or PD-1 variants (Arkin and Youvan (1992) *Proc. Natl. Acad. Sci. USA* 89:7811–7815; Delagrave et al. (1993) *Protein Eng.* 6(3):327–331).

In one embodiment, cell based assays can be exploited to analyze a variegated B7-4 or PD-1 library. For example, a library of expression vectors can be transfected into a cell line which ordinarily synthesizes and secretes B7-4 or PD-1. The transfected cells are then cultured such that B7-4 or PD-1 and a particular mutant B7-4 or PD-1 are secreted and the effect of expression of the mutant on B7-4 or PD-1 activity in cell supernatants can be detected, e.g., by any of a number of functional assays. Plasmid DNA can then be recovered from the cells which score for inhibition, or alternatively, potentiation of B7-4 or PD-1 activity, and the individual clones further characterized.

In addition to B7-4 or PD-1 polypeptides consisting only of naturally-occurring amino acids, B7-4 or PD-1 peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15:29; Veber and Freidinger (1985) TINS p.392; and Evans et al. (1987) *J. Med. Chem.* 30:1229, which are incorporated herein by reference) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human B7-4 or PD-1, but have one or more peptide linkages optionally replaced by a linkage selected from the group consisting of: —CH2NH—, —CH2S—, —CH2—CH2—, —CH=CH— (cis and trans), —COCH2—, —CH(OH)CH2—, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463–468 (general review); Hudson, D. et al. (1979) *Int. J. Pept. Prot. Res.* 14:177–185 (—CH2NH—, CH2CH2—); Spatola, A. F. et al. (1986) *Life Sci.* 38:1243–1249 (—CH2—S); Hann, M. M. (1982) *J. Chem. Soc. Perkin Trans. I.* 307–314 (—CH—

CH—, cis and trans); Almquist, R. G. et al. (190) *J. Med. Chem.* 23:1392–1398 (—COCH2—); Jennings-White, C. et al. (1982) *Tetrahedron Lett.* 23:2533 (—COCH2—); Szelke, M. et al. European Appln. EP 45665 (1982) CA: 97:39405 (1982)(—CH(OH)CH2—); Holladay, M. W. et al. (1983) *Tetrahedron Lett.* (1983) 24:4401–4404 (—C(OH)CH2—); and Hruby, V. J. (1982) *Life Sci.* (1982) 31:189–199 (—CH2—S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of a B7-4 or PD-1 amino acid sequence with a D-amino acid of the same type (e.g., D-lysine in place of L-lysine) can be used to generate more stable peptides. In addition, constrained peptides comprising a B7-4 or PD-1 amino acid sequence or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences of B7-4 or PD-1 polypeptides identified herein will enable those of skill in the art to produce polypeptides corresponding to B7-4 or PD-1 peptide sequences and sequence variants thereof. Such polypeptides can be produced in prokaryotic or eukaryotic host cells by expression of polynucleotides encoding a B7-4 or PD-1 peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis el al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis, and used e.g., as agonists or antagonists of a B7-4/PD-1 interaction. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

An isolated B7-4 or PD-1 protein, or a portion or fragment thereof (or a nucleic acid molecule encoding such a polypeptide), can be used as an immunogen to generate antibodies that bind B7-4 or PD-1 using standard techniques for polyclonal and monoclonal antibody preparation. A full-length B7-4 or PD-1 protein can be used, or alternatively, the invention provides antigenic peptide fragments of B7-4 or PD-1 for use as immunogens. The antigenic peptide of B7-4 or PD-1 comprises at least 8 amino acid residues and encompasses an epitope of B7-4 or PD-1 such that an antibody raised against the peptide forms a specific immune complex with B7-4 or PD-1. Preferably, the antigenic peptide comprises at least 10 amino acid residues, more preferably at least 15 amino acid residues, even more preferably at least 20 amino acid residues, and most preferably at least 30 amino acid residues.

Alternatively, an antigenic peptide fragment of a B7-4 or PD-1 polypeptide can be used as the immunogen. An antigenic peptide fragment of a B7-4 or PD-1 polypeptide typically comprises at least 8 amino acid residues of the amino acid sequence shown in SEQ ID NO:2, 4, or 12 and encompasses an epitope of a B7-4 or PD-1 polypeptide such that an antibody raised against the peptide forms an immune complex with a B7-4 or PD-1 molecule. Preferred epitopes encompassed by the antigenic peptide are regions of B7-4 or PD-1 that are located on the surface of the protein, e.g., hydrophilic regions. In one embodiment, an antibody binds substantially specifically to a molecule which contains a portion of a B7-4 or PD-1 molecule (e.g., the extracellular portion). In another embodiment, an antibody binds specifically to a B7-4 or PD-1 polypeptide.

Preferably, the antigenic peptide comprises at least about 10 amino acid residues, more preferably at least about 15 amino acid residues, even more preferably at least about 20 amino acid residues, and most preferably at least about 30 amino acid residues. Preferred epitopes encompassed by the antigenic peptide are regions of a B7-4 or PD-1 polypeptide that are located on the surface of the protein, e.g., hydrophilic regions, and that are unique to a B7-4 or PD-1 polypeptide. In one embodiment such epitopes can be specific for a B7-4 or PD-1 protein from one species, such as mouse or human (i.e., an antigenic peptide that spans a region of a B7-4 or PD-1 polypeptide that is not conserved across species is used as immunogen; such non conserved residues can be determined using an alignment such as that provided herein). A standard hydrophobicity analysis of the B7-4 or PD-1 protein can be performed to identify hydrophilic regions.

A B7-4 or PD-1 immunogen typically is used to prepare antibodies by immunizing a suitable subject, (e.g., rabbit, goat, mouse or other mammal) with the immunogen. An appropriate immunogenic preparation can contain, for example, a recombinantly expressed B7-4 or PD-1 protein or peptide fragment, or a chemically synthesized B7-4 or PD-1 peptide fragment. The preparation can further include an adjuvant, such as Freund's complete or incomplete adjuvant, or similar immunostimulatory agent. Immunization of a suitable subject with an immunogenic B7-4 or PD-1 preparation induces a polyclonal anti- B7-4 or PD-1 antibody response.

In another embodiment, nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) *J. Biotechnol.* 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert (1997) *Proc. Natl. Acad. Sci. USA* 94:961). Attenuated microorganisms can be used for delivery to mucosal surfaces (Sizemore et al. (1995) *Science* 270:29).

Yet another aspect of the invention pertains to anti-B7-4 or PD-1 antibodies. Such antibodies are, for instance, generated by immunizing an animal with an immunogenic B7-4 or PD-1 protein, or an immunogenic portion thereof which is unique to a B7-4 or PD-1 polypeptide, and then isolating antibodies from the animal that specifically bind to the B7-4 or PD-1 protein, or a fragment thereof.

Polyclonal anti-B7-4 or PD-1 antibodies can be prepared as described above by immunizing a suitable subject with a B7-4 or PD-1 immunogen. The anti-B7-4 or PD-1 antibody titer in the immunized subject can be monitored over time by standard techniques, such as with an enzyme linked immunosorbent assay (ELISA) using immobilized a B7-4 or PD-1 polypeptide. If desired, the antibody molecules directed against a B7-4 or PD-1 polypeptide can be isolated from the mammal (e.g., from the blood) and further purified by well known techniques, such as protein A chromatography to obtain the IgG fraction. At an appropriate time after immunization, e.g., when the anti- B7-4 or PD-1 antibody titers are highest, antibody-producing cells can be obtained from the subject and used to prepare monoclonal antibodies by standard techniques, such as the hybridoma technique originally described by Kohler and Milstein (1975) *Nature* 256: 495–497) (see also Brown et al. (1981) *J. Immunol.* 127: 539–46; Brown et al. (1980) *J. Biol. Chem.* 255:4980–83; Yeh et al. (1976) *Proc. Natl. Acad. Sci.* 76:2927–31; and Yeh et al. (1982) *Int. J. Cancer* 29:269–75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a B7-4 or PD-1 immunogen as described above, and the culture supernatants of the resulting hybridoma cells are screened to identify a hybridoma producing a monoclonal antibody that binds to a B7-4 or PD-1 polypeptide, preferably specifically.

Any of the many well known protocols used for fusing lymphocytes and immortalized cell lines can be applied for the purpose of generating an anti-B7-4 or PD-1 monoclonal antibody (see, e.g., Galfre, G. et al. (1977) *Nature* 266: 55052; Gefter et al (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4–1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a B7-4 or PD-1 molecule, e.g., using a standard ELISA assay.

As an alternative to preparing monoclonal antibody-secreting hybridomas, a monoclonal anti-B7-4 or PD-1 antibody can be identified and isolated by screening a recombinant combinatorial immunoglobulin library (e.g., an antibody phage display library) with a B7-4 or PD-1 to thereby isolate immunoglobulin library members that bind a B7-4 or PD-1 polypeptide. Kits for generating and screening phage display libraries are commercially available (e.g, the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrard et al. (1991) *Biotechnology* (NY) 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-B7-4 or PD-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139: 3521–3526; Sun et al. (1987) *Proc. Natl. Acad. Sci.* 84:214–218; Nishimura et al. (1987) *Cancer Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *Biotechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable genetic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Lett.* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Biotechnology* (NY) 12:396–399; Chen, S-Y. et al. (1994) *Hum. Gene Ther.* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204: 666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

In one embodiment, an antibody for use in the instant invention is a bispecific antibody. A bispecific antibody has binding sites for two different antigens within a single antibody molecule. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to PD-1 or B7-4.

An anti-B7-4 or PD-1 antibody (e.g., monoclonal antibody) can be used to isolate a B7-4 or PD-1 polypeptide by standard techniques, such as affinity chromatography or immunoprecipitation. Anti-B7-4 or PD-1 antibodies can facilitate the purification of natural B7-4 or PD-1 polypeptides from cells and of recombinantly produced B7-4 or PD-1 polypeptides expressed in host cells. Moreover, an anti-B7-4 or PD-1 antibody can be used to detect a B7-4 or PD-1 protein (e.g., in a cellular lysate or cell supernatant). Detection can be facilitated by coupling (i.e., physically linking) the antibody to a detectable substance. Accordingly, in one embodiment, an anti-B7-4 or PD-1 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$, and $^{3}H$.

IV. Recombinant Expression Vectors and Host Cells

Nucleic acid molecules encoding a B7-4 or PD-1 family protein (or a portion thereof) can be contained in vectors, preferably expression vectors. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Recombinant expression vectors can comprise a nucleic acid molecule of the invention in a form suitable for expression, e.g., constitutive or inducible expression, of a PD-1 or B7-4 molecule in the indicator cell(s) of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cell and those which direct expression of the nucleotide sequence only in certain host cells (e.g., tissue-specific regulatory sequences). It should be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., B7-4 or PD-1 family proteins, mutant forms of B7-4 or PD-1 proteins, fusion proteins, and the like).

The recombinant expression vectors of the invention can be designed for expression of B7-4 or PD-1 proteins in prokaryotic or eukaryotic cells. For example, B7-4 or PD-1 proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in B7-4 or PD-1 activity assays, (e.g., direct assays or competitive assays described in detail below), or to generate antibodies specific for B7-4 or PD-1 proteins, for example.

Examples of suitable inducible non-fusion *E. coli* expression vectors include pTrc (Amann et al., (1988) *Gene* 69:301–315) and pET 11d (Studier et al. (1990) *Methods Enzymol.* 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the B7-4 or PD-1 expression vector is a yeast expression vector. Examples of vectors for expression in yeast *S. cerevisiae* include pYepSec1 (Baldari, et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and picZ (Invitrogen Corp, San Diego, Calif.).

Alternatively, a B7-4 or PD-1 polypeptide can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow, V. A. and Summers, M. D. (1989) *Virology* 170:31–39).

In yet another embodiment, a nucleic acid of the invention is expressed in mammalian cells using a mammalian expression vector. Examples of mammalian expression vectors include pMex-NeoI, pCDM8 (Seed, B. (1987) *Nature* 329: 840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166).

Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, ed. Nouer, L., CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329: 734–736; Israel and Kaufman (1989) *Nucleic. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which a B7-4 or PD-1 DNA is operatively linked to an inducible eukaryotic promoter, thereby allowing for inducible expression of a B7-4 or PD-1 protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to B7-4 or PD-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al. (1986) "Antisense RNA as a molecular tool for genetic analysis" *Reviews—Trends in Genetics*, Vol. 1(1).

The invention further pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a B7-4 or PD-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a B7-4 or PD-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a B7-4 or PD-1 protein. Accordingly, the invention further provides methods for producing a B7-4 or PD-1 protein using the host cells of the invention. In one embodiment, the method comprises culturing the host cell (into which a recombinant expression vector encoding a B7-4 or PD-1 protein has been introduced) in a suitable medium such that a B7-4 or PD-1 protein is produced. In another embodiment, the method further comprises isolating a B7-4 or PD-1 protein from the medium or the host cell.

Certain host cells can also be used to produce non-human transgenic animals. For example, in one embodiment, a host cell is a fertilized oocyte or an embryonic stem cell into which B7-4 or PD-1-coding sequences have been introduced. Such host cells can then be used to create non-human transgenic animals in which exogenous B7-4 or PD-1 sequences have been introduced into their genome or homologous recombinant animals in which endogenous B7-4 or PD-1 sequences have been altered. Such animals are useful for studying the function and/or activity of a B7-4 or PD-1 polypeptide and for identifying and/or evaluating modulators of B7-4 or PD-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous B7-4 or PD-1 gene has been altered by homologous recombination between the endogenous gene and an exogenous DNA molecule introduced into a cell of the animal, e.g., an embryonic cell of the animal, prior to development of the animal.

A transgenic animal can be created by introducing a B7-4 or PD-1-encoding nucleic acid molecule into the male pronucleus of a fertilized oocyte, e.g., by microinjection, retroviral infection, and allowing the oocyte to develop in a pseudopregnant female foster animal. The B7-4 or PD-1 cDNA sequence of SEQ ID NO:1, 3, 10, or 11 can be introduced as a transgene into the genome of a non-human animal. Alternatively, a nonhuman homologue of a human B7-4 or PD-1 gene, such as a mouse or rat B7-4 or PD-1 gene, can be used as a transgene. Alternatively, a B7-4 or PD-1 gene homologue, such as another B7-4 or PD-1 family member, can be isolated based on hybridization to the B7-4 or PD-1 family cDNA sequences of SEQ ID NO: 1, 3, 10, or 11 (described further in subsection I above) and used as a transgene. Intronic sequences and polyadenylation signals can also be included in the transgene to increase the efficiency of expression of the transgene. A tissue-specific regulatory sequence(s) can be operably linked to a B7-4 or PD-1 transgene to direct expression of a B7-4 or PD-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B. *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of a B7-4 or PD-1 transgene in its genome and/or expression of B7-4 or PD-1 mRNA in tissues or cells of the animals. A transgenic founder animal can then be used to breed additional animals carrying the transgene. Moreover, transgenic animals carrying a transgene encoding a B7-4 or PD-1 protein can further be bred to other transgenic animals carrying other transgenes.

To create a homologous recombinant animal, a vector is prepared which contains at least a portion of a B7-4 or PD-1 gene into which a deletion, addition or substitution has been introduced to thereby alter, e.g., functionally disrupt, the B7-4 or PD-1 gene. The B7-4 or PD-1 gene can be a human gene (e.g., the SEQ ID NO:1, 3, 10, or 11), but more preferably, is a non-human homologue of a human B7-4 or PD-1 gene (e.g., a cDNA isolated by stringent hybridization with the nucleotide sequence of SEQ ID NO:1, 3, 10, or 11). For example, a mouse B7-4 or PD-1 gene can be used to construct a homologous recombination vector suitable for altering an endogenous B7-4 or PD-1 gene in the mouse genome. In a preferred embodiment, the vector is designed such that, upon homologous recombination, the endogenous B7-4 or PD-1 gene is functionally disrupted (i.e., no longer encodes a functional protein; also referred to as a "knock out" vector). Alternatively, the vector can be designed such that, upon homologous recombination, the endogenous B7-4 or PD-1 gene is mutated or otherwise altered but still encodes a functional protein (e.g., the upstream regulatory region can be altered to thereby alter the expression of the endogenous B7-4 or PD-1 protein). In the homologous recombination vector, the altered portion of the B7-4 or PD-1 gene is flanked at its 5' and 3' ends by additional nucleic acid sequence of the B7-4 or PD-1 gene to allow for homologous recombination to occur between the exogenous B7-4 or PD-1 gene carried by the vector and an endogenous B7-4 or PD-1 gene in an embryonic stem cell. The additional flanking B7-4 or PD-1 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced B7-4 or PD-1 gene has homologously recombined with the endogenous B7-4 or PD-1 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, Robertson, E. J., ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Curr. Opin. Biotechnol.* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucleic. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473). Tetracycline-regulated inducible homologous recombination systems, such as described in PCT Publication No. WO 94/29442 and PCT Publication No. WO 96/01313, also can be used.

For example, in another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. *(*1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Pharmaceutical Compositions

B7-4 or PD-1 modulators (e.g., B7-4 or PD-1 inhibitory or stimulatory agents, including B7-4 or PD-1 nucleic acid molecules, proteins, antibodies described above, or compounds identified as modulators of a B7-4 or PD-1 activity and/or expression or modulators of the interaction between B7-4 and PD-1) can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a B7-4 or PD-1 protein or anti-B7-4 or PD-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously-sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The B7-4 and/or PD-1 modulatory agents, e.g., the nucleic acid molecules, proteins, protein homologues, and antibodies described herein, can be used, for example, in one or more of the following methods: a) methods of treatment, e.g., by up- or down-modulating the immune response; b) screening assays; c) predictive medicine (e.g., diagnostic assays, prognostic assays, monitoring clinical trials, and pharmacogenetics). The isolated nucleic acid molecules of the invention can be used, for example, to express B7-4 or PD-1 protein (e.g., via a recombinant expression vector in a host cell in gene therapy applications), to detect B7-4 or PD-1 mRNA (e.g., in a biological sample) or a genetic alteration in a B7-4 or PD-1 gene, and to modulate B7-4 or PD-1 activity, as described further below. The B7-4 or PD-1 proteins can be used to treat disorders characterized by insufficient or excessive production of B7-4 or PD-1 inhibitors. In addition, the B7-4 or PD-1 proteins can be used to screen for naturally occurring B7-4 or PD-1 binding partners, to screen for drugs or compounds which modulate B7-4 or PD-1 activity, as well as to treat disorders characterized by insufficient or excessive production of B7-4 or PD-1 protein or production of B7-4 or PD-1 protein forms which have decreased or aberrant activity compared to B7-4 or PD-1 wild type protein. Moreover, the anti-B7-4 or PD-1 antibodies of the invention can be used to detect and isolate B7-4 or PD-1 proteins, regulate the bioavailability of B7-4 or PD-1 proteins, and modulate B7-4 or PD-1 activity e.g., by modulating the interaction of B7-4 and PD-1.

A. Methods of Treatment:

The present invention provides for both prophylactic and therapeutic methods of treating a subject at risk of (or susceptible to) a disorder or having a disorder associated with aberrant B7-4 or PD-1 expression or activity.

1. Prophylactic Methods

In one aspect, the invention provides a method for preventing in a subject, a disease or condition associated with an aberrant B7-4 or PD-1 expression or activity, by administering to the subject a B7-4 or PD-1 polypeptide or an agent which modulates B7-4 or PD-1 polypeptide expression or at least one B7-4 or PD-1 activity. Subjects at risk for a disease which is caused or contributed to by aberrant B7-4 or PD-1 expression or activity can be identified by, for example, any or a combination of diagnostic or prognostic assays as described herein. Administration of a prophylactic agent can occur prior to the manifestation of symptoms characteristic of B7-4 or PD-1 aberrancy, such that a disease or disorder is prevented or, alternatively, delayed in its progression. Depending on the type of B7-4 or PD-1 aberrancy or condition, for example, a B7-4 or PD-1 polypeptide, B7-4 or PD-1 agonist or B7-4 or PD-1 antagonist agent can be used for treating the subject. The appropriate agent can be determined based on clinical indications and can be identified, e.g., using screening assays described herein.

2. Therapeutic Methods

Another aspect of the invention pertains to methods of modulating B7-4 or PD-1 expression or activity for therapeutic purposes. B7-4 has been demonstrated to inhibit the costimulation and proliferation of activated immune cells and to transmit an inhibitory signal to immune cells via PD-1. Accordingly, the activity and/or expression of B7-4 or PD-1 as well as the interaction between B7-4 and PD-1 can be modulated in order to modulate the immune response. It should be understood that in embodiments where B7-4 binds to a costimulatory receptor, upregulation of B7-4 activity results in upregulation of immune responses, whereas downregulation of B7-4 activity results in downregulation of immune responses. In embodiments where B7-4 binds to inhibitory receptors, upregulation of B7-4 activity results in downregulation of immune responses, whereas downregulation of B7-4 activity results in upregulation of immune responses. In a preferred embodiment, B7-4 binds to inhibitory receptors. In a particularly preferred embodiment, B7-4 binds to PD-1.

Modulatory methods of the invention involve contacting a cell with a modulator of a B7-4 or a PD-1 polypeptide, e.g., an agent that modulates expression or activity of B7-4 and/or PD-1, or an agent that modulates the interaction of B7-4 and PD-1.

An agent that modulates B7-4 or PD-1 protein activity is an agent as described herein, such as a nucleic acid or a a protein molecule, a naturally-occurring target molecule of a B7-4 or PD-1 protein (e.g., PD-1 in the case of B7-4 or B7-4 in the case of PD-1), a B7-4 or PD-1 antibody, a B7-4 or PD-1 agonist or antagonist, a peptidomimetic of a B7-4 or PD-1 agonist or antagonist, or other small molecule.

An agent that modulates the expression of B7-4 or PD-1 is, e.g., an antisense nucleic acid molecule, triplex oligonucleotide, a ribozyme, or a recombinant vector for expression of a B7-4 or PD-1 protein. For example, an oligonucleotide complementary to the area around a B7-4 or PD-1 polypeptide translation initiation site, can be synthesized and used. One or more antisense oligonucleotides can be added to cell media, typically at 200 µg/ml, or administered to a patient to prevent the synthesis of a B7-4 or PD-1 polypeptide. The antisense oligonucleotide is taken up by cells and hybridizes to a B7-4 or PD-1 mRNA to prevent translation. Alternatively, an oligonucleotide which binds double-stranded DNA to form a triplex construct to prevent DNA unwinding and transcription can be used. As a result of either, synthesis of a B7-4 or PD-1 polypeptide is blocked. When PD-1 expression is modulated, preferably, such modulation occurs by a means other than by knocking out the PD-1 gene.

Agents which modulate expression, by virtue of the fact that they control the amount of PD-1 or B7-4 in a cell, also modulate the total amount of PD-1 or B7-4 activity in a cell.

In one embodiment, an agent that stimulates an inhibitory activity of B7-4 or an inhibitory activity of PD-1 is an agonist of B7-4 or PD-1. Examples of such agents include active B7-4 or PD-1 protein and an expressible nucleic acid molecule encoding B7-4 or PD-1 polypeptide that has been introduced into the cell.

In another embodiment, the agent inhibits the costimulatory or inhibitory activity of B7-4 or inhibitory activity of PD-1 and is an antagonist of B7-4 or PD-1. Examples of such agents include antisense B7-4 or PD-1 nucleic acid molecules, anti-B7-4 or PD-1 antibodies (e.g., non-activating antibodies), soluble, nonactivating forms of B7-4 or PD-1 molecules, and B7-4 or PD-1 inhibitors.

These modulatory agents can be administered in vitro (e.g., by contacting the cell with the agent) or, alternatively, in vivo (e.g., by administering the agent to a subject). As such, the present invention provides methods of treating an individual afflicted with a disease or disorder that would benefit from modulation of a B7-4 or PD-1 protein, e.g., a disorder which would benefit from up or downmodulation of the immune response, or which is characterized by aberrant expression or activity of a B7-4 or PD-1 protein or nucleic acid molecule. In one embodiment, the method involves administering an agent (e.g., an agent identified by a screening assay described herein), or combination of agents that modulates (e.g., upregulates or downregulates) B7-4 or PD-1 expression or activity. In another embodiment, the method involves administering a B7-4 or PD-1 protein or nucleic acid molecule as therapy to compensate for reduced or aberrant B7-4 or PD-1 expression or activity.

Stimulation of B7-4 or PD-1 activity is desirable in situations in which B7-4 or PD-1 is abnormally downregulated and/or in which increased B7-4 or PD-1 activity is likely to have a beneficial effect. Likewise, inhibition of B7-4 or PD-1 activity is desirable in situations in which B7-4 or PD-1 is abnormally upregulated and/or in which decreased B7-4 or PD-1 activity is likely to have a beneficial effect. One of ordinary skill in the art should recognize that in embodiments where B7-4 binds to a costimulatory receptor, stimulation of B7-4 and stimulation of PD-1 have opposite effects on immune cell costimulation, and therefore, on the immune response. In such an instance, when stimulation of the activity of one molecule is desirable, suppression of the activity of the other molecule is desirable.

Exemplary agents for use in downmodulating B7-4 activity (B7-4 antagonists) include (for example): antisense molecules, antibodies that recognize B7-4, compounds that block interaction of B7-4 and one of its naturally occurring receptors on a immune cell (e.g., soluble, monovalent B7-4 molecules, and soluble forms of B7-4 ligands or compounds identified in the screening assays described herein). Exemplary agents for use in downmodulating PD-1 (PD-1 antagonists) include (for example): antisense molecules, antibodies that bind to PD-1, but do not transduce an inhibitory signal to the immune cell ("non-activating antibodies"), and soluble forms of PD-1.

Exemplary agents for use in upmodulating B7-4 activity (B7-4 agonists) include (for example): nucleic acid molecules encoding B7-4 polypeptides, multivalent forms of B7-4, compounds that increase the expression of B7-4, and cells that express B7-4, etc. Exemplary agents for use in upmodulating PD-1 (PD-1 agonists) include (for example): antibodies that transmit an inhibitory signal via PD-1 by binding to and activating (e.g., crosslinking) the PD-1 molecule, compounds that enhance the expression of PD-1, nucleic acid molecules encoding PD-1, and forms of B7-4 that transduce a signal via PD-1 (especially bivalent forms of B7-4).

3. Downregulation of Immune Responses by Modulation of B7-4 or PD-1

There are numerous embodiments of the invention for upregulating the inhibitory function or downregulating the costimulatory function of a B7-4 polypeptide to thereby downregulate immune responses. Downregulation can be in the form of inhibiting or blocking an immune response already in progress or may involve preventing the induction of an immune response.

The functions of activated immune cells can be inhibited by down-regulating immune cell responses or by inducing specific anergy in immune cells, or both.

For example, anti-B7-4 antibodies or B7-4 polypeptides (e.g., soluble, monomeric forms of a B7-4 polypeptide such as B7-4-Jg), and/or anti-B7-4 antibodies that block the interaction of B7-4 with a costimulatory receptor can be used to inhibit a costimulatory signal and, thus, downmodulate the immune response.

In addition, in embodiments where B7-4 binds to an inhibitory receptor, forms of B7-4 that bind to the inhibitory receptor and activate it, e.g., multivalent B7-4 on a cell surface, can be used to downmodulate the immune response.

Likewise, the PD-1 pathway can also be stimulated by the use of an agent to thereby downmodulate the immune response. This is accomplished via inhibition of the interaction of B7-4 with a stimulatory receptor on an immune cell (e.g., by using a soluble form of PD-1 and/or CTLA4) or activation of PD-1 (e.g., using an activating antibody which cross-links PD-1) to provide negative signals to immune cells.

In one embodiment of the invention, an activating antibody used to stimulate PD-1 activity is a bispecific antibody. For example, such an antibody can comprise a PD-1 binding site and another binding site which targets a cell surface receptor on an immune cell, e.g., on a T cell, a B cell, or a myeloid cell. In one embodiment, such an antibody, in addition to comprising a PD-1 binding site can further comprise a binding site which binds to a molecule which is in proximity to an activating or inhibitory receptor, e.g., B-cell antigen receptor, a T-cell antigen receptor, or an Fc receptor in order to target the molecule to a specific cell population. For example, a CD3 antigen, a T-cell receptor chain, LFA-1, CD2, CTLA-4, immunoglobulin, B cell receptor, Ig alpha, Ig beta, CD22, or Fc receptor could be used. Such antibodies (or other bispecific agents) are art recognized and can be produced, e.g., as described herein. Selection of this second antigen for the bispecific antibody provides flexibility in selection of cell population to be targeted for inhibition.

In another embodiment, the co-ligation of PD-1 and an activating or inhibitory receptor on a cell can enhance the generation of a negative signal via PD-1. Such co-ligation can be accomplished e.g., by use of a bispecific agent, e.g., a bispecific antibody as described herein having specificity for both PD-1 and a molecule associated with a receptor. In another embodiment, the use of a multivalent form of an agent that transmits a negative signal via PD-1 can be used to enhance the transmission of a negative signal via PD-1, e.g., an agent presented on a bead or on a surface. In another embodiment, such a multivalent agent can comprise two specificities to achieve co-ligation of PD-1 and a receptor or a receptor associated molecule (e.g., a bead comprising anti CD3 and B7-4).

Agents that block or inhibit interaction of B7-4 with a costimulatory receptor (e.g., soluble forms of B7-4 or blocking antibodies to B7-4) as well as agents that promote a B7-4-mediated inhibitory signal or agonists of PD-1 which activate PD-1 (e.g., PD-1 activating antibodies or PD-1 activating small molecules) can be identified by their ability to inhibit immune cell proliferation and/or effector function or to induce anergy when added to an in vitro assay. For example, cells can be cultured in the presence of an agent that stimulates signal transduction via an activating receptor. A number of art recognized readouts of cell activation can be employed to measure the inhibition, e.g., cell proliferation or effector function (e.g., antibody production, cytokine production, phagocytosis) in the presence of the activating agent. The ability of a test agent to block this activation can be readily determined by measuring the ability of the agent to affect a decrease in proliferation or effector function being measured.

In one embodiment of the invention, tolerance is induced against specific antigens by co-administering an antigen with a PD-1 agonist. For example, tolerance can be induced to specific proteins. In one embodiment, immune responses to allergens or foreign proteins to which an immune response is undesirable can be inhibited. For example, patients that receive Factor VIII frequently generate antibodies against this clotting factor. Co-administration of an agent that blocks a B7-4-mediated costimulatory signal or an agent that stimulates a PD-1 mediated inhibitory signal in combination with recombinant factor VIII (or physically linked to Factor VIII, e.g., by cross-linking) can result in downmodulation.

In one embodiment, fusion proteins comprising a B7-4 first peptide fused to a second peptide having an activity of another B lymphocyte antigen (e.g., B7-1 or B7–2), can be used to block interaction of B7-4 with a costimulatory receptor on a immune cell to downmodulate immune responses. Alternatively, two separate peptides (for example, a B7-4 polypeptide with B7-2 and/or B7-1), or a combination of blocking antibodies (e.g., antibodies against a B7-4 polypeptide with anti-B7-2 and/or anti-B7-1 monoclonal antibodies) can be combined as a single composition or administered separately (simultaneously or sequentially) to downregulate immune cell mediated immune responses in a subject. Furthermore, a therapeutically active amount of one or more peptides having a B7-4 polypeptide activity, with B7-1 and/or B7-2 activity can be used in conjunction with other downmodulating reagents to influence immune responses. Examples of other immunomodulating reagents include antibodies that block a costimulatory signal, (e.g., against CD28, ICOS), antibodies that activate an inhibitory signal via CTLA4, and/or antibodies against other immune cell markers (e.g., against CD40, against CD40 ligand, or against cytokines), fusion proteins (e.g., CTLA4-Fc, PD-1-Fc), and immunosuppressive drugs, (e.g., rapamycin, cyclosporine A or FK506).

The B7-4 and/or PD-1 peptides may also be useful in the construction of therapeutic agents which block immune cell function by destruction of cells. For example, portions of a B7-4 or PD-1 polypeptide can be linked to a toxin to make a cytotoxic agent capable of triggering the destruction of cells to which it binds.

For making cytotoxic agents, polypeptides of the invention may be linked, or operatively attached, to toxins using techniques that are known in the art, e.g., crosslinking or via recombinant DNA techniques. The preparation of immunotoxins is, in general, well known in the art (see, e.g., U.S. Pat. No. 4,340,535, and EP 44167, both incorporated herein by reference). Numerous types of disulfide-bond containing linkers are known which can successfully be employed to conjugate the toxin moiety with a polypeptide. In one embodiment, linkers that contain a disulfide bond that is sterically "hindered" are to be preferred, due to their greater stability in vivo, thus preventing release of the toxin moiety prior to binding at the site of action.

A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, alpha.-sarcin, aspergillin, restrictocin, ribonucleases such as placental ribonuclease, angiogenic, diphtheria toxin, and pseudomonas exotoxin, etc. A preferred toxin moiety for use in connection with the invention is toxin A chain which has been treated to modify or remove carbohydrate residues, deglycosylated A chain. (U.S. Pat. No. 5,776,427).

Infusion of one or a combination of such cytotoxic agents, (e.g., B7-4 ricin (alone or in combination with B7-2-ricin or B7-1-ricin), into a patient may result in the death of immune cells, particularly in light of the fact that activated immune cells that express higher amounts of B7-4 ligands. For example, because PD-1 is induced on the surface of activated lymphocytes, an antibody against PD-1 can be used to target the depletion of these specific cells by Fc-R dependent mechanisms or by ablation by conjugating a cytotoxic drug (e.g., ricin, saporin, or calicheamicin) to the antibody. In one embodiment, the antibody toxin can be a bispecific antibody. Such bispecific antibodies are useful for targeting a specific cell population, e.g., using a marker found only on a certain type of cell, e.g., a TCR, BCR, or FcR molecule.

Downregulating or preventing B7-4 polypeptide costimulatory functions or activating a B7-4 or a PD-1 inhibitory function (e.g., by stimulation of the negative signaling function of PD-1) is useful to downmodulate the immune response, e.g., in situations of tissue, skin and organ transplantation, in graft-versus-host disease (GVHD), or in autoimmune diseases such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which inhibits or blocks interaction of a B7 molecule with a costimulatory receptor(s) on immune cells (such as a soluble, monomeric form of a B7-4 or PD-1 polypeptide) alone or in conjunction with another downmodulatory agent prior to or at the time of transplantation can inhibit the generation of a costimulatory signal. Moreover, inhibition of B7-4 costimulatory signals, or promotion of a B7-4 or PD-1 inhibitory signal may also be sufficient to anergize the immune cells, thereby inducing tolerance in a subject. Induction of long-term tolerance by blocking a B7-4 mediated costimulatory signal may avoid the necessity of repeated administration of these blocking reagents.

To achieve sufficient immunosuppression or tolerance in a subject, it may also be desirable to block the costimulatory function of other molecules. For example, it may be desirable to block the function of B7-1 and B7-4, B7-2 and B7-4, or B7-1 and B7-4 by administering a soluble form of a combination of peptides having an activity of each of these antigens or blocking antibodies against these antigens (separately or together in a single composition) prior to or at the time of transplantation. Alternatively, it may be desirable to promote inhibitory activity of B7-4 or PD-1 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune,cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs. In another embodiment, a combination of at least two different B7-4 antibodies can be administered to achieve optimal blocking activity.

Blocking B7-4 polypeptide costimulation or activating a B7-4 or PD-1 inhibitory function is also useful in treating autoimmune disease. Many autoimmune disorders are the result of inappropriate activation of immune cells that are reactive against self tissue and which promote the production of cytokines and autoantibodies involved in the pathology of the diseases. Preventing or downmodulating the activation of autoreactive immune cells may reduce or eliminate disease symptoms. Administration of reagents which block costimulation of immune cells by disrupting receptor: ligand interactions of B7 molecules with costimulatory receptors is useful to inhibit immune cell activation and prevent production of autoantibodies or cytokines which are involved in the disease process. Additionally, agents that promote an inhibitory function of B7-4 or PD-1 may induce antigen-specific tolerance of autoreactive immune cells which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

Inhibition of immune cell activation is useful therapeutically in the treatment of allergy and allergic reactions, e.g., by inhibiting IgE production. An agent that promotes a B7-4 or PD-1 inhibitory function can be administered to an allergic subject to inhibit immune cell mediated allergic responses in the subject. Activating a PD-1 molecule is also useful in treating allergies. Inhibition of B7-4 costimulation of immune cells or stimulation of a B7-4 or PD-1 inhibitory pathway can be accompanied by exposure to allergen in conjunction with appropriate MHC molecules. Allergic reactions can be systemic or local in nature, depending on the route of entry of the allergen and the pattern of deposition of IgE on mast cells or basophils. Thus, inhibition of immune cell mediated allergic responses can be local or systemic by administration (e.g., either local or systemic, respectively) of an inhibitory form of an agent that inhibits the interaction of B7-4 with a costimulatory receptor or an agent that promotes an inhibitory function of B7-4 or PD-1.

Inhibition of immune cell activation through blockage of a B7-4 costimulatory activity or stimulation of PD-1 inhibitory activity is also important therapeutically in viral infections of immune cells. For example, in the acquired immune deficiency syndrome (AIDS), viral replication is stimulated by immune cell activation. Blocking a B7-4/costimulatory receptor interaction or stimulation of B7-4 or PD-1 inhibitory function may result in inhibition of viral replication to thereby ameliorate the course of AIDS.

Downregulation of an immune response via stimulation of B7-4 activity or B7-4 interaction with its natural binding partner(s), e.g., PD-1, is also be useful in promoting the maintenance of pregnancy. B7-4 is normally highly expressed in placental trophoblasts, the layer of cells that forms the interface between mother and fetus and is thought to play a role in preventing maternal rejection of the fetus. Females at risk for spontaneous abortion (e.g., those identified by screening for B7-4 activity, as described in the "Prognostic Assays" section, those who have previously had a spontaneous abortion or those who have had difficulty conceiving) because of immunologic rejection of the embryo or fetus can be treated with agents that stimulate the activity of B7-4 or its interaction with its natural binding partner(s), e.g., PD-1.

Downregulation of an immune response via stimulation of B7-4 activity or B7-4 interaction with its natural binding partner(s), e.g., PD-1, is also useful in treating an autoimmune attack of autologous tissues. For example, B7-4 is normally highly expressed in the heart and protects the heart from autoimmune attack. This is evidenced by the fact that the Balb/c PD-1 knockout mouse exhibits massive autoimmune attack on the heart with thrombosis. Thus, conditions that are caused or exacerbated by autoimmune attack (e.g., in this example, heart disease, myocardial infarction or atherosclerosis) may be ameliorated or improved by increasing B7-4 activity or B7-4 biding to its natural binding partner, e.g., PD-1. It is therefore within the scope of the invention to modulate conditions exacerbated by autoimmune attack, such as autoimmune disorders (as well as conditions such as heart disease, myocardial infarction, and atherosclerosis) by stimulating B7-4 activity or B7-4 interaction with PD-1.

4. Upregulation of Immune Responses

Upregulation of B7-4 costimulatory activity or inhibition of the inhibitory activity of PD-1 or B7-4, as a means of upregulating immune responses, is also useful in therapy. Upregulation of immune responses can be in the form of enhancing an existing immune response or eliciting an initial immune response. For example, enhancing an immune response through stimulating B7-4 costimulatory activity or inhibition of B7-4 or PD-1 inhibitory activity is useful in cases of infections with microbes, e.g., bacteria, viruses, or parasites. For example, in one embodiment, a form of B7-4 that promotes a costimulatory signal in an immune cell (e.g., a B7-4 peptide in a multi-valent form (e.g., a soluble multivalent form or a form expressed on a cell surface)) or an agent that inhibits the interaction of B7-4 with an inhibitory receptor or an agent that inhibits transduction of an inhibitory signal via PD-1, e.g., a non-activating antibody against PD-1 or a small molecule (e.g., peptidomimetic) PD-1 antagonist, is therapeutically useful in situations where upregulation of antibody and cell-mediated responses, resulting in more rapid or thorough clearance of microbes is beneficial. These situations include, without limitation, viral skin diseases such as Herpes or shingles, in which case such an agent may optimally be delivered topically to the skin. In addition, systemic viral diseases such as influenza, the common cold, and encephalitis might be alleviated by the administration of such agents systemically.

In certain instances, it may be desirable to further administer other agents that upregulate immune responses, for example, forms other B7 family members that transduce signals via costimulatory receptors, in order further augment the immune response.

Alternatively, immune responses can be enhanced in an infected patient by an ex vivo approach, for instance removing immune cells from the patient, contacting immune cells in vitro with a form of B7-4 that promotes a costimulatory signal in an immune cell or an agent that inhibits the interaction of B7-4 with an inhibitory receptor, or an agent that inhibits transduction of an inhibitory signal via PD-1, and reintroducing the in vitro stimulated immune cells into the patient. In another embodiment, a method of enhancing immune responses involves isolating infected cells from a patient (e.g., virally infected cells) transfecting them with a nucleic acid molecule encoding a form of B7-4 that binds to a costimulatory receptor such that the cells express all or a portion of the B7-4 molecule on their surface, and reintroducing the transfected cells into the patient. The transfected cells are capable of delivering a costimulatory signal to, and thereby activating, immune cells in vivo.

Forms of B7-4 that promote a costimulatory signal in an immune cell, or an agent that inhibits the interaction of B7-4 with an inhibitory receptor, or an agent that inhibits transduction of an inhibitory signal via PD-1 can be used prophylactically in vaccines against various polypeptides, e.g., polypeptides derived from pathogens. Immunity against a pathogen (e.g., a virus or bacteria) can be induced by vaccinating with a pathogen protein along with a form of B7-4 that promotes a costimulatory signal in an immune cell, or an agent that inhibits the interaction of B7-4 with an inhibitory receptor, or an agent that inhibits transduction of an inhibitory signal via PD-1, in an appropriate adjuvant. Alternately, a vector comprising genes which encode for both a pathogenic antigen and a form of B7-4 that binds to costimulatory receptors can be used for vaccination. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) *J. Biotechnol.* 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert (1997) *Proc. Natl. Acad. Sci. USA* 94:961). Attenuated microorganisms can be used for delivery to mucosal surfaces (Sizemore et al. (1995) *Science* 270:29).

In one embodiment, a form of a B7-4 polypeptide which transmits a costimulatory signal can be administered with class I MHC proteins by, for example, a cell transfected to coexpress a B7-4 polypeptide and MHC class I α chain protein and $\beta_2$ microglobulin to result in activation of T cells and provide immunity from infection. Pathogens for which vaccines are useful include, without limitation, hepatitis B, hepatitis C, Epstein-Barr virus, cytomegalovirus, HIV-1, HIV-2, tuberculosis, malaria and schistosomiasis.

In another application, upregulation or enhancement of a B7-4 costimulatory function is useful in the induction of tumor immunity. Endogenous expression of wild-type B7-4 on tumor cells inhibits the immune response against tumor cells. Accordingly, inhibition of the the interaction between B7-4 on tumor cells and PD-1 is useful in inducing tumor immunity. In one embodiment, a PD-1 antagonist (e.g., a non-activating antibody against PD-1 or B7-4 or a small molecule PD-1 or B7-4 antagonist) is administered to a subject having or at risk for a tumor.

In another embodiment, tumor cells (e.g., sarcoma, melanoma, lymphoma, leukemia, neuroblastoma, carcinoma) transfected with a nucleic acid molecule encoding a B7-4 antigen are administered to a subject to overcome tumor-specific tolerance in the subject. If desired, the tumor cell can be transfected to express a combination of B7 polypeptides (e.g., B7-1, B7-2, B7-4 in any combination). For example, tumor cells obtained from a patient can be transfected ex vivo with an expression vector directing the expression of a B7-4 polypeptide alone, or in conjunction with a peptide having B7-1 activity and/or B7-2 activity. The transfected tumor cells are returned to the patient to result in expression of the peptides on the surface of the transfected cell. Alternatively, gene therapy techniques can be used to target a tumor cell for transfection in vivo.

In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain protein and $β_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, and/or B7-2, and/or B7-4) induces a T cell mediated immune response against the transfected tumor cell. Optionally, a gene encoding an antisense construct which blocks expression of an MHC class II associated protein, such as the invariant chain, can also be cotransfected with a DNA encoding a B7-4 polypeptide to promote presentation of tumor associated antigens and induce tumor specific immunity (for instance as taught in U.S. Pat. No. 5,919,639, the contents of which are icorporated herein by reference). Expression of B7-1 by B7 negative murine tumor cells has been shown to induce T cell mediated specific immunity accompanied by tumor rejection and prolonged protection to tumor challenge in mice (Chen, L., et al. (1992) *Cell* 71:1093–1102; Townsend, S. E. and Allison, J. P. (1993) *Science* 259:368–370; Baskar, S. et al. (1993) *Proc. Natl. Acad. Sci.* 90:5687–5690). Thus, the induction of a immune cell mediated immune response in a human subject can be sufficient to overcome tumor-specific tolerance in the subject.

In another embodiment, the immune response can be stimulated by the transmission of a signal via a costimulatory receptor that binds to B7-4 or by inhibiting signaling via an inhibitory receptor that binds to B7-4, e.g., PD-1, such that preexisting tolerance is overcome. For example, immune responses against antigens to which a subject cannot mount a significant immune response, e.g., to an autologous antigen, such as a tumor specific antigen, can be induced by administering an agent that inhibits the inhibitory activity of PD-1 or the ability of B7-4 to bind to an inhibitory ligand. For example, in one embodiment, soluble PD-1 or soluble B7-4 can be used (e.g., PD-1Fc or B7-4 Fc) to enhance an immune response, e.g., to a tumor cell. In one embodiment, an autologous antigen, such as a tumor-specific antigen can be coadministered with an agent that inhibits the inhibitory activity of PD-1 or the ability of B7-4 to bind to an inhibitory ligand. In another embodiment, an immune response can be stimulated against an antigen (e.g., an autologous antigen) to treat a neurological disorder. In another embodiment, PD-1 antagonists can be used as adjuvants to boost responses to foreign antigens in the process of active immunization.

In yet another embodiment, the cellular production of a form of B7-4 that binds to an inhibitory receptor or that competes with the binding of B7-4 to a costimulatory receptor (e.g., a form of B7-4 that binds to PD-1 or a naturally occurring soluble molecule) can be inhibited, e.g., using antisense RNA, in order to upregulate the immune response. For example, in one embodiment, the production of inhibitory B7-4 molecules by a tumor cell can be inhibited in order to increase anti-tumor immunity.

In one embodiment, immune cells are obtained from a subject and cultured ex vivo in the presence of a form of B7-4 that binds a costimulatory molecule or in the presence of an agent that inhibits a B7-4 or PD-1 inhibitory signal, to expand the population of immune cells. In a further embodiment the immune cells are then administered to a subject. Immune cells can be stimulated to proliferate in vitro by, for example, providing to the immune cells a primary activation signal and a costimulatory signal, as is known in the art. Various forms of B7-4 proteins or agents that bind a costimulatory receptor or that inhibit signaling via PD-1 can also be used to costimulate proliferation of immune cells. In one embodiment immune cells are cultured ex vivo according to the method described in PCT Application No. WO 94/29436. The costimulatory molecule can be soluble, attached to a cell membrane, or attached to a solid surface, such as a bead.

B. Identification of Cytokines Modulated by Modulation of B7-4 and/or PD-1

The B7-4 and PD-1 molecules described herein can be used to identify cytokines which are produced by or whose production is enhanced or inhibited in immune cells in response to modulation of B7-4 and/or PD-1 activity. Immune cells expressing PD-1 can be suboptimally stimulated in vitro with a primary activation signal, for example, T cells can be stimulated with phorbol ester, anti-CD3 antibody or preferably antigen in association with an MHC class II molecule, and given a costimulatory signal, e.g., by a stimulatory form of B7 family antigen, for instance by a cell transfected with nucleic acid encoding a B7 polypeptide and expressing the peptide on its surface or by a soluble, stimulatory form of the peptide. Known cytokines released into the media can be identified by ELISA or by the ability of an antibody which blocks the cytokine to inhibit immune cell proliferation or proliferation of other cell types that is induced by the cytokine. For example, an IL-4 ELISA kit is available from Genzyme (Cambridge Mass.), as is an IL-7 blocking antibody. Blocking antibodies against IL-9 and IL-12 are available from Genetics Institute (Cambridge, Mass.). The effect of stimulating or blocking the interaction of B7-4 with PD-1 on the cytokine profile can then be determined.

An in vitro immune cell costimulation assay as described above can also be used in a method for identifying novel cytokines which can be modulated by modulation of B7-4 and or PD-1. For example, where stimulation of the CD28/CTLA4 pathway seems to enhance IL-2 secretion, stimulation of the ICOS pathway seems to enhance IL-10 secretion (Hutloff et al. 199. Nature 397:263). If a particular activity induced upon costimulation, e.g., immune cell proliferation, cannot be inhibited by addition of blocking antibodies to known cytokines, the activity may result from the action of an unknown cytokine. Following costimulation, this cytokine can be purified from the media by conventional methods and its activity measured by its ability to induce immune cell proliferation.

To identify cytokines which may play a role the induction of tolerance, an in vitro T cell costimulation assay as described above can be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a cytokine blocking antibody to a subject along with an agent that promotes a B7-4 or a PD-1 inhibitory activity.

C. Identification of Molecules which Modulate Expression of a B7-4 or PD-1 Polypeptide The antibodies produced using the proteins and peptides of the current invention can be used, e.g., in a screening assay for molecules which modulate the expression of B7-4 or PD-1 polypeptide on cells. For example, molecules which modulate intracellular signaling pathways that culminate in changes in expression of B7-4 or PD-1 polypeptides (e.g., in response to activation signals), can be identified by assaying expression of one or more B7-4 or PD-1 polypeptides on the cell surface. Reduced immunofluorescent staining by an appropriate antibody in the presence of the molecule would indicate that the molecule inhibits intracellular signals. Molecules which upregulate B7-4 or PD-1 polypeptide expression result in an increased immunofluorescent staining. Alternatively, the effect of a molecule on expression of a polypeptide can be determined by detecting cellular mRNA levels using a probe of the invention. For example, a cell which expresses a B7-4 or PD-1 polypeptide can be contacted with a molecule to be tested, and an increase or decrease in mRNA levels in the cell detected by standard techniques, such as Northern hybridization analysis or conventional dot blot of mRNA or total poly($A^+$)RNAs using a cDNA probe labeled with a detectable marker. Molecules which modulate expression of a B7-4 or PD-1 polypeptide are useful therapeutically for either upregulating or downregulating immune responses alone or in conjunction with soluble blocking or stimulating reagents as described above. For instance, a molecule which inhibits expression of B7-4 can be administered together with a second agent (e.g., an immunosuppressant) or a molecule which inhibits expression of PD-1 can be given with an immunostimulant (e.g., an adjuvant). Exemplary molecules which can be tested for their ability to modulate B7-4 or PD-1 include cytokines such as IL-4, γINF, IL-10, IL-12, GM-CSF and prostaglandins.

D. Screening Assays

The invention provides a method (also referred to herein as a "screening assay") for identifying modulators, i.e., candidate or test compounds or agents (e.g., peptides, peptidomimetics, small molecules, or other drugs) which bind to B7-4 or PD-1 proteins, have a stimulatory or inhibitory effect on, for example, B7-4 or PD-1 expression, or B7-4 or PD-1 activity.

One such assay for identifying a compound which modulates the activity of B7-4 or PD-1 is a cell-based assay. In one embodiment of the assay, a cell expressing PD-1 is contacted with a test compound. The cell is also contacted with an activator of PD-1 (e.g., B7-4 in soluble form or expressed on a cell) and then is assayed for PD-1 activity. Increased or decreased activity of the PD-1 of the cell in the presence of the test compound, as compared to the activity of the PD-1 of the cell in the absence of the test compound indicates that the compound modulates the activity of the PD-1, and thus modulates signaling of PD-1. A similar assay can be performed for identifying a modulator of B7-4 activity. For instance, an activating form of B7-4 (in soluble form or expressed on a cell) can be added to a cell expressing a receptor known to be bound and activated by B7-4, in the presence and absence of a test compound, and the B7-4 activity then assayed to determine if the test compound has modulatory activity.

In one embodiment, the invention provides assays for screening candidate or test compounds which bind to, or modulate the activity of, a B7-4 or PD-1 protein or polypeptide or biologically active portion thereof, e.g., which modulate the ability of B7-4 or PD-1 polypeptide to interact with its cognate binding partner or an interactor molecule, such as an intracellular interactor molecule.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci. USA* 87:6378–6382); (Felici (1991) *J. Mol. Biol.* 222:301–310); (Ladner supra.).

In another embodiment, an assay is a cell-based assay comprising contacting a cell expressing a B7-4 target molecule (an intracellular interactor molecule or a PD-1 receptor) or PD-1 target molecule (e.g., a B7-4 ligand or intracellular interactor molecule) with a test compound and determining the ability of the test compound to modulate (e.g., stimulate or inhibit) the activity of the B7-4 or PD-1 target molecule. Determining the ability of the test compound to modulate the activity of a B7-4 or PD-1 target molecule can be accomplished, for example, by determining the ability of the B7-4 or PD-1 protein to bind to or interact with the B7-4 or PD-1 target molecule, as molecules which bind to or interact with the target molecule are more likely to modulate activity. Determining the ability of the B7-4 or PD-1 protein to bind to or interact with its binding partner can be accomplished, e.g., by measuring direct binding.

In a direct binding assay, the B7-4 or PD-1 protein (or their respective target molecules) can be coupled with a radioisotope or enzymatic label such that binding of the B7-4 or PD-1 protein to a B7-4 or PD-1 target molecule can be determined by detecting the labeled protein in a complex. For example, B7-4 or PD-1 molecules, e.g., B7-4 or PD-1 proteins, can be labeled with $^{125}I$, $^{35}S$, $^{14}C$, or $^3H$, either directly or indirectly, and the radioisotope detected by direct counting of radioemission or by scintillation counting. Alternatively, B7-4 or PD-1 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between B7-4 or PD-1 and its target molecule, without the labeling of any of the interactants. For example, a microphysiometer can be used to detect the interaction of B7-4 or PD-1 with its target molecule without the labeling of either B7-4 or PD-1 or the target molecule (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the B7-4 or PD-1 protein to bind to or interact with a B7-4 or PD-1 target molecule can be accomplished by determining the activity of the B7-4, PD-1 or the appropriate target molecule. For example, the activity of B7-4, PD-1 or the appropriate target molecule can be determined by detecting induction or inhibition of induction of a cellular second messenger (e.g., serine/threonine or tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by B7-4, PD-1 or the appropriate target molecule. For example, determining the ability of the B7-4 or PD-1 protein to bind to or interact with a B7-4 or PD-1 target molecule can be accomplished, for example, by measuring the ability of a compound to modulate immune cell costimulation or inhibition in a proliferation assay, or by interfering with the ability of a B7-4 or PD-1 polypeptide to bind to antibodies that recognize a portion of the B7-4 or PD-1 polypeptide.

In another example, the activation of PD-1 (via ligation of the receptor) results in the phosphorylation of the SHP-2 molecule. SHP-2 (also known as Syp, SHPTP2, PTP2C, PTPN11, PTP1D and BPTP3) is a member of the family of non-membrane tyrosine phosphatases (U.S. Pat. No. 5,589,375, and U.S. Pat. No. 5,831,009, the contents of which are incorporated herein by reference). It is ubiquitously expressed in all tissues examined with the highest levels in the heart and brain (Ahmad et al., *Proc. Natl. Acad. Sci. U.S.A.*, 90: 2197–2201(1993); Bastien et al., *Biochem. Biophys. Res. Commun.* 196: 124–133 (1993); Freeman et al., *Proc. Natl. Acad. Sci. U.S.A.*, 89: 11239–11243 (1992)).

The SHP-2 protein contains two src homology 2 (SH2) domains, conserved regions of approximately 100 amino acids originally identified in Src protein tyrosine kinases, that promote protein-protein interactions through phosphotyrosyl residue binding (Neel, Semin. *Cell. Biol* 4: 419–432 (1993)). These two domains have been shown to display differential functions in the regulation of the SHP-2 phosphatase and consequently affect different signaling pathways. The N-terminal SH2 domain serves as a regulatory and recruiting domain, producing an autoinhibitory effect through intramolecular interactions with the internal catalytic phosphatase domain. While the C-terminal SH2 domain acts merely to recruit other proteins for intermolecular interactions necessary for signal transduction (Pei et al., *Proc. Natl. Acad. Sci. U.S.A.* 93: 1141–1145 (1996)). The phosphorylation state of the SHP-2 molecule regulates its phosphatase activity.

Protein-tyrosine phosphatases, including SH2-containing phosphatases, are highly conserved among eukaryotes from such diverse species as mammals, including humans, to yeast and Xenopus. Mutations and altered expression of protein-tyrosine phosphatases have been implicated in a number of pathologic conditions, such as neoplastic diseases and developmental abnormalities (Tonks, N. K., et al., *Cell* 87:365–368 (1996); Neel, B. G., et al., *Curr. Op. Cell Biol.* 9:193–204 (1997); Li, J. et al., *Science*275: 1943–1947 (1997)). SHP-2 has been shown to play a critical role in aberrant immunological responses (e.g., in the allergic response. (Pazdrak et al., *J. Exp. Med.* 186: 561–568 (1997)).

Phosphorylation of the SHP-2 molecule is an indication of signaling via PD-1. SHP-2 phosphorylation is easily detectable by methods known in the art, including, without limitation, the detection of altered mobility of the SHP-2 molecule on a PAGE gel, phosphorylation assays, and assays which measure the activity of the SHP-2 molecule. Detection of SHP-2 phosphorylation may be direct, or alternatively may be indirect, e.g., detection of a downstream activity or event.

In another example, the activation of PD-1 (via ligation of the receptor) results in the inhibition of phosphorylation of the extracellular signal-regulated kinase 1 and 2 (ERK 1 and 2), induced by T cell receptor activation. ERK1 and ERK2 (also known as MAPK1 and MAPK2) are themselves kinases (Boulton, et al., *Cell* 65: 663–675, (1991)). Activation of the ERK molecule is via serine/threonine phosphorylation or tyrosine phosphorylation. Thus, the inhibition of phosphorylation of ERK1 and 2 by PD-1 signaling in an otherwise activated T cell, indicates inhibition of ERK 1 and 2 activation by PD-1. Inhibition of ERK 1 and 2 activation may result from inhibition of upstream phosphorylation of the ERK 1 and 2 molecules, or may result from the activation of a phosphatase which dephosphorylates ERK1 and 2, to reduce activity.

The ERK proteins are known to be activated by phosphorylation by the MEK molecule, a dual-specificity kinase. Upon activation, ERK1 and ERK2 translocate to the nucleus where they can directly phosphorylate and activate a variety of transcription factors including c-Myc, C/EBPβ, p62,TCF /Elk-1, ATF-2 and c-Jun.

The phosphorylation state/activation state of the ERK1 and 2 molecules upon T cell activation is an indication of signaling via PD-1. The phosphorylation state/state of activation of ERK 1 and 2 can readily be determined by the skilled practitioner using assays readily available in the art. For instance, the phosphorylation state of the ERK1 and 2 molecules can be determined using an antibody specific for the phosphorylated form of the p42/44 ERK1/2 proteins (phospho-Thr202/Tyr204 specific), several of which are commercially available. Alternatively, the phosphorylation state of the ERK1 and 2 molecules can be determined by their mobility on a gel, using an antibody which recognizes ERK1 and 2, regardless of the phosphorylation state) for identification. Alternatively, the activation state of ERK1 and 2 can be determined by assaying kinase activity of the ERK1 and 2 molecules. Determination of the ERK1 and 2 phosphorylation/activation state may also be by indirect methods, e.g.,. detection of a downstream activity or event.

In another example, the activation of PD-1 (via ligation of the receptor) results in the inhibition of phosphorylation of the protein kinase C-θ (PKC-θ) molecule induced by T cell receptor activation. The PKC isoenzymes play an important role in many cell signaling events. PKC-θ (also known as PKC-θ, PKCT, PRKCT, nPKC-θ and PRKCQ) is a calcium-independent isoform of the PKC family of serine-threonine kinases. PKC-θ, one of the novel serine/threonine protein kinase C isoforms (nPKC), is expressed ubiquitously in tissues with the highest levels found in hematopoietic cell lines, including T-cells and thymocytes. (Baier et al., *J. Biol. Chem.* 268: 4997–5004 (1993); Keenan et al., *Immunology*

90: 557–563 (1997); Meller et al., *Cell. Immunol.* 193: 185–193 (1999); Wang et al., *Biochem.Biophys. Res. Commun.* 91: 240–246 (1993)). Transient overexpression of the PKC-θ protein in murine thymoma cells resulted in transcriptional activation of an interleukin-2 promoter-driven construct (Baier et al., *Eur. J. Biochem.* 225: 195–203 (1994)), indicating a role for PKC-θ in T-cell signaling pathways. More recently, PKC-θ has been shown to be activated in the course of T cell receptor mediated T cell activation, and this activation correlates with translocation of the PKC-θ molecule to the plasma membrane at the site of APC contact (U.S. Pat. No. 6,040,152, the contents of which are incorporated herein by reference). PKC-θ has also been implicated in other cellular processes including apoptosis (Datta et al., *J. Biol. Chem.* 272: 20317–20320 (1997)), cytoskeletal arrangement (Pietromonaco et al., *J. Biol. Chem.* 273: 7594–7603 (1998); Simons et al., *Biochem. Biophys. Res. Commun.* 253: 561–565 (1998)), proliferation (Passalacqua et al., *Biochem. J.* 337: 113–118 (1999)), and angiogenesis and wound repair (Tang et al., *J. Biol. Chem.* 272: 28704–28711 (1997)).

The phosphorylation/activation state of the PKC-θ molecule upon T cell activation is an indication of signaling via PD-1. The phosphorylation state reflects the activation state of the PKC-θ molecule, with phosphorylation indicating activation. The phosphorylation state/state of activation or PKC-θ can readily be determined by the skilled practitioner using assays readily available in the art. For instance, the phosphorylation state of the PKC-θ molecule can be determined using an antibody specific for the phosphorylated form of the PKC-θ protein (e.g., anti-phospho $T_{138}$), which is commercially available. Alternatively, the phosphorylation state of the PKC-θ molecule can be determined by its mobility on a gel, using an antibody which recognizes PKC-θ (regardless of the phosphorylation state) for detection. Alternatively, the activation state of PKC-θ can be determined by assaying kinase activity of the PKC-θ molecule (Kupfer et al., U.S. Pat. No. 6,040,152), or by assaying for translocation to the membrane at the point of APC contact (Kupfer et al., U.S. Pat. No. 6,040,152). Determination of the PKC-θ phosphorylation/activation state may also be by indirect methods, e.g., detection of a downstream activity or event.

In yet another embodiment, an assay of the present invention is a cell-free assay in which a B7-4 or PD-1 protein or biologically active portion thereof is contacted with a test compound and the ability of the test compound to bind to the B7-4 or PD-1 protein or biologically active portion thereof is determined. Binding of the test compound to the B7-4 or PD-1 protein can be determined either directly or indirectly as described above. In a preferred embodiment, the assay includes contacting the B7-4 or PD-1 protein or biologically active portion thereof with a known compound which binds B7-4 or PD-1 to form an assay mixture, contacting the assay mixture with a test compound, and determining the ability of the test compound to interact with a B7-4 or PD-1 protein, wherein determining the ability of the test compound to interact with a B7-4 or PD-1 protein comprises determining the ability of the test compound to preferentially bind to B7-4 or PD-1 polypeptide or biologically active portion thereof as compared to the known compound.

In another embodiment, the assay is a cell-free assay in which a B7-4 or PD-1 protein or biologically active portion thereof is contacted with a test compound and the ability of the test compound to modulate (e.g., stimulate or inhibit) the activity of the B7-4 or PD-1 protein or biologically active portion thereof is determined. Determining the ability of the test compound to modulate the activity of a B7-4 or PD-1 protein can be accomplished, for example, by determining the ability of the B7-4 or PD-1 protein to bind to a B7-4 or PD-1 target molecule by one of the methods described above for determining direct binding. Determining the ability of the B7-4 or PD-1 protein to bind to a B7-4 or PD-1 target molecule can also be accomplished using a technology such as real-time Biomolecular Interaction Analysis (BIA) (Sjolander, S. and Urbaniczky, C. (1991) *Anal. Chem.* 63:2338–2345 and Szabo et al. (1995) *Curr. Opin. Struct Biol.* 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting a B7-4 or PD-1 protein or biologically active portion thereof with a known compound which binds the B7-4 or PD-1 protein to form an assay mixture, contacting the assay mixture with a test compound, and determining the ability of the test compound to interact with the B7-4 or PD-1 protein, wherein determining the ability of the test compound to interact with the B7-4 or PD-1 protein comprises determining the ability of the B7-4 or PD-1 protein to preferentially bind to or modulate the activity of a B7-4 or PD-1 target molecule.

The cell-free assays of the present invention are amenable to use of both soluble and/or membrane-bound forms of proteins (e.g., B7-4 or PD-1 proteins or biologically active portions thereof, or binding partners to which B7-4 or PD-1 binds). In the case of cell-free assays in which a membrane-bound form of a protein is used (e.g., a cell surface B7-4 or PD-1 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either B7-4 or PD-1 or an appropriate target molecule to facilitate separation of complexed from uncomplexed forms of one or both of the proteins, as well as to accommodate automation of the assay. Binding of a test compound to a B7-4 or PD-1 protein, or interaction of a B7-4 or PD-1 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/B7-4 or PD-1 fusion proteins, or glutathione-S-transferase/target fusion proteins, can be adsorbed onto glutathione sepharose beads (Sigma Chemical, St. Louis, Mo.) or glutathione derivatized microtiter plates, which are then combined with the test compound or the test compound and either the non-adsorbed target protein or B7-4 or PD-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of B7-4 or PD-1 binding or activity determined using standard techniques.

Other techniques for immobilizing proteins on matrices can also be used in the screening assays of the invention. For example, either a B7-4 or PD-1 protein or a B7-4 or PD-1 target molecule can be immobilized utilizing conjugation of biotin and streptavidin. Biotinylated B7-4 or PD-1 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with B7-4 or PD-1 protein or target molecules but which do not interfere with binding of the B7-4 or PD-1 protein to its target molecule can be derivatized to the wells of the plate, and unbound target or B7-4 or PD-1 protein trapped in the wells by antibody conjugation. Methods for detecting such complexes, in addition to those described above for the GST-immobilized complexes, include immunodetection of complexes using antibodies reactive with the B7-4 or PD-1 protein or target molecule, as well as enzyme-linked assays which rely on detecting an enzymatic activity associated with the B7-4 or PD-1 protein or target molecule.

In an alternative embodiment, determining the ability of the test compound to modulate the activity of a B7-4 or PD-1 protein can be accomplished by determining the ability of the test compound to modulate the activity of a molecule that functions downstream of B7-4, e.g., a molecule that interacts with B7-4, or a molecule that functions downstream of PD-1, e.g., by interacting with the cytoplasmic domain of PD-1. For example, levels of second messengers can be determined, the activity of the interactor molecule on an appropriate target can be determined, or the binding of the interactor to an appropriate target can be determined as previously described.

In another embodiment, modulators of B7-4 or PD-1 expression are identified in a method wherein a cell is contacted with a candidate or test compound and the expression of B7-4 or PD-1 mRNA or protein in the cell is determined. The level of expression of B7-4 or PD-1 mRNA or protein in the presence of the candidate compound is compared to the level of expression of B7-4 or PD-1 mRNA or protein in the absence of the candidate compound. The candidate compound can then be identified as a modulator of B7-4 or PD-1 expression based on this comparison. For example, when expression of B7-4 or PD-1 mRNA or protein is greater (e.g., reproducibly and statistically significantly greater) in the presence of the candidate compound than in its absence, the candidate compound is identified as a stimulator of B7-4 or PD-1 mRNA or protein expression. Alternatively, when expression of B7-4 or PD-1 mRNA or protein is less (e.g., reproducibly and statistically significantly less) in the presence of the candidate compound than in its absence, the candidate compound is identified as an inhibitor of B7-4 or PD-1 mRNA or protein expression. The level of B7-4 or PD-1 mRNA or protein expression in the cells can be determined by methods described herein for detecting B7-4 or PD-1 mRNA or protein.

Figure 31A:
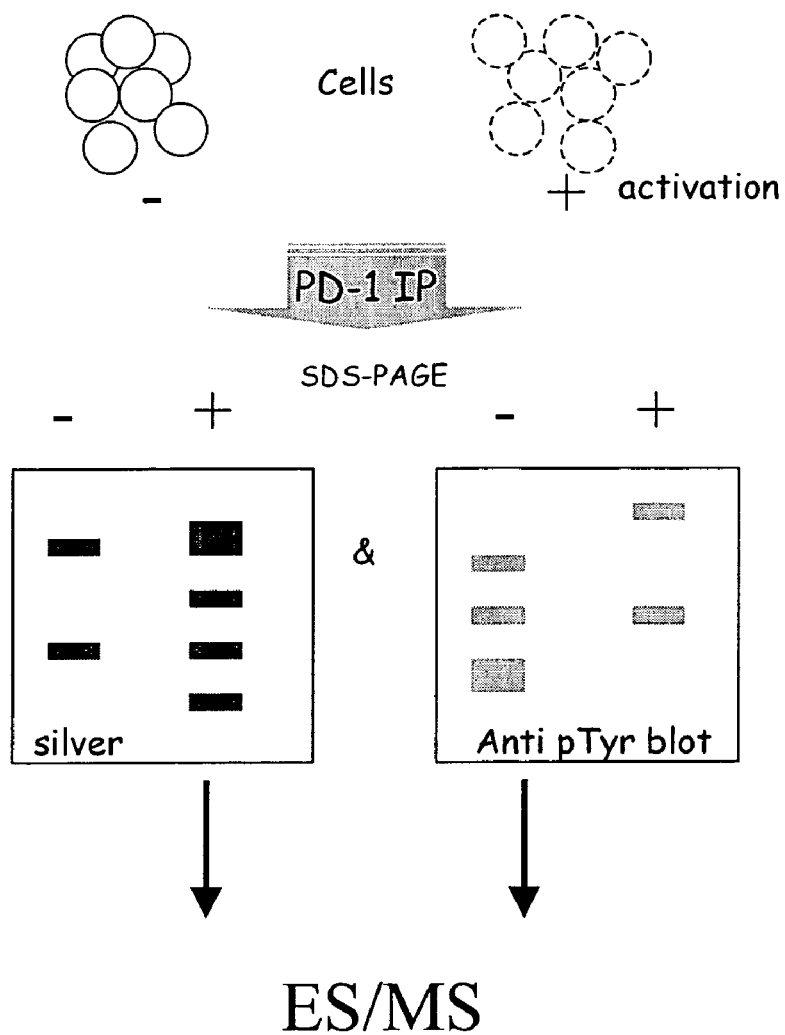

In another embodiment of the invention, peptides and/or proteins which are involved in PD-1 signaling pathways (e.g., proteins which can act as PD-1:B7-4 agonists or antagonists, proteins which are phosphorylated in response to PD-1 signaling, and/or proteins which bind PD-1) can be identified using a peptide binding/immunoprecipitation and mass spectrometry assay. For example, T cells (e.g., Jurkat T cells) can be activated in the presence or absence of B7-4, and in the presence or absence of pervanadate. Proteins can then be immunoprecipitated from lysates of the T cells using, e.g., anti-PD-1 antibodies, anti-phosphotyrosine (Ptyr), or PD-1 peptides. The patterns of immunoprecipitated proteins and the changes in phosphorylation can then be compared using, e.g., SDS-PAGE (sodium dodecyl sulfate polyacrylamide gel electrophoresis). Proteins can then be analyzed and identified using ESI MS/MS (mass spectrometry). A schematic depicting the above described screening assay is shown in FIG. 31A.

Proteins identified using the above-described screening assay (e.g., in an assay using a Jurkat T cell) can then be used in analysis of human T cells. Such proteins can then be used in signaling-based screening assays to identify PD-1 agonists or antagonists, e.g., small molecule agonists or antagonists.

In yet another aspect of the invention, the B7-4 or PD-1 proteins, preferably in membrane bound form, can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins ("B7-4 or PD-1 binding proteins" or "B7-4 or PD-1 bp"), which bind to or interact with B7-4 or PD-1 and are involved in B7-4 or PD-1 activity. Such B7-4 or PD-1 binding proteins are also likely to be involved in the propagation of signals by the B7-4 or PD-1 proteins or B7-4 or PD-1 targets as, for example, upstream or downstream elements of a B7-4 or PD-1 mediated signaling pathway. Alternatively, such B7-4 or PD-1 binding proteins may be B7-4 or PD-1 inhibitors.

The two-hybrid system is based on the modular nature of most transcription factors, which consist of separable DNA-binding and activation domains. Briefly, the assay utilizes two different DNA constructs. In one construct, the gene that codes for a B7-4 or PD-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a B7-4-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the B7-4 or PD-1 protein.

This invention further pertains to novel agents identified by the above-described screening assays. Accordingly, it is within the scope of this invention to further use an agent identified as described herein in an appropriate animal model. For example, an agent identified as described herein (e.g., a B7-4 or PD-1 modulating agent, an antisense B7-4 or PD-1 nucleic acid molecule, a B7-4-or PD-1 specific antibody, or a B7-4 or PD-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

E. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of B7-4 nucleotide sequences, described herein, can be used to map the location of B7-4 genes on a chromosome, The mapping of B7-4 sequences to chromosomes is an important first step in correlating these sequences with genes associated with disease.

Briefly, B7-4 genes can be mapped to chromosomes by preparing PCR primers (preferably 15–25 bp in length) from B7-4 nucleotide sequences. Computer analysis of B7-4 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to B7-4 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using B7-4 nucleotide sequences to design oligonucleotide primers, sublocalization can be achieved with panels of fragments from specific chromosomes. Other mapping strategies which can similarly be used to map a sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (Such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature* 325:783–787.

Moreover, differences in the DNA sequences between individuals affected and unaffected with a disease associated with the B7-4 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The B7-4 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the B7-4 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The B7-4 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 3 can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from B7-4 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial B7-4 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the B7-4 nucleotide sequences or portions thereof having a length of at least 20 bases, preferably at least 30 bases.

The B7-4 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such B7-4 probes can be used to identify tissue by species and/or by organ type.

In a similar fashion, these reagents, e.g., B7-4 primers or probes can be used to screen tissue culture for contamination (i.e., screen for the presence of a mixture of different types of cells in a culture).

F. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining B7-4 or PD-1 protein and/or nucleic acid expression as well as B7-4 or PD-1 activity, in the context of a biological sample (e.g., blood, serum, cells, tissue) to thereby determine whether an individual is afflicted with a disease or disorder, or is at risk of developing a disorder, associated with aberrant B7-4 or PD-1 expression or activity. The invention also provides for prognostic (or predictive) assays for determining whether an individual is at risk of developing a disorder associated with B7-4 or PD-1 protein, nucleic acid expression or activity. For example, mutations in a B7-4 or PD-1 gene can be assayed in a biological sample. Such assays can be used for prognostic or predictive purpose to thereby prophylactically treat an individual prior to the onset of a disorder characterized by or associated with B7-4 or PD-1 protein, nucleic acid expression or activity. The assays described herein, such as the preceding diagnostic assays or the following assays, can also be used to detect a tendency to have spontaneous abortions.

Another aspect of the invention pertains to monitoring the influence of agents (e.g., drugs, compounds) on the expression or activity of B7-4 or PD-1 in clinical trials.

These and other agents are described in further detail in the following sections.

1. Diagnostic Assays

An exemplary method for detecting the presence or absence of B7-4 or PD-1 protein or nucleic acid in a biological sample involves obtaining a biological sample from a test subject and contacting the biological sample with a compound or an agent capable of detecting B7-4 or PD-1 protein or nucleic acid (e.g., mRNA, genomic DNA) that encodes B7-4 or PD-1 protein such that the presence of B7-4 or PD-1 protein or nucleic acid is detected in the biological sample. A preferred agent for detecting B7-4 or PD-1 mRNA or genomic DNA is a labeled nucleic acid probe capable of hybridizing to B7-4 or PD-1 mRNA or genomic DNA. The nucleic acid probe can be, for example, a human B7-4 or PD-1 nucleic acid, such as the nucleic acid of SEQ ID NO:1, 3, 10, or 11 or a portion thereof, such as an oligonucleotide of at least 15, 30, 50, 100, 250 or 500 nucleotides in length and sufficient to specifically hybridize under stringent conditions to B7-4 or PD-1 mRNA or genomic DNA. Other suitable probes for use in the diagnostic assays of the invention are described herein.

A preferred agent for detecting B7-4 or PD-1 protein is an antibody capable of binding to B7-4 or PD-1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect B7-4 or PD-1 mRNA, protein, or genomic DNA in a biological sample in vitro as well as in vivo. For example, in vitro techniques for detection of B7-4 or PD-1 mRNA include Northern hybridizations and in situ hybridizations. In vitro techniques for detection of B7-4 or PD-1 protein include enzyme linked immunosorbent assays (ELISAs), Western blots, immunoprecipitations and immunofluorescence. In vitro techniques for detection of B7-4 or PD-1 genomic DNA include Southern hybridizations. Furthermore, in vivo techniques for detection of B7-4 or PD-1 protein include introducing into a subject a labeled anti-B7-4 or PD-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting B7-4 or PD-1 protein, mRNA, or genomic DNA, such that the presence of B7-4 or PD-1 protein, mRNA or genomic DNA is detected in the biological sample, and comparing the presence of B7-4 or PD-1 protein, mRNA or genomic DNA in the control sample with the presence of B7-4 or PD-1 protein, mRNA or genomic DNA in the test sample.

The invention also encompasses kits for detecting the presence of B7-4 or PD-1 in a biological sample. For example, the kit can comprise a labeled compound or agent capable of detecting B7-4 or PD-1 protein or mRNA in a biological sample; means for determining the amount of B7-4 or PD-1 in the sample; and means for comparing the amount of B7-4 or PD-1 in the sample with a standard. The compound or agent can be packaged in a suitable container. The kit can further comprise instructions for using the kit to detect B7-4 or PD-1 protein or nucleic acid.

2. Prognostic Assays

The diagnostic methods described herein can furthermore be utilized to identify subjects having or at risk of developing a disease or disorder associated with aberrant B7-4 or PD-1 expression or activity. For example, the assays described herein, such as the preceding diagnostic assays or the following assays, can be utilized to identify a subject having or at risk of developing a disorder associated with B7-4 or PD-1 protein, expression or activity. Thus, the present invention provides a method for identifying a disease or disorder associated with aberrant B7-4 or PD-1 expression or activity in which a test sample is obtained from a subject and B7-4 or PD-1 protein or nucleic acid (e.g., mRNA, genomic DNA) is detected, wherein the presence of B7-4 or PD-1 protein or nucleic acid is diagnostic for a subject having or at risk of developing a disease or disorder associated with aberrant B7-4 or PD-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant B7-4 or PD-1 expression or activity. Thus, the present invention provides methods for determining whether a subject can be effectively treated with an agent for a disorder associated with aberrant B7-4 or PD-1 expression or activity in which a test sample is obtained and B7-4 or PD-1 protein or nucleic acid expression or activity is detected (e.g., wherein the abundance of B7-4 or PD-1 protein or nucleic acid expression or activity is diagnostic for a subject that can be administered the agent to treat a disorder associated with aberrant B7-4 or PD-1 expression or activity).

The methods of the invention can also be used to detect genetic alterations in a B7-4 or PD-1 gene thereby determining if a subject with the altered gene is at risk for a disorder associated with the B7-4 or PD-1 gene. In preferred embodiments, the methods include detecting, in a sample of cells from the subject, the presence or absence of a genetic alteration characterized by at least one of an alteration affecting the integrity of a gene encoding a B7-4 or PD-1 protein, or the mis-expression of the B7-4 or PD-1 gene. For example, such genetic alterations can be detected by ascertaining the existence of at least one of 1) a deletion of one or more nucleotides from a B7-4 or PD-1 gene; 2) an addition of one or more nucleotides to a B7-4 or PD-1 gene; 3) a substitution of one or more nucleotides of a B7-4 or PD-1 gene, 4) a chromosomal rearrangement of a B7-4 or PD-1 gene; 5) an alteration in the level of a messenger RNA transcript of a B7-4 or PD-1 gene, 6) aberrant modification of a B7-4 or PD-1 gene, such as of the methylation pattern of the genomic DNA, 7) the presence of a non-wild type splicing pattern of a messenger RNA transcript of a B7-4 or PD-1 gene, 8) a non-wild type level of a B7-4 or PD-1 protein, 9) allelic loss of a B7-4 or PD-1 gene, and 10) inappropriate post-translational modification of a B7-4 or PD-1 protein. As described herein, there are a large number of assay techniques known in the art which can be used for detecting alterations in a B7-4 or PD-1 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the B7-4 or PD-1 gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a B7-4 or PD-1 gene under conditions such that hybridization and amplification of the B7-4 or PD-1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Biotechnology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a B7-4 or PD-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in B7-4 or PD-1 can be identified by hybridizing a sample and control nucleic acids, e.g., DNA or RNA, to high density arrays containing hundreds or thousands of oligonucleotides probes (Cronin, M. T. et al. (1996) *Hum. Mutat.* 7:244–255; Kozal, M. J. et al. (1996) *Nat. Med.* 2:753–759). For example, genetic mutations in B7-4 or PD-1 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the B7-4 or PD-1 gene and detect mutations by comparing the sequence of the sample B7-4 or PD-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the B7-4 or PD-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type B7-4 or PD-1 sequence with potentially mutant RNA or DNA obtained from a-tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in B7-4 or PD-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a B7-4 sequence, e.g., a wild-type B7-4 or PD-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify mutations in B7-4 or PD-1 genes. For example, single strand conformation polymorphism (SSCP) can be used to detect differences in electrophoretic mobility between mutant and wild type nucleic acids (Orita et al. (1989) *Proc Natl. Acad. Sci. USA:* 86:2766, see also Cotton (1993) *Mutat. Res.* 285:125–144; and Hayashi (1992) *Genet. Anal. Tech. Appl.* 9:73–79). Single-stranded DNA fragments of sample and control B7-4 or PD-1 nucleic acids can be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA can be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification can be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a B7-4 or PD-1 gene.

Furthermore, any cell type or tissue in which B7-4 or PD-1 is expressed can be utilized in the prognostic assays described herein.

VII. Administration of B7-4 or PD-1 Modulating Agents

B7-4 or PD-1 modulating agents of the invention are administered to subjects in a biologically compatible form suitable for pharmaceutical administration in vivo to either enhance or suppress immune cell mediated immune responses. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a B7-4 or PD-1 polypeptide may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The B7-4 or PD-1 modulating agent (e.g., a peptide, a nucleic acid molecule, antibody, peptidomimetic, or small molecule) can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, to administer B7-4 or PD-1 modulating agent by other than parenteral administration, it may be desirable to coat the peptide with, or co-administer the peptide with, a material to prevent its inactivation.

A B7-4 or PD-1 modulating agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a B7-4 or PD-1 polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient (e.g., peptide) plus any additional desired ingredient from a previously sterile-filtered solution thereof.

When the active compound is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one embodiment of the present invention a therapeutically effective amount of an antibody to a B7-4 or PD-1 protein is administered to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to, the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Monitoring the influence of agents (e.g., drugs or compounds) on the expression or activity of a B7-4 or PD-1 protein can be applied not only in basic drug screening, but also in clinical trials. For example, the effectiveness of an agent determined by a screening assay as described herein to increase B7-4 or PD-1 gene expression, protein levels, or upregulate B7-4 or PD-1 activity, can be monitored in clinical trials of subjects exhibiting decreased B7-4 or PD-1 gene expression, protein levels, or downregulated B7-4 or PD-1 activity. Alternatively, the effectiveness of an agent determined by a screening assay to decrease B7-4 or PD-1 gene expression, protein levels, or downregulate B7-4 or PD-1 activity, can be monitored in clinical trials of subjects exhibiting increased B7-4 or PD-1 gene expression, protein levels, or upregulated B7-4 or PD-1 activity. In such clinical trials, the expression or activity of a B7-4 or PD-1 gene, and preferably, other genes that have been implicated in a disorder can be used as a "read out" or markers of the phenotype of a particular cell.

For example, and not by way of limitation, genes, including B7-4 or PD-1, that are modulated in cells by treatment with an agent (e.g., compound, drug or small molecule) which modulates B7-4 or PD-1 activity (e.g., identified in a screening assay as described herein) can be identified. Thus, to study the effect of agents on a B7-4 or PD-1 associated disorder, for example, in a clinical trial, cells can be isolated and RNA prepared and analyzed for the levels of expression of B7-4 or PD-1 and other genes implicated in the B7-4 or PD-1 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of B7-4 or PD-1 or other genes. In this way, the gene expression pattern can serve as a marker, indicative of the physiological response of the cells to the agent. Accordingly, this response state can be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a B7-4 or PD-1 protein, mRNA, or genomic DNA in the pre-administration sample; (iii) obtaining one or more post-administration samples from the subject; (iv) detecting the level of expression or activity of the B7-4 or PD-1 protein, mRNA, or genomic DNA in the post-administration samples; (v) comparing the level of expression or activity of the B7-4 or PD-1 protein, mRNA, or genomic DNA in the pre-administration sample with the B7-4 or PD-1 protein, mRNA, or genomic DNA in the post administration sample or samples; and (vi) altering the administration of the agent to the subject accordingly. For example, increased administration of the agent may be desirable to increase the expression or activity of B7-4 or PD-1 to higher levels than detected, i.e., to increase the effectiveness of the agent.

Alternatively, decreased administration of the agent may be desirable to decrease expression or activity of B7-4 or PD-1 to lower levels than detected, i.e., to decrease the effectiveness of the agent. According to such an embodiment, B7-4 or PD-1 expression or activity can be used as an indicator of the effectiveness of an agent, even in the absence of an observable phenotypic response.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Isolation of B7-4 cDNA Molecules

The protein sequence of the extracellular domain of human B7-1 was used to search the public databases for nucleic acid molecules encoding homologous polypeptides. Two overlapping sequences in the EST database, AA292201 and AA399416, were identified. These sequences were used to isolate full-length B7-4 cDNAs from human activated keratinocyte and placental cDNA libraries as follows.

Oligonucleotides with the sequence 5'-CAGCTATGGTG-GTGCCGACTACAA-3' (SEQ ID NO:5) and 5'-AGGT-GCTAGGGGACAGTGTTAGACA-3' (SEQ ID NO:6) from these ESTs were synthesized. These oligonucleotides were used to prime a PCR reaction using as template cDNA prepared by reverse transcription of mRNAs from the spleen of a case of follicular lymphoma, activated B cells, INF-γ activated keratinocytes, normal spleen, and placenta. Conditions were 94° C., 1 min; 94° C., 30 sec, 56° C., 30 sec, 68° C,. 1 min for 35 cycles; 68° C., 3 min, hold 4° C. All templates gave a band of the expected size of 389 bp. The 389 bp product from the PCR of INF-γ activated keratinocytes was purified by agarose gel electrophoresis and 0.12 ng was used as a template in a PCR reaction containing 0.05 mM biotin-21-dUTP and the above primers. Conditions were 94° C., 1 min; 94° C., 30 sec, 56° C., 30 sec, 68° C., 2 min for 20 cycles; 68° C., 5 min, hold 4° C. The biotinylated PCR product was purified on a Nucleospin column (Clontech) and used as a probe in the ClonCapture cDNA selection procedure (Clontech). 60 ng of denatured, biotinylated PCR product was incubated with 2 mM $CoCl_2$, 1× RecA buffer, 1 μg of RecA protein, 1× ATP in a final volume of 30 μl. The reaction was incubated at 37° C. for 15 min. To that mixture, 0.7 μg of plasmid DNA of an activated keratinocyte cDNA library and 0.4 μg of a human placental cDNA library was added and incubation continued for 20 min. 50 ng of EcoRV digested lambda DNA was added to the reaction and incubated 5 min. 0.6 μl of 10% SDS and 5.6 μg of proteinase K were added and incubated at 37° C. for 10 min. Proteinase K was inactivated by adding 1 μl of 0.1 M PMSF. Streptavidin magnetic beads were preincubated with 5 μg of sheared salmon sperm DNA for 10 min and the beads captured with a magnet, the supernatant removed, and the beads resuspended in 30 μl of binding buffer (1 mM EDTA, 1 M NaCl, 10 mM Tris-HCl, pH 7.5). The beads were added to the reaction and the reaction incubated for 30 min at room temperature with gentle mixing. The beads were captured with a magnet and the supernatant removed. The beads were washed with 1 ml of washing buffer (1 mM EDTA, 2 M NaCl, 10 mM Tris-HCl, pH 7.5), beads were captured with a magnet and the supernatant removed. The wash procedure was repeated 3 times. One ml of sterile $H_2O$ was added to the washed beads, incubated 5 min at 37° C., beads were captured on a magnet and the supernatant removed. Captured DNA was eluted by adding 0.1 ml of elution buffer (1 mM EDTA, 0.1 N NaOH), incubating 5 min at room temperature, beads were captured with a magnet and the supernatant removed and saved in a new tube. 22.5 μl of precipitation mix containing carrier and pH neutralizers was added along with 2.5 volumes of ethanol. The plasmid DNA was concentrated by centrifugation and re-dissolved in $H_2O$. Plasmid DNA was re-introduced into *E. coli* DH10B/P3 by electroporation and selected on LB-agar plates containing 7.5 μg/ml tetracycline and 25 μg/ml ampicillin. Colonies were lifted onto Nytran filters and hybridized with $^{32}$P-labeled oligonucleotides with the sequence

5'-CAGCTATGGTGGTGCCGACTACAA-3' (SEQ ID NO:5),

5'-AGGTGCTAGGGGACAGTGTTAGACA-3' (SEQ ID NO:6), and

5'-TCGCTTGTAGTCGGCACCACCATA-3' (SEQ ID NO:9). All oligos are from AA292201 sequence. Final wash conditions were 2×SSC, 0.1% SDS at 55° for 20 min. The two hybridizing colonies were picked and the sequence of the cDNA inserts was determined.

Sequencing revealed two forms of B7-4 molecules. The first form, B7-4 secreted (B7-4S) encodes a protein having a short hydrophilic domain without a membrane anchor. The nucleotide and amino acid sequences of this form are shown in SEQ ID NO:1 and 2, respectively. The second form, B7-4 membrane (B7-4M) encodes a protein having a transmembrane and short cytoplasmic domain. The nucleotide and amino acid sequences of this form are shown in SEQ ID NO:3 and 4, respectively. Both members of the B7-4 family identified have signal, IgV, and IgC domains, as illustrated in FIGS. 3 and 4. The B7-4M form has approximately 21% amino acid identity to human B7-1 and about 20% amino acid identity to human B7-2 as calculated using the default Blosum62 matrix with gap penalties set at existence 11 and extension 1 (See the NCBI website), under conditions where B7-1 and B7-2 have about 26% identity.

Example 2

Expression of B7-4 mRNA: Northern Blot Analysis

An mRNA of the soluble form of B7-4 is predicted to be about 1.2 kb though other sizes are possible. The mRNA of the second form is about 3.8 kb, with minor mRNAs of 1.6 and 6.5 kb.

Expression of B7-4 polypeptides was analyzed. RNA was prepared by guanidine thiocyanate homogenization and cesium chloride centrifugation. Equal amounts of RNA (approximately 2 μg poly(A)+ RNA) were electrophoresed on an agarose gel, blotted, and hybridized to a portion of $^{32}$P-labeled B7-4 cDNA common to both the B7-4S and B7-4 M forms. These B7-4 mRNAs are highly expressed in placenta, lung, and heart and are moderately expressed in the thymus. In addition, these B7-4 mRNAs are weakly expressed in skeletal muscle, kidney, pancreas, prostate, testis, ovary, small intestine, colon, and peripheral blood leukocytes. They were also found to be very weakly expressed in liver or brain. B7-4 mRNAs were not expressed in unstimulated monocytes, but were strongly induced by IFN-γ. Similarly, the expression of these polypeptides was found to be induced in keratinocytes by TPA/IFN- γ and in dendritic cells by IFN-γ. These B7-4 mRNAs were not expressed in unstimulated B cells, but were induced by Ig crosslinking.

Expression of these B7-4 mRNAs was also examined in a variety of cell lines. They were not found to be expressed in B cell lines such as Raji, Ramos, LBL, Nalm 6, and DHL-4. They were also not expressed in T cell lines, such as Jurkat, Rex, CEM, HPB-ALL, Peer4, and H9 or in HTLV-1 transformed T cell lines such as SPP and MT2 or in the myeloid line U937.

Example 3

Further Characterization of B7-4 mRNA Expression: Northern Blot Analysis

Mouse and human multiple tissue Northern blots (Clontech, Palo Alto, Calif.) were probed with $^{32}$P-dCTP radiolabeled cDNA probes in QuikHyb (Stratagene, La Jolla, Calif.) according to the manufacturer's instructions. The human B7-4 probe consisted of a 1 kb BamHI/NotI fragment of the cDNA spanning the coding region and 3' untranslated region of SEQ ID NO:1. The mouse B7-4 probe consisted of a 300 bp cDNA fragment from the coding region. Control actin probes were supplied by Clontech. Blots were washed twice at room temperature in 2×SSC, 0.1% SDS, followed by 0.2×SSC, 0.1% SDS at 65° C., and examined by autoradiography.

B7-4 mRNA was expressed at high levels in heart, human placenta, and human fetal liver, and at lower levels in spleen, lymph nodes, thymus, and mouse liver.

B7-4 mRNA was expressed in a variety of transformed mouse cell lines, including PU5-1.8, RAW 264.7, K-Balb, M-MSV-Balb/3T3, Hepa 1–6, R1.1, L1210, P38D 1, P815, and NB41A3 cells.

Example 4

Further Characterization of B7-4 mRNA Expression: Quantitative PCR, Genechip Hybridization, and RNA Blot Analysis B7-4 mRNA expression on antigen presenting cells was examined and compared to the expression of B7-1 and B7-2 on those cells. For quantitative PCR analysis, cellular RNA was deoxyribonuclease-treated, re-extracted and converted to first strand cDNA. FAM (6-caroxyfluorescein)-labeled human B7-4, B7-1, B7-2, and GAPDH probes were purchased from PE Biosystems (B7-4: primers 5'-GCCGAAGTCATCTGGACAAG-3' (SEQ ID NO:13) and 5'-TCTCAGTGTGCTGGTCACAT-3' (SEQ ID NO:14), probe 5'-FAM-CACCACCACCAATTCCAAGA-3' (SEQ ID NO:15); B7-1: primers 5'-ACGTGACCAAGGAAGT-GAAAGAA-3' (SEQ ID NO:16) and 5'-TGC-CAGCTCTCTTCAACAGAAACAT-3' (SEQ ID NO:17), probe 5'-FAM-TGGCAACGCTGTCCTGTGGTCAC-3' (SEQ ID NO:18); B7-2: primers 5'-GGGCCGCA-CAAGTTTTGAT-3' (SEQ ID NO:19) and 5'-GCCCT-TGTCCTTGATCTGAAGA-3' (SEQ ID NO:20), probe 5'-FAM-CGGACAGTTGGACCCTGAGACTTCACA-3' (SEQ ID NO:21).

PCR reactions were set up in 96-well plates using reagents from the Perkin Elmer TAQMAN™ EZ kit, according to the manufacturer's instructions. Standard curves were set up for each of the four genes analyzed. Forty cycles of PCR were run in an ABI Prism 7700 Sequence Detector and GAPDH was used to normalize the B7-4, B7-1, and B7-2 results.

The Affymetrix Mul9KsubA chip was used for Genechip hybridization analysis. The sequence of a portion of murine B7-4 is represented by expressed sequence tag TC 17781 of The Institute for Genomic Research on this chip. RNA isolation, chip hybridization and scanning was performed as described in Byrne, M. C. et al. (2000) *Curr. Prot. Mol. Biol. Suppl.* 49:22.2.1–22.2.13.

For RNA blot hybridization, the 1.6 kb human and 3.6 kb murine B7-4 cDNAs were excised by digestion with Xba I and labeled by random priming with γ-$^{32}$P-ATP and the Klenow fragment of DNA polymerase I. RNA blots were hybridized as described in Freeman, G. J. et al. (1992) *J. Immunol.* 149:3795–3801.

Human dendritic cells were derived from peripheral blood. Mononuclear cells were isolated after fractionation on a Ficoll gradient. Non-adherent cells were removed and the remaining cells cultured in 150 ng/ml human GM-CSF (R&D Systems) and 100 ng/ml human IL-4 (R&D Systems) for 2 days. The non-adherent dendritic cells were isolated (CD80$^+$ CD86$^+$ HLA-DR$^+$ CD54$^+$ CD58$^+$ CD1a$^+$) and cultured in GM-CSF alone or activated with GM-CSF, 2.5 µg/ml LPS (Sigma Chemicals), and 10 ng/ml human Interferon-γ. At 4 hours and 20 hours after activation, cells were harvested and RNA isolated using the RNeasy kit (Qiagen).

Murine bone marrow mononuclear cells were immunodepleted of granulocytes, lymphocytes and Ia$^+$ cells by magnetic activated cell sorting and cultured in petri dishes with GM-CSF and IL-4. Dendritic cells were harvested as the non-adherent population after 7 days of culture, and demonstrated to be 75–80% CD11c$^+$, high IA$^+$ cells. Cells were activated with LPS and human interferon-γ.

Analysis of expression in human blood monocytes by RNA blot hybridization demonstrated that B7-2 is not expressed by unstimulated monocytes, but is rapidly upregulated upon interferon-γ treatment. Treatment of monocytes with another pro-inflammatory cytokine, tumor necrosis factor (TNF)-α led to a low level induction similar to that found with medium alone, presumably as a result of activation by adherence to plastic. In addition to the major 4.2 kb B7-4 mRNA, a minor 1.8 kb B7-4 mRNA species was also observed in interferon-γ treated monocytes. Expression of B7-4 by human B-cells activated by cell surface immunoglobulin cross-linking, but not by the Raji cell line, was also observed. Similarly, B7-1 is not expressed by unstimulated monocytes, but is upregulated in response to interferon-γ with kinetics similar to B7-4 expression. In contrast, B7-2 mRNA is constitutively expressed in monocytes and levels are unaffected by interferon-γ or TNF-α treatment.

B7-4, B7-1, and B7-2 mRNA expression by human dendritic cells was also examined by quantitative PCR. Human peripheral blood-derived dendritic cells were treated with granulocyte-macrophage colony stimulated factor (GM-CSF) alone or activated with GM-CSF, lipopolysaccharide (LPS), and interferon-γ. As a result of activation by LPS and interferon-γ, B7-4 mRNA was rapidly induced with a 16-fold increase at 4 hours and a 34-fold increase at 20 hours, relative to non-induced cells. B7-1 and B7-2 mRNAs were also induced upon activation: B7-1 was induced 21-fold at 4 hours and 22-fold at 20 hours. B7-2 showed little induction at 4 hours; however, expression was induced 5-fold at 20 hours. Expression of B7-4 by murine bone marrow-derived dendritic cells treated with LPS and interferon-γ was examined using Genechip™ hybridization. B7-4 expression in these cells follows a pattern similar to that observed on human dendritic cells: a 5-fold induction of the B7-4 mRNA relative to the uninduced cells at 6 and 20 hours after induction. These data demonstrate that B7-4 is expressed by antigen presenting cells and lymphocytes, and it is induced on dendritic cells in a manner similar to B7-1 and B7-2. Treatment of human keratinocytes with phorbol ester and interferon-γ also induced B7-4.

In murine tissues, an approximately 3.7 kb B7-4 mRNA transcript was detected by northern blot hybridization. The distribution of the murine B7-4 mRNA closely resembled that of the human B7-4, with high levels in heart, thymus and lung, and low levels in kidney, spleen and liver.

Example 5

Chromosomal Localization of B7-4

The chromosomal localization of the B7-4 genes was determined using a monochromosomal blot kit commercially available from Quantum (Toronto, Canada). The blots were probed with a sequence that recognizes both B7-4S and B7-4M. Using this method, the B7-4 polypeptides have been localized to human chromosome 9, whereas B7-1 and B7-2 have been localized to human chromosome 3. The butyrophilins, which also share limited amino acid sequence identity with the B7-4 family have been localized to the major histocompatibility complex on chromosome 6. The chromosomal location of B7-4 was confirmed using B7-4 specific primers in PCR amplification of monochromosomal somatic cell hybrid DNA templates available from Quantum Technologies (Canada).

Example 6

Binding of B7-4 Molecules to T Cell Ligands or Antibodies

COS cells were transfected with either vector DNA (pcD-NAI), or an expression plasmid containing the B7-4M cDNA. After 72 hours, the transfected COS cells were detached by incubation in PBS containing 0.5 mM EDTA for 30 min. at 37° C.

Figure 10:
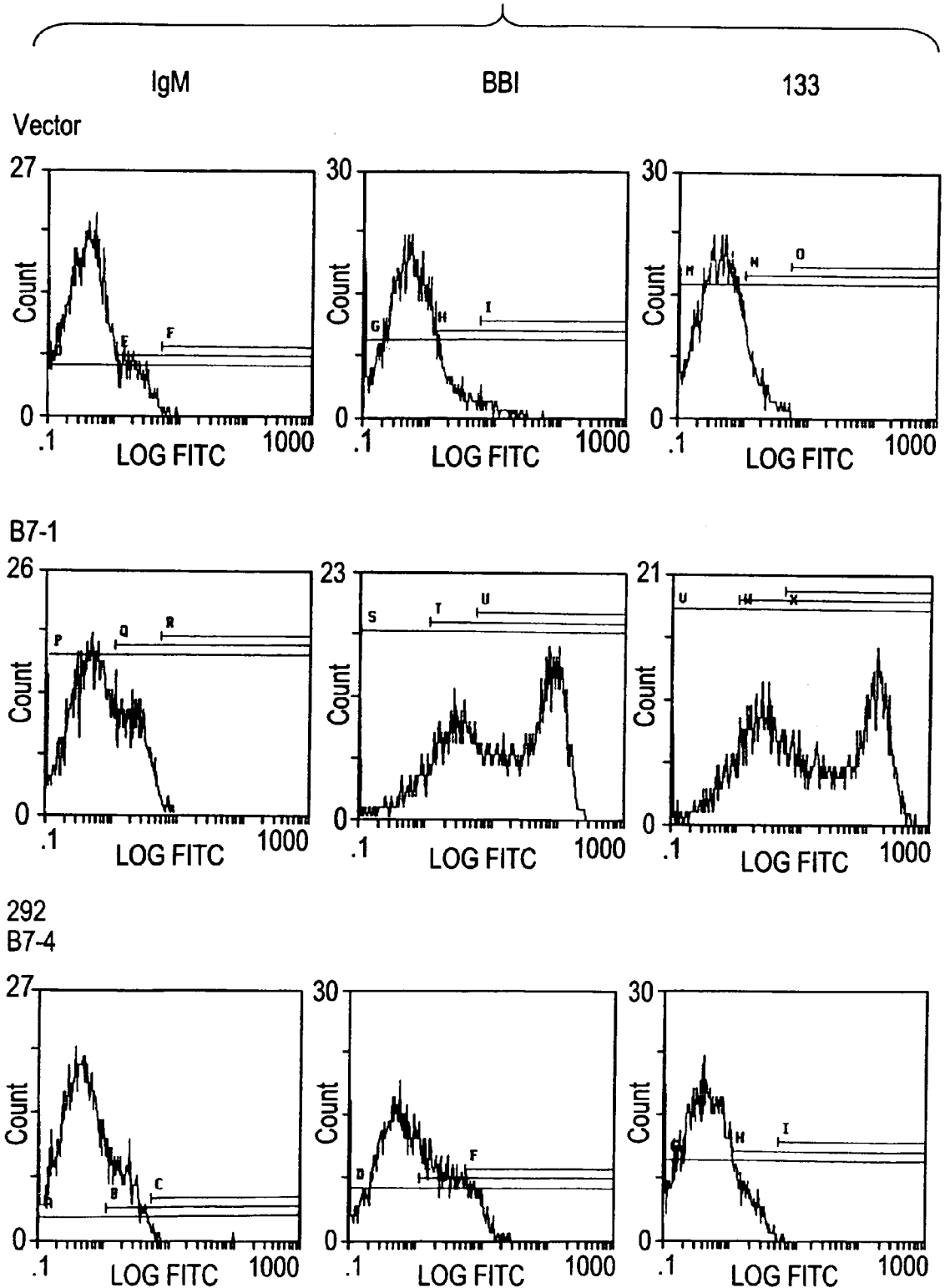
FIG. 10 illustrates the results of FACS analysis of binding of IgM, BB 1 and 133 antibodies to B7-4M- transfected COS cells.

The ability of COS cells expressing B7-4M to bind to various T cell receptors and antibodies was tested. FACS analysis of binding of CD28Ig, CTLA4-Ig, and control Ig by B7-4-transfected COS cells showed that neither CD28Ig nor CTLA4-Ig was bound by B7-4 (FIG. 8). The ability of COS cells expressing B7-4M to bind to IgG and murine ICOS-his fusion protein was also tested. No binding of human B7-4 to murine ICOS was detected (FIG. 9). As shown in FIG. 10, FACS analysis revealed binding of BB1 (anti B7-1 and anti B7–3), but not IgM or 133 (anti-B7) antibodies to B7-4-transfected COS cells.

Example 7

Costimulation of T Cell Proliferation By B7-4 Molecules

The ability of B7-4 polypeptides to costimulate human T cell proliferation was tested.

Human CD28$^+$ T cells were isolated by immunomagnetic bead depletion using monoclonal antibodies directed against B cells, natural killer cells and macrophages as previously described (Gimmi, C. D. et al. (1993) *Proc. Natl. Acad. Sci. USA* 90:6586–6590). B7-4 and vector transfected COS cells were harvested 72 hours after transfection, incubated with 25 µg/ml of mitomycin-C for 1 hour, and then extensively washed. $10^5$ naïve T Cells were stimulated with plate bound anti-CD3 mAb plus 20,000 mitomycin-c treated COS cells transfected with the indicated DNA construct.

Figure 11:
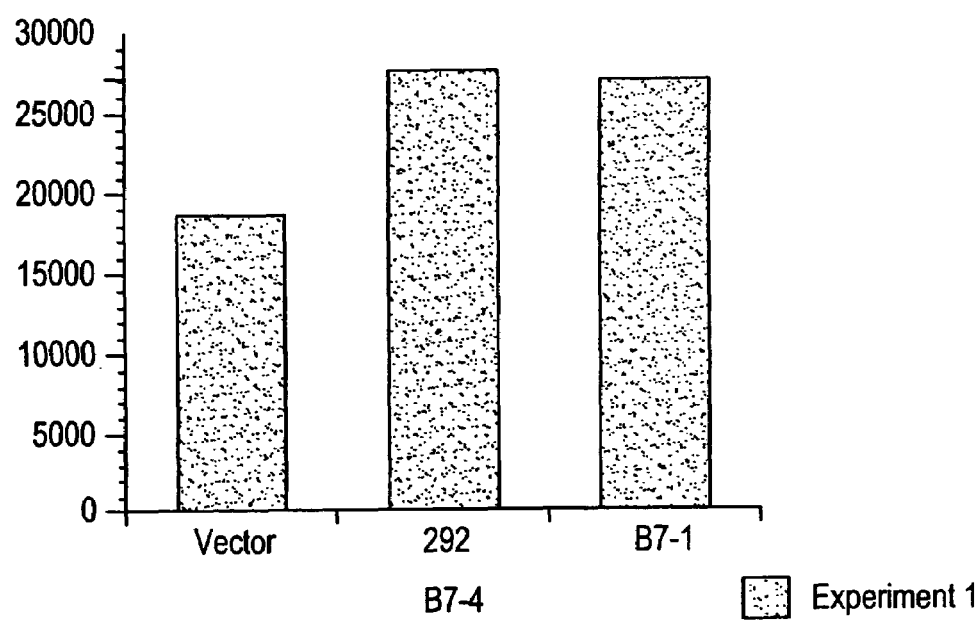
FIG. 11 illustrates that COS cells transfected with B7-4M (292) can costimulate T cell proliferation.
Figure 12:
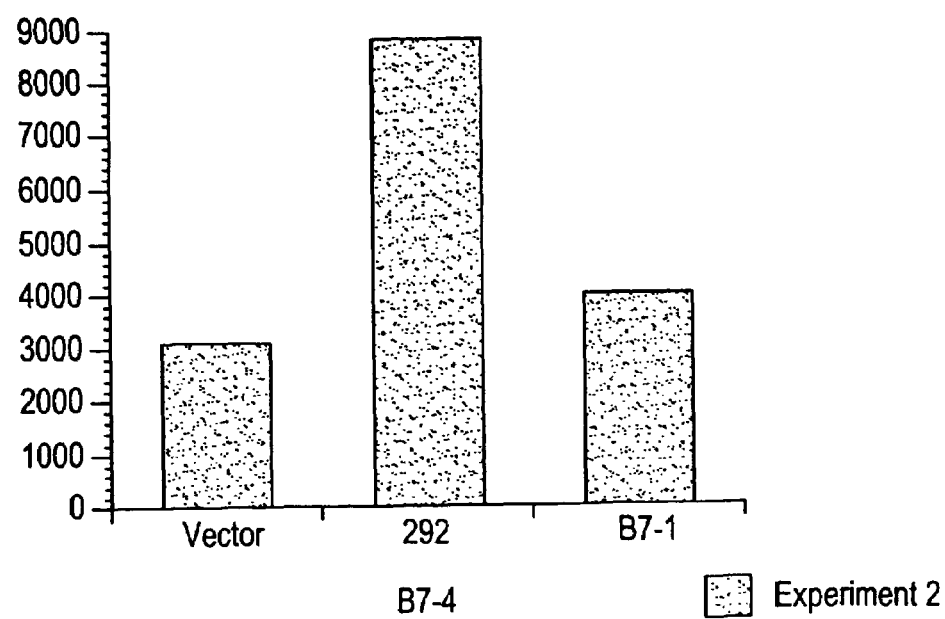
FIG. 12 illustrates that COS cells transfected with a B7-4M (292) can costimulate T cell proliferation.
Figure 13A:
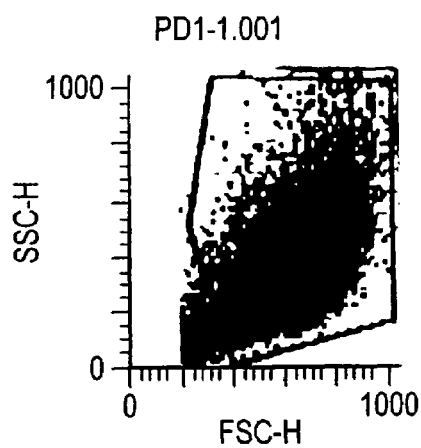
FIGS. 13A–13D illustrate the binding of PD-1 to B7-4M transfected COS cells.
Figure 13B:
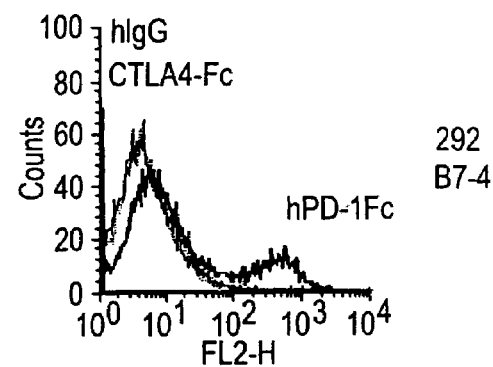
Figure 13C:
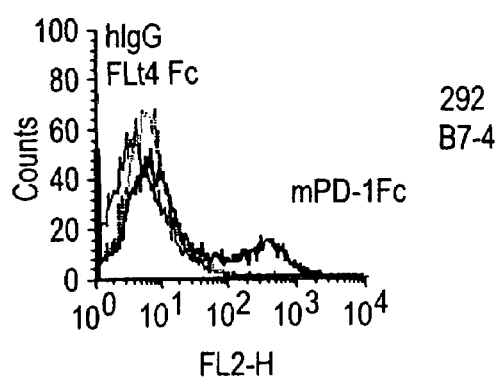
Figure 13D:
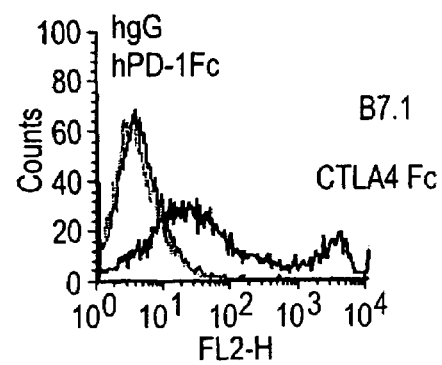
Figures 14A, 14B, 14C:
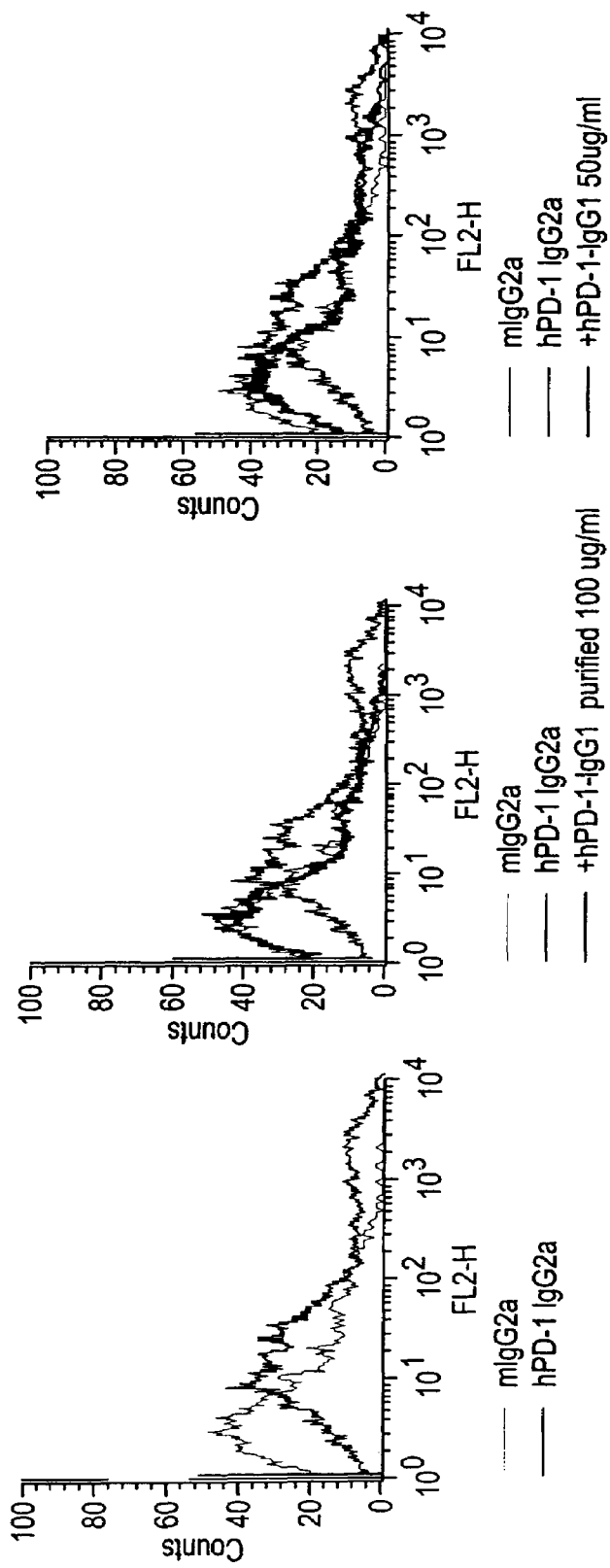
Figure 15G:
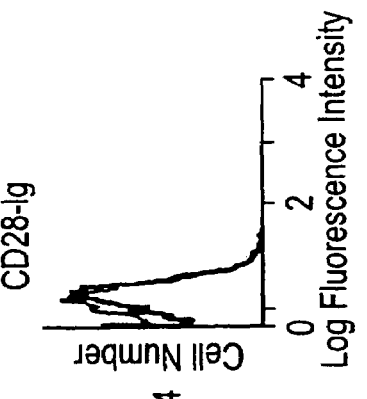
Figure 15J:
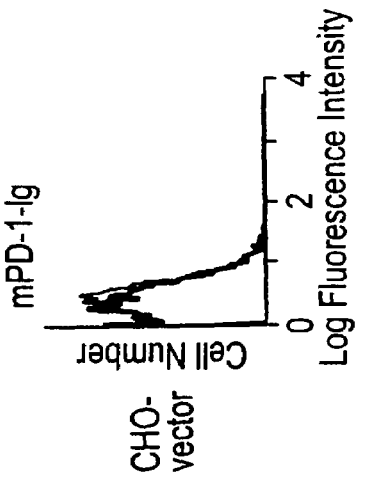
Figure 15H:
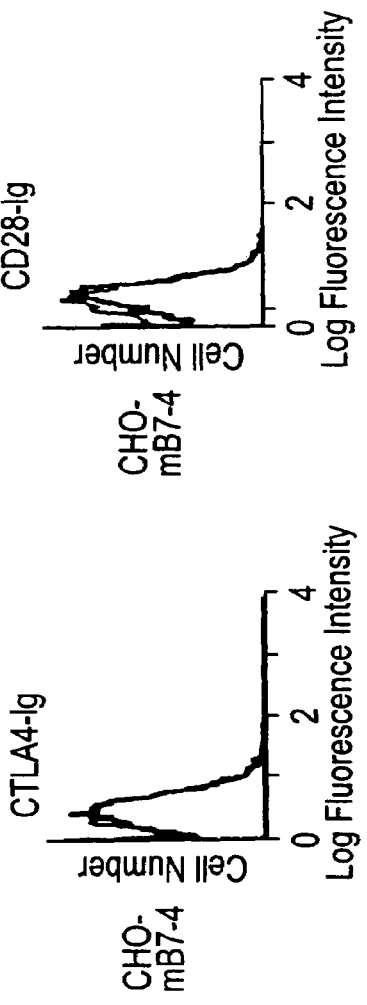
Figure 15K:
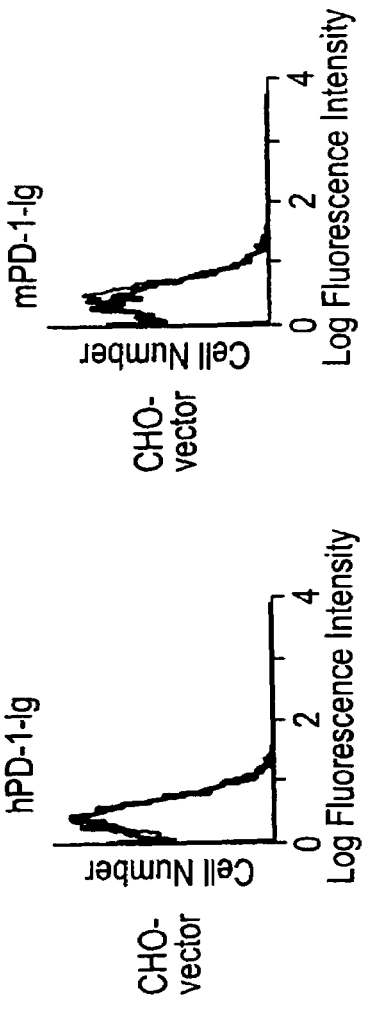
Figure 15I:
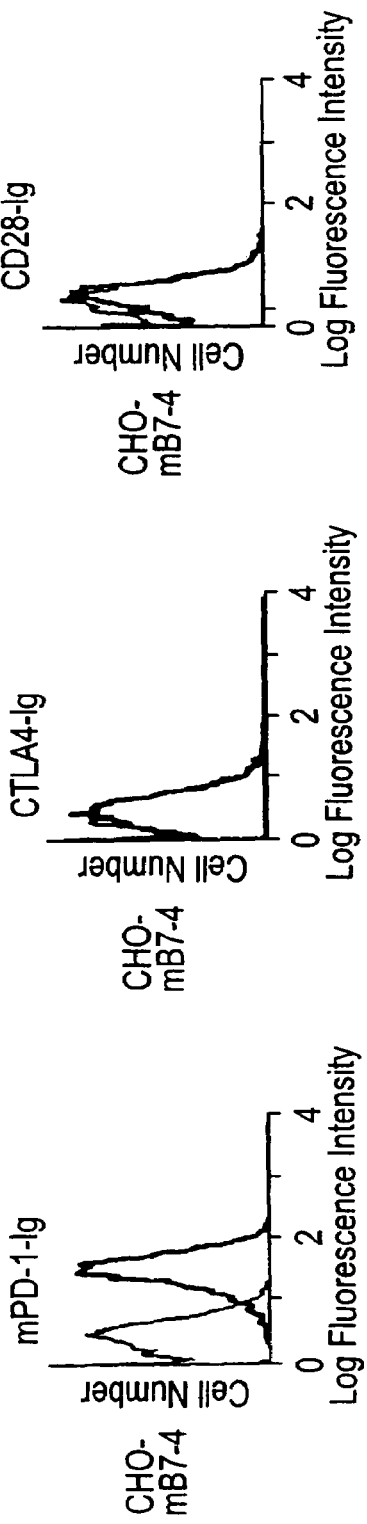
Figure 15L:
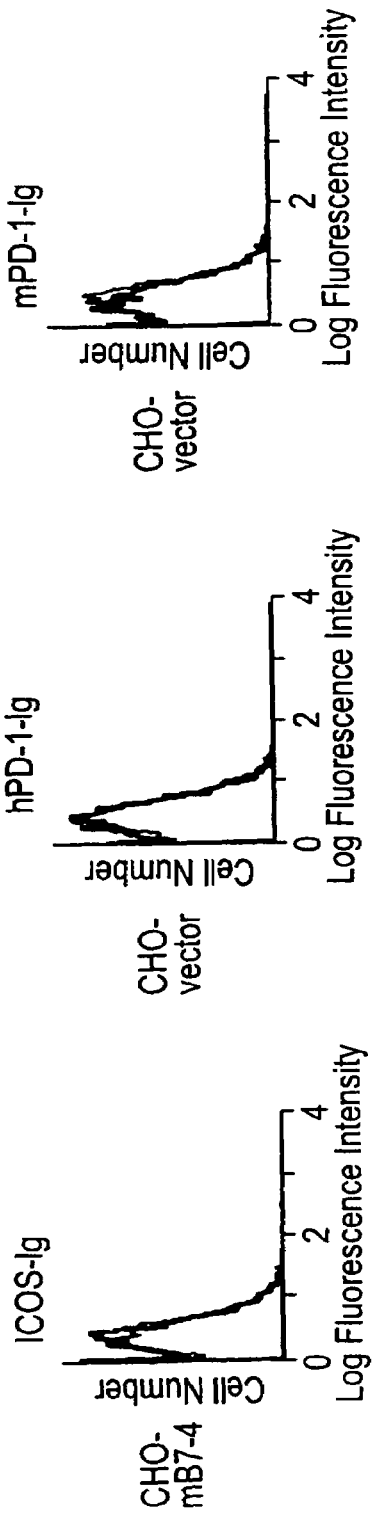

T cell proliferation was measured by 3H-thymidine (1 µCi) incorporated for the last 12 hours of a 72 hour incubation. As shown in FIGS. 11 and 12, COS cells expressing B7-4 can costimulate T cell proliferation.

Example 8

Generation of Murine Antibodies to B7-4 and Use in Detecting Cell-Surface Expression of B7-4

Mammalian expression vectors (pEF6 or pcDNA3.1 (Invitrogen)) were prepared comprising the entire murine or human B7-4 cDNA. The cDNA/vector construct was dissolved in 0.9% saline at 1 mg/ml (not TE or PBS).

Before immunization, 78 µl of 1 mg/ml cardiotoxin (Sigma #C-1777) in 0.9% saline was injected into the tibialis anterior muscle of each hind limb of the mouse being immunized. Each mouse was then left alone for 5 days.

After anesthetizing the mice, 50 µl of 1 mg/ml purified B7-4 cDNA/vector construct (in 0.9% saline) was injected into each regenerating tibialis anterior muscle.

Antibody titers were measured approximately six days after immunization using standard methods, for example, in an ELISA assay. The cDNA immunization was repeated every 2–4 weeks for three cycles (until the antibody titre was >1:10,000). Mice were then boosted with CHO cells transfected with B7-4.

Spleen cells isolated from mice having appropriate antibody titers were harvested. The spleen cells were fused to fusion partners SP2-0) to make hybridomas. Hybridomas and antibodies were manipulated using standard methods (see, e.g., "Antibodies: A Laboratory Manual", Harlow, E. and Lane, D., Cold Spring Harbor Laboratory (1988), which is incorporated herein by reference).

Antibodies 2A3, 10D9, 5A9, and 11D12 were among those selected in screening assays. These antibodies were found to bind to COS or CHO cells transfected with human B7-4 and not to mock transfected cells or to cells transfected with mouse B7-4. The antibodies were used to detect the presence of B7-4 on various cell populations. B7-4 expression was observed, inter alia, on heart tissue, tumor cells (including some lung tumor cells, some ovarian tumor cells, some breast tumor cells, some epithelial tumor cells, and some squamous cell carcinomas), placenta, and thymic epithelium.

Another antibody, clone 29E.2A3.C6 (mouse IgG2bκ) was used to examine cell surface expression of B7-4. B7-4 is expressed on human breast cancer cell lines MDA-231, SKBR-3, and MCF-7.

Example 9

Generation of Fully Human Antibodies to B7-4

In this example, fully human antibodies against B7-4 or PD-1 are made in mice that are transgenic for human immunoglobulin genes. Transgenic mice are made using standard methods, e.g., according to Hogan, et al., "Manipulating the Mouse Embryo: A Laboratory Manual", Cold Spring Harbor Laboratory, which is incorporated herein by reference, or are purchased commercially. Embryonic stem cells are manipulated according to published procedures (Teratocarcinomas and embryonic stem cells: a practical approach, Robertson, E. J. ed., IRL Press, Washington, D.C., 1987; Zijlstra et al. (1989) *Nature* 342:435–438; and Schwartzberg et al. (1989) *Science* 246:799–803, each of which is incorporated herein by reference). DNA cloning procedures are carried out according to Sambrook, J. et al. in Molecular Cloning: A Laboratory Manual, 2d ed., 1989, Cold Spring Harbor Laboratory Press, Cold Spring Harbor, N.Y., which is incorporated herein by reference. Oligonucleotides are synthesized, e.g., on an Applied Bio Systems oligonucleotide synthesizer according to specifications provided by the manufacturer or are purchased commercially.

Transgenic mice are immunized using a purified or recombinant B7-4 or PD-1 or a fusion protein comprising at least an immunogenic portion of the extracellular domain of B7-4 or PD-1. Approximately four hundred μg of B7-4 or PD-1 in 100 μL of phosphate buffered saline (PBS) is injected intraperitoneally into each mouse. Serum samples are collected approximately six days later by retro-orbital sinus bleeding.

Antibody reactivity and specificity for B7-4 or PD-1 are assessed using an indirect enzyme-linked immunosorbent assay (ELISA). Several immunoglobulin superfamily molecules are tested as controls (e.g., CTLA4 and CD28) to analyze the antibody specificity of the antibody for B7-4 or PD-1. Antibodies having human variable regions which bind to B7-4 or PD-1 are detected by enzyme conjugates specific for human IgM and human IgG sub-classes with no cross reactivity to mouse immunoglobulin. Briefly, PVC microtiter plates are coated with B7-4 or PD-1 by coating wells overnight at 37° C. with 5 μg/mL B7-4 in PBS. Serum samples are diluted in PBS, 5% serum, 0.5% Tween-20 and are incubated in the wells for 1 hour at room temperature, followed by anti-human IgG Fc and IgG F(ab')-horseradish peroxidase or anti-human IgM Fc-horseradish peroxidase in the same diluent. After 1 hour at room temperature enzyme activity is assessed by addition of ABTS substrate (Sigma, St. Louis, Mo.) and read after 30 minutes at 415–490 nim. In pre-immunization serum samples from the same mice, titers of human antibodies to the same target antigens are also tested.

Spleen cells isolated from mice having appropriate antibody titers are harvested. The spleen cells are fused to appropriate fusion partners (e.g., myeloma cells) to make hybridomas. Hybridomas and antibodies are manipulated according to "Antibodies: A Laboratory Manual", Ed Harlow and David Lane, Cold Spring Harbor Laboratory (1988), which is incorporated herein by reference.

The complementarity determining sequences of the murine VH and VL domains of a murine antibody could be used to graft into the framework of human immunoglobulins in order to generate a humanized antibody against B7-4 or PD-1 (Riechmann et al. (1988) *Nature* 332:323; Verhoeyen et al. (1988) *Science* 239:1534).

Example 10

Generation of Human Single Chain Fvs Reactive with B7-4 or PD-1

As an alternative to preparing monoclonal antibody-secreting hybridomas, anti B7-4 or anti-PD-1 antibodies (single chain Fv-like portions of antibodies) were identified and isolated by screening a combinatorial library of human immunoglobulin sequences displayed on M13 bacteriophage from Cambridge Antibody Technology Ltd., Melbourn, UK (Winter et al. (1994) *Annu. Rev. Immunol.* 12:433; Hoogenboom et al. (1998) *Immunotechnology* 4:1). PD-1.Fc or B7-4.Fc was used to thereby isolate immunoglobulin library members that bind a B7-4 or PD-1 polypeptide. Kits for generating and screening phage display libraries are commercially available and standard methods were employed to generate the scFv (Helfrich et al. (2000) *J. Immunol. Methods* 237:131–45; Cardoso et al. (2000) *Scand. J. Immunol.* 51:337–44). PD-1.Fc or B7-4.Fc were immobilized on plastic and phage expressing specific scFv were selected by panning and multiple rounds of enrichment (Griffiths et al. (1993) *EMBO J.* 12:725).

Example 11

Identification of a Receptor for B7-4

Fusion proteins consisting of the extracellular region of human PD-1 fused to the hinge-CH2-CH3 domains of either human immunoglobulin gamma 1 or murine Ig gamma2a (with mutations blocking FcR and complement interaction) were used to search for a ligand that binds to PD-1. As part of this search, staining of the cell surface of monocytes stimulated with gamma-interferon was found. B7-4 is induced in monocytes after stimulation with gamma-interferon, as observed by northern blot hybridization.

The binding of PD-1-Fc (human Ig gamma1) to the surface of COS cells transiently transfected with a B7-4-expression vector was tested. COS cells were transfected with either B7-4M or B7-1 using LipofectAMINE transfection reagent. After 48 hours, the cells were stained with human PD-1-Fc, murine PD-1-Fc, CTLA4-Fc, Flt4-Fc, or IgG followed by anti-IgG conjugated to phycoerythrin (PE). The cells were then analyzed by flow cytometry. As shown in FIGS. 13A–13D, COS cells expressing B7-4 bound both human PD-1-Fc and murine PD-1-Fc, but did not bind CTLA4-Fc, Flt4-Fc, or human IgG. As a positive control, it was demonstrated that B7-1 expressing COS cells bound CTLA4-Fc, but not PD-1-Fc or IgG.

In addition, an in situ assay of transfected COS cell monolayers was performed. Monolayers were probed with PD-1Fe, CTLA4Fc or human IgG1 and binding was detected with a secondary antibody directed against the Fc portion and conjugated to alkaline phosphatase. Binding was visualized with chromogenic substrates 5-bromo-4-chloro-3-indolyl phosphate and nitro blue tetrazolium and light microscopy. In parallel, cells transfected with B7-4 were found to bind to PD-1-Fc, and not CTLA4-Fc (human Ig gamma 1) or Flt4-Fc, the extracellular region of murine Flt4 linked to human Ig gamma 1. In parallel, PD-1Fc did not bind the surface of mock-transfected, B7-1 or B7-2 transfected COS cells.

In another experiment, no binding of PD-1-Fc to soluble forms of B7-1 or B7-2, and binding to B7-4, was detected using a BIACORE-based assay. In parallel, hCTLA4 was shown to bind to B7-1 and not to B7-4. PD-1-Fc or CTLA4-Fc was immobilized and conditions were essentially as described by Fitz et al. (1997) *Oncogene* 15:613). Concentrated COS cell medium from cells that had been transfected with full length B7-4M or B7-4-Fc was injected and interactions were measured using real-time Biomolecular Interaction Analysis (BIA) (Sjolander, S. and Urbaniczky, C. (I 991) *Anal. Chem.* 63:2338–2345 and Szabo et al. (1995) *Curr. Opin. Struct. Biol.* 5:699–705). Human B7-4 was found to bind human and mouse PD-1 and this binding was inhibited by competition with a coinjected PD-1-Fc, but not CTLA4-Fc. These experiments demonstrate not only the binding of soluble B7-4-Fc fusion protein to immobilized PD-1-Fc, but also demonstrate the presence of a soluble form of B7-4 in the conditioned medium of B7-4M cDNA transfected cells, presumably as a result of shedding.

FIGS. 14A–14F illustrate the ability of PD-1 and not Flt4 (the receptor for vascular endothelial growth factor C) to competitively inhibit the binding of PD-1 to B7-4. The binding of human PD-1 gamma 2a fusion protein to COS cells expressing B7-4M is shown in Panel A. The binding was detected with anti-gamma 2a specific reagents linked to PE. Human PD-1 linked to IgG1 was added at: 50 µg/ml, 6.25 µg/ml, 100 µg/ml, or 25 µg/ml and was found to compete for binding. As a control, Flt4IgG1 at 100 µg/ml was not found to compete for binding of PD-1 to B7-4.

Figure 16:
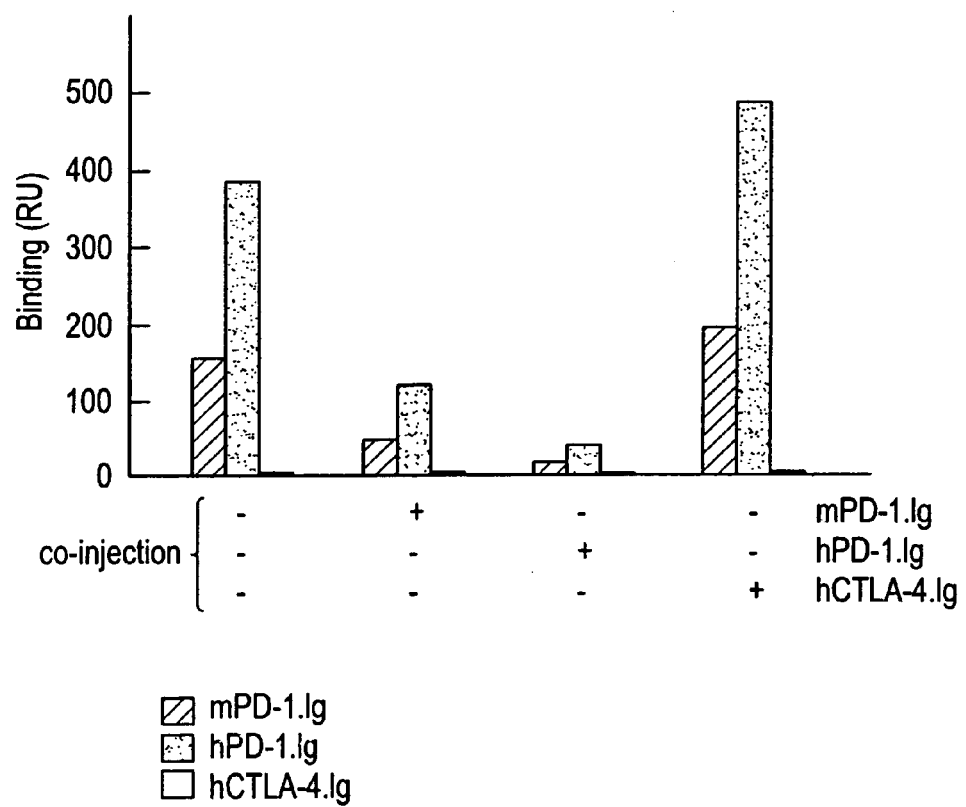
FIG. 16 illustrates the ability of PD-1 to bind to B7-4 transfected CHO cells, as determined by BIACORE analysis.

In yet another experiment, the ability of B7-4 to bind to PD-1 was determined by flow cytometry and BIACORE-binding assays. Human and murine PD-1.Ig fusion proteins bound to both human and murine B7-4 expressed on CHO cells, as detected by flow cytometry (FIGS. 15A–15F). However, neither human CTLA-4.Ig, human CD28.Ig, nor human ICOS.Ig bound to either B7-4 expressing cell line. The PD-1 fusion proteins did not bind CHO cells transfected with vector alone. Further confirmation of the PD-1:B7-4 interaction was obtained using surface plasmon resonance with a BIACORE instrument. The human and murine PD-1.Ig proteins and human CTLA-4.Ig were immobilized on the flow cell surfaces of a dextran chip and tested for binding to soluble human B7-4.Ig. B7-4.Ig bound to both human and murine PD-1.Ig, but not to human CTLA-4.Ig (FIG. 16). This binding was blocked by competition with co-injected soluble PD-1.Ig, but not CTLA-4.Ig. Soluble forms of human B7-1 and B7-2 did not bind immobilized human PD-1.

BIACORE analysis was also used to analyze PD-1.Fc: B7-4.Fc binding kinetics. A BIA 2000, CM5 sensor chip was used. NHS/EDC immobilization was used to bind 50–150 RU PD-1.Fc to the chip. The surface was conditioned with 20 injections of ionic regeneration buffer (30% 1.83 M $MgCl_2$, 0.46 M KSCN, 0.92 M Urea, 1.83 M guanidine-HCl). The running buffer was PBS (phosphate buffered saline) with 3.4 mM EDTA, 0.005% Tween-20, and 100 µg/ml BSA (bovine serum albumin) at 25° C. The reference surfaces used were (1) blank activation (NHS/EDC) followed by ethanolamine block and (2) mutated mIgG2a. The concentration of B7-4.Fc used (undetectable multimer, determined by SEC) was determined by ELISA and BCA protein assay (Pierce). The range of B7-4.mFc used was 20 nM to 2 µM. The flow rate was 60 µl/minute. Association was for 3–4 minutes with 4 minutes dissociation. Injections were done in triplicate and randominzed. Analysis was done using BIAevaluation software, with 1:1 Langmuir and global analysis. The results of the analysis showed that hPD-1.Fc:hB7-4.Fc binding fit a 1:1 model. The kinetic rate constant ($K_D$) calculated for hPD-1.Fc:hB7-4.Fc was 186 nM ($k_{on}$=6.57±1.2 Xe4 $M^{-1}s^{-1}$; $k_{off}$=0.122±0.0007 $s^{-1}$).

These data demonstrate that PD-1 binds B7-4, and that this interaction may regulate the action of PD-1.

Example 12

B7-4 Can Transmit a Negative Signal to Immune Cells

Figure 17:
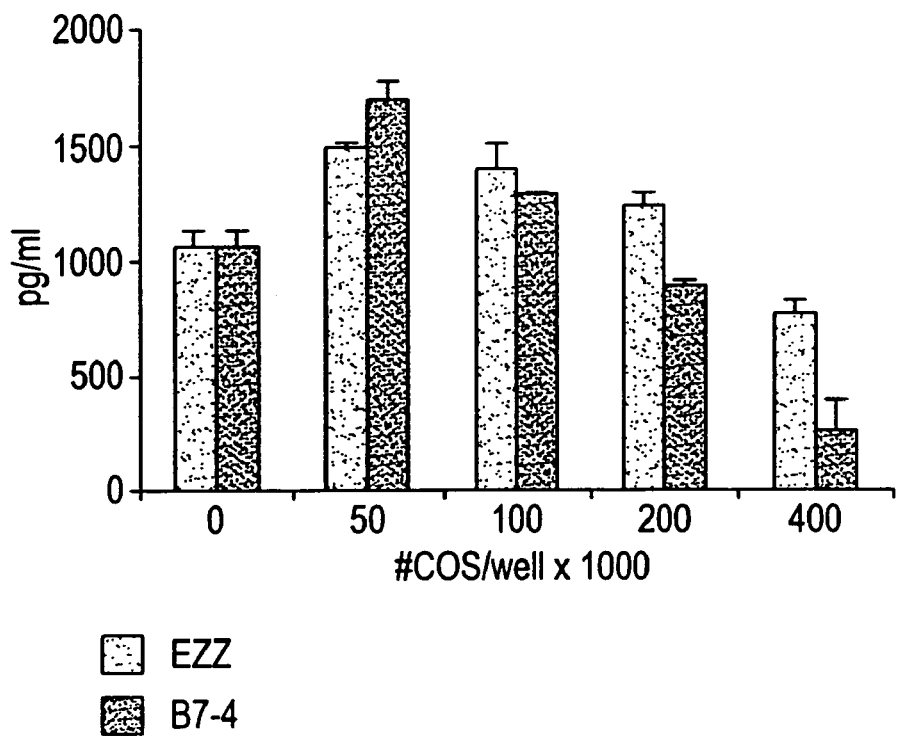
FIG. 17 illustrates the ability of B7-4M to transmit a negative signal to T cells.

In this example, $5\times10^5$ Jurkat T cells per well were stimulated with anti-CD3 coated beads (at a 1:1 ratio) and soluble anti-CD28. COS cells expressing B7-4 or a negative control, called EZZ, were titrated into the wells. Supernatants were harvested at 48 hours and assayed by ELISA for human IL-2. FIG. 17 shows that increasing numbers of COS B7-4 cells (bars on the right in the figure) lead to a decrease in IL-2 production.

Using similar assay formats, for example in which human PHA-blasts from PBMCs were stimulated with immobilized anti-CD3 and soluble anti-CD28, a decrease in T-cell proliferation was observed by titrating in COS cells expressing B7-4.

Example 13

The PD-1:B7-4 Interaction Inhibits CD3-mediated T-Cell Proliferation, Cytokine Production, and Expression of T Cell Activation Markers To examine the functional significance of the PD-1:B7-4 interaction, the functional consequences of B7-4 interaction with its receptor were also examined using human T-cells. Peripheral blood mononuclear cells were isolated by Ficoll-Hypaque gradient centrifugation. $CD4^+$ T cell populations (85–90% purity) were purified by negative selection using a cocktail of monoclonal antibodies and immunomagnetic beads (PerseptiveBiosystems). Anti-CD3, control IgG and fusion protein were covalently attached to polyurethane-coated tosyl activated Dynabeads (Dynal) according to manufacturer's instructions and as described previously (Blair, P. J. et al. (1998) *J. Immunol.* 160:12–15). Anti-CD3 antibody (UCHT1, Pharmingen) at the indicated concentration was added to $1\times10^7$ beads/ml 0.1 M phosphate buffer pH 7.4. Control IgG was added to the bead suspension in order to maintain a constant total Ig concentration of 5 µg/ml during binding. Similarly, anti-CD3/B7-4.Ig(γ2a) beads were prepared with the indicated anti-CD3 antibody concentration, a constant concentration of either B7-4.Ig representing 40% of the total bound protein (2 µg/$10^7$ beads), and control IgG to make up the remaining total bound protein. $10^5$ T cells were cultured in 96 well flat-bottom plates, and beads were added at a 1 bead to 1 cell ratio in the presence or absence of the indicated concentrations of anti-CD28 antibody (CD28.2, Pharmingen). Proliferation was determined by labeling cultures for the last 6 hr of a 4-day assay with 1 µCi $^3$H-thymidine/well. For analysis by cytokine ELISAs, cultures were set up as described above and supernatants harvested at the indicated times. Interferon-γ, IL-10 and IL-2 concentrations were determined using commercially available ELISA kits (Genzyme).

Purified $CD4^+$ T-cells obtained from peripheral blood mononuclear cells (PBMC) were activated with beads coated with anti-CD3 mAb and either human B7-4.Ig or a control Ig. Proliferation and cytokine production was assessed 96 hours after stimulation. Cells activated with anti-CD3 mAb/B7-4.Ig coated beads showed a 69% decrease in proliferation relative to anti-CD3 mAb/control Ig activated cells (FIG. 18A). Proliferation was inhibited in a dose dependent manner when different concentrations of B7-4.Ig coated beads were used (0.25, 0.5, 1, and 2 µg B7-4.Ig/$10^7$ beads).

Furthermore, activation of cells in the presence of B7-4 also impaired cytokine secretion. In the presence of B7-4, interferon-γ (FIG. 18B) and IL-10 (FIG. 18C) secretions were decreased by approximately 80% and 60%, respectively. IL-2 production was below detection under these activation conditions at both 24 and 96 hr. However, activation of T cells using beads as in Example 14 below showed that B7-4 could inhibit IL-2 production at 2, 3, and 4 days of stimualation. B7-4 also inhibited IL-2 production in Jurkat T cells at beads:cell ratios of 1:1, 2:1, and 4:1. Furthermore, under conditions in which costimulation in the form of soluble anti-CD28 was provided, activation of cells in the presence of B7-4 also led to a decrease in IL-2 production. PD-1:B7-4 interaction also led to a decrease in both IL-10 and IFN-γ production. Thus, activation of murine and human T-cells in the presence of B7-4 leads to inhibition of both proliferation and cytokine secretion.

Further experiments showed that activation of T cells in the presence of B7-4 results in decreased expression of T cell activation markers. For example, when T cells were activated in the presence of B7-4, and the expression of the early activation marker CD69 examined by flow cytometry, the results were as follows (% positive for CD69 expression):

| % CD69+ | anti-CD3 | anti-CD3/B7-4.Fc | Media |
|---|---|---|---|
| 24 hours | 26% | 26% | 1% |
| 48 hours | 46% | 36% | 2% |
| 72 hours | 63% | 42% | 5% |

When T cells were activated in the presence of B7-4, and the expression of IL-2R (CD25) examined by flow cytometry, the results were as follows (% positive for IL-2R expression):

| % IL-2R+ | anti-CD3 | anti-CD3/B7-4.Fc | Media |
|---|---|---|---|
| 24 hours | 17% | 12% | 2% |
| 48 hours | 29% | 17% | 4% |
| 72 hours | 54% | 15% | 5% |

Example 14

PD-1:B7-4 Inhibition Kinetics Correlate With PD-1 Expression

This example describes the correlation between the timing of PD-1 expression during T cell activation and the ability of B7-4 to inhibit T cell proliferation. T cell activation was achieved using tosyl-activated beads ($10^7$) coated with 3 µg anti-CD3 and 2 µg of either control Fc (ctrl.Fc) or mB7-4.Fc fusion protein. $5 \times 10^4$ purified Balb/c LN T cells were stimulated with $1 \times 10^5$ beads in a 96 well plate format. For proliferation, plates were pulsed for the final ~10 hours of the culture period. For IL-2 ELISAs, supernatents were harvested from parallel wells.

To determine the kinetics of PD-1 expression during T cell activation, purified Balb/c LN T cells were stimulated with anti-CD3/ctrl.Fc beads. At 0, 1, 2, 3, 4, and 5 days of stimulation, cells were harvested, washed, and stained using biotinylated anti-murine PD-1 (made from monoclonal antibody J43, described in Agata, Y. et al. (1996) *Int. Immunol.* 8:765–72) or biotinylated hamster control, followed by PE-Streptavidin. Data were calculated for live-gated cells, and the percent positive were calculated relative to isotype control. PD-1 expression increased over the course of time during T cell activation as follows: Day 0 (0%); Day 1 (27%); Day 2 (37%); Day 3 (40%); Day 4 (74%); and Day 5 (83%).

When proliferation of Balb/c LN T cells activated using either anti-CD3/ctrl.Fc beads or anti-CD3/mB7-4.Fc was compared, the kinetics of the B7-4 inhibition of T cell proliferation correlated with the expression kinetics of PD-1, providing further evidence that B7-4 acts to inhibit T cell activation via its interaction with PD-1.

Example 15

Figure 19A:
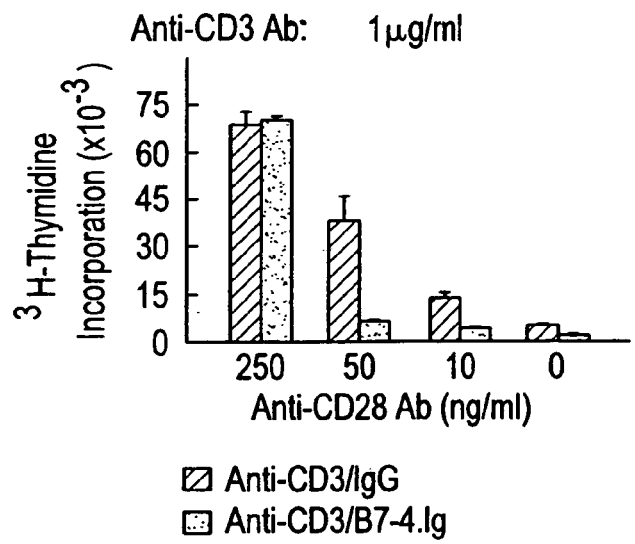
FIGS. 19A–19B illustrate that T cell receptor/B7-4 activation in the presence of CD28 costimulation results in inhibition of T cell proliferation.
Figure 19B:
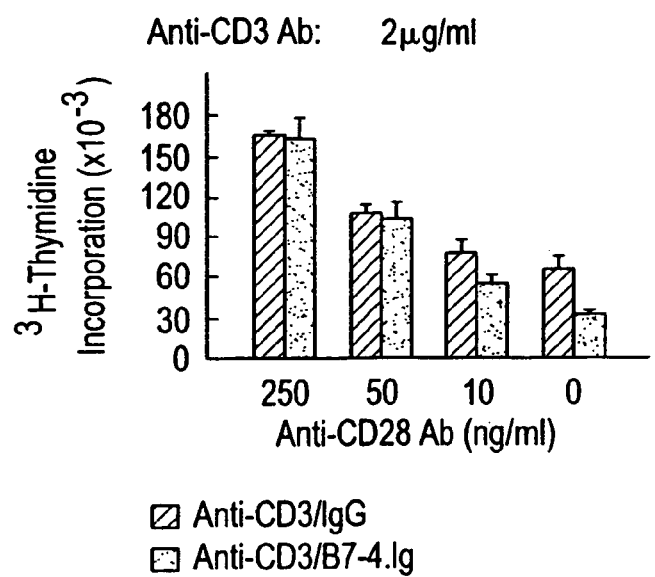

The Outcome of PD-1:B7-4 Interaction Depends on the Strength of T-cell Receptor and CD28 Signals To examine the relationship between T-cell receptor, CD28 and PD-1 mediated signals, human CD4+ T-cells were stimulated with suboptimal or optimal concentrations of anti-CD3 mAb, a fixed concentration of B7-4.Ig and increasing concentrations of soluble anti-CD28 mAb. Using anti-CD3 mAb-coated beads, the concentrations required for suboptimal and optimal T-cell stimulation were established. Under conditions of suboptimal T-cell receptor engagement (anti-CD3 mAb at 1 µg/ml), minimal proliferation was observed in the absence of costimulation (FIG. 19A). Addition of increasing concentrations of soluble anti-CD28 mAb led to an up to 30-fold increase in proliferation. Under these conditions, activation of T cells in the presence of B7-4 resulted in an 80% reduction in proliferation (FIG. 19A). A maximal level of costimulation (anti-Cd28 at 250 ng/ml) was required to rescue the inhibition of proliferation mediated by B7-4 stimulation. In contrast, under saturating conditions of T-cell receptor activation (anti-CD3 mAb at 2 µg/ml), B7-4 mediated inhibition of T-cell proliferation was only observed in the absence of CD28 costimulation (FIG. 19B).

To examine the ability of costimulation to rescue the PD-1:B7-4 mediated inhibition of proliferation at different time points during T cell activation, Balb/c LN T cells were stimulated as in Example 14 in the presence or absence of 1 µg/ml soluble anti-CD28. Proliferation was measured on days 2, 3, and 4. Anti-CD28 reverses PD-1:B7-4.Fc mediated inhibition at early (day 2), but not late (days 3 and 4) timepoints of T cell activation. Reversal of inhibition was dose-dependent and seen across a range of anti-CD28 concentrations (160 ng/ml, 800 ng/ml, 1 µg/ml, 4 µg/ml, and 20 µg/ml). Under the same conditions of strong costimulation (1 µg/ml anti-CD28), however, B7-4.Fc inhibits IL-2 production at all time points examined (days 2, 3, and 4). B7-4.Fc also inhibits IL-2 production across a broad range of soluble anti-CD28 costimulation (100 ng/ml, 160 ng/ml, 500 ng/ml, 800 ng/ml, 4 µg/ml, 5 µg/ml, 10 µg/ml, and 20 µg/ml).

ICOS mediated costimulation also rescues PD-1:B7-4 medidated inhibition of proliferation.

Example 16

Ability of B7-4 To Inhibit CD28 Signals and Cytokine Production

The inhibitory effects of the PD-1:B7-4 pathway appear to be determined by the strength of signal through the TCR and CD28 (see previous example), whereby weak CD3/CD28-mediated responses are easily downregulated. To study the interaction of the CD28 signal and the PD-1:B7-4 pathway, pre-activated DO11.10 CD4+ T cells were activated with OVA peptide presented by CHO-IA$^d$/B7.2 or CHO-IA$^d$/B7.2/B7-4.

For detection of B7-4, $5 \times 10^4$ CHO transfectants cells were incubated with 5 µg/ml of human PD-1Ig (hPD-1-Ig) (Genetics Institute, Cambridge, Mass.) and developed with goat anti-murine IgG2a-phycoerythrin (PE) (Southern Biotechnology Associates Inc., Birmingham, Ala.). In addition, cells were stained separately with 5 µg/ml anti-IA$^d$-PE or B7.2-PE (Pharmingen, San Diego, Calif.). Following each step, cells were washed three times with PBS/1% BSA/0.02% sodium azide. After the final incubation, cells were fixed with 1% paraformaldehyde. Ten thousand events were analyzed on a FACSCalibar (Becton Dickinson, Mountain View, Calif.). All isotype controls were obtained from Pharmingen.

Splenocytes were prepared from DO11.10 mice and treated with Tris-NH$_4$Cl to deplete erythrocytes. Cells were cultured with 1 µg/ml of OVA peptide for 72 hours (Analytical Biotechnology Services, Boston, Mass.) in RPMI 1640 (Life Technologies, Grand Island, N.Y.) supplemented with 10% FCS (Sigma, St Louis, Mo.), 2 mM L-glutamine, 100 U/ml penicillin, 100 µg/ml streptomycin, 250 ng/ml amphotericin B, 10 mM HEPES, 50 µM 2-ME (all from Life Technologies) and 15 mg/ml of gentamicin (BioWhittaker, Walkersville, Md.). CD4$^+$ T cells were purified by positive selection using magnetic-activated cell sorting separation columns (Miltenyi Biotec, Auburn, Calif.) with resulting purity of >98%. Cells were rested overnight before re-stimulation.

Proliferation of CHO cells was inhibited by incubation with 50 µg/ml of mitomycin C (Bristol Laboratories, Princeton, N.J.) for 16 hours at 37° C. At the end of the incubation period, the cells were harvested with 10 mM EDTA in PBS, washed twice and left on ice for 1 hour. The cells were subsequently washed three times and resuspended in culture medium. $10^5$ pre-activated CD4$^+$ T cells were cultured with varying concentrations of OVA peptide and $10^4$ mitomycin C-treated CHO transfectants in 96 well plates. To assay proliferation, cultures were incubated for 48 hrs and pulsed with 1 µCi/well of [$^3$H] thymidine (New England Nuclear, Boston, Mass.) for the last 6 hours of the incubation period.

Figure 20I:
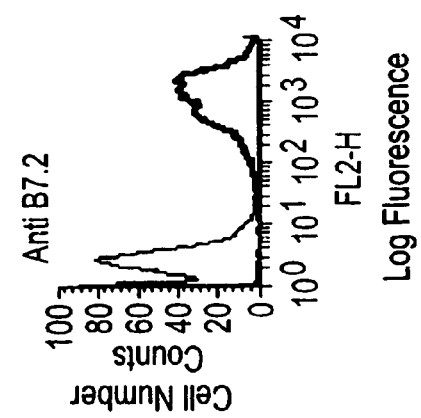
Figure 20H:
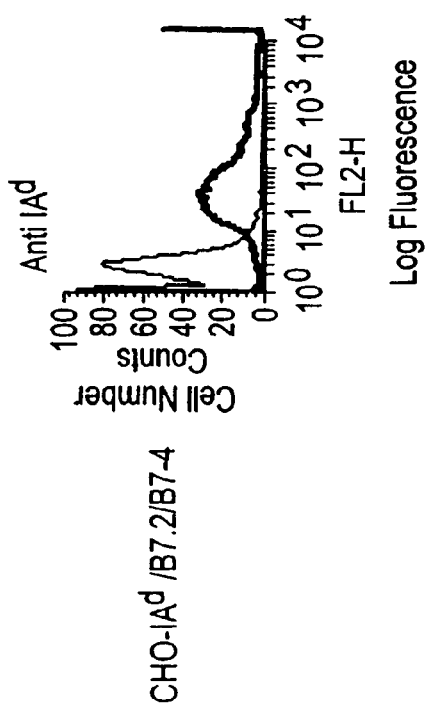
Figure 21A:
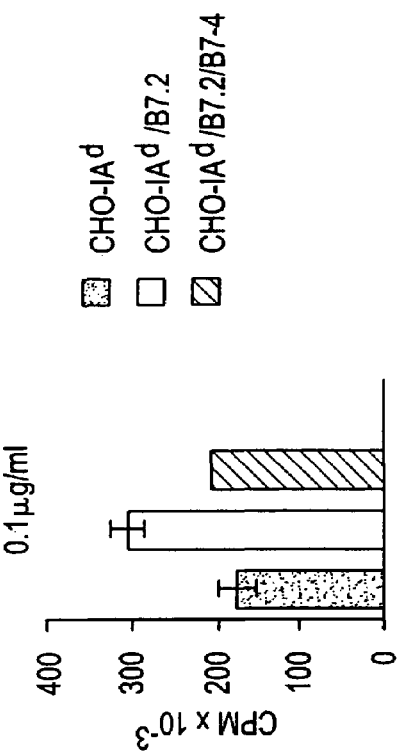
FIGS. 21A–21D illustrate the action of B7-4 in the inhibition of CD28 signals.
Figure 21B:
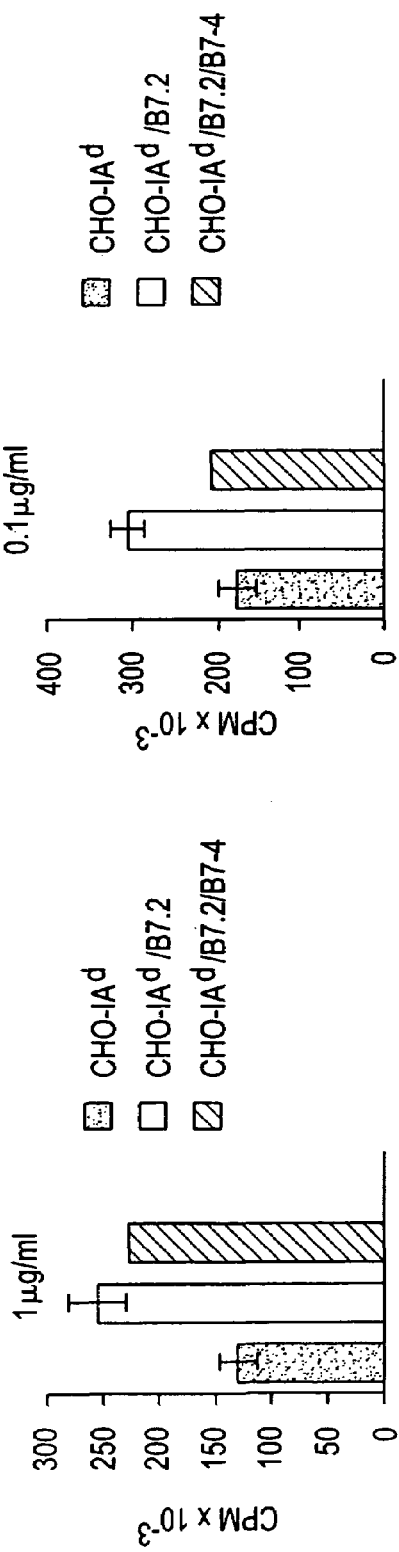
Figure 21C:
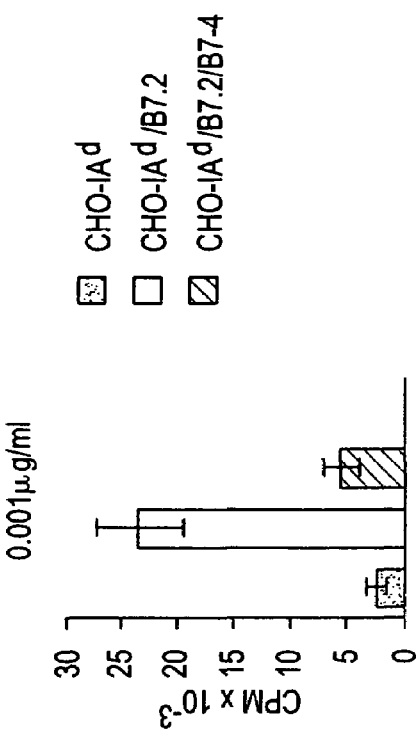
Figure 21D:
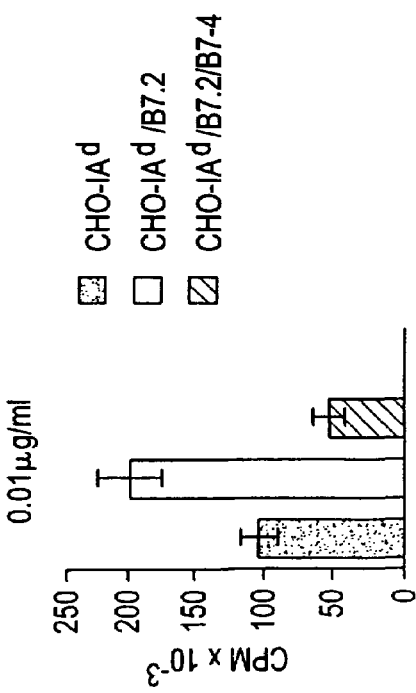

The expression of B7 and IA$^d$ was similar on all CHO transfectants (FIG. 20). As expected, introduction of B7.2 led to an increase in proliferative responses by T cells at all antigen concentrations (FIGS. 21A–21D). However, B7-4 inhibited responses at lower peptide concentrations (0.01 µg/ml and 0.001 µg/ml) (FIGS. 21C and 21D, respectively).

Figure 23A:
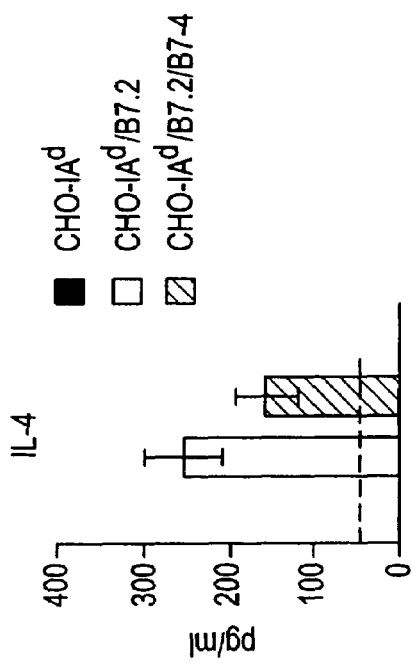
FIGS. 23A–23C illustrate the inhibition of cytokine production by the PD-1:B7-4 pathway, as measured by cytokine mRNA levels.
Figure 23B:
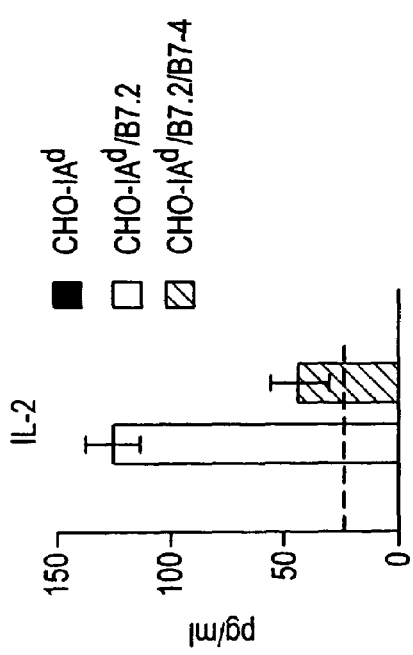
Figure 23C:
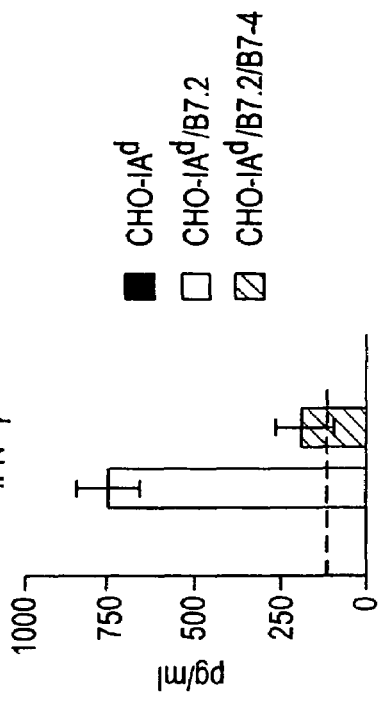

To address the capacity of PD-1:B7-4 pathway to inhibit cytokine production, supernatants from DO11.10 CD4$^+$ T cells activated with OVA peptide presented by CHO cell transfectants were analyzed. Aliquots of supernatants were harvested at various times after initiation of cultures. IL-2, IL-4, IFN-γ and IL-10 levels were analyzed using mAbs and recombinant cytokine standards from Pharmingen. Detection limits were as follows: IL-2, 20 pg/ml, IL-4, 40 pg/ml. IFN-γ, 100 pg/ml and IL-10, 200 pg/ml. Production of IL-2 (FIG. 22A), IL-4 (FIG. 22B), IFN-γ (FIG. 22C), and IL-10 (FIG. 22D) was inhibited significantly when DO11.10 CD4$^+$ T cells were cultured with 0.1 µg/ml peptide and B7-4. At this concentration there was only a weak inhibition of proliferation. However, B7-4 significantly inhibited cytokine production at 0.01 µg/ml peptide, consistent with the inhibition of proliferation (FIGS. 23A–23C). IL-10 was not detected under these activation conditions. Therefore, PD-1 engagement by B7-4 can downregulate cytokine production even when T cell proliferation is not affected.

To determine whether the diminished cytokine production was due to reduced mRNA levels, and RNase protection assay was utilized. CD4$^+$ T cells were restimulated with various CHO cell transfectants and 0.01 µg/ml OVA peptide. After 48 hours, cells were harvested and mRNA was isolated using TRIzol® reagent (Life Technologies). 5 µg mRNA was analyzed for cytokine levels by RNase protection assay using RiboQuant multiprobe kit mCK1 according to the manufacturer's instructions (Pharmingen). Transcript levels of IL-4, IL-10, IL-13, IL-2, IL6 and IFN-γ mRNA were detected in pre-activated DO11–10 CD4$^+$T cells after stimulation with 0.01 µg/ml OVA peptide presented by CHO-IA$^d$/B7.2. However, the introduction of B7-4 significantly reduced cytokine mRNA levels. There was minimal upregulation of mRNA for cytokines in unstimulated T cell cultures or T cells activated with peptide presented by CHO-IA$^d$. These results further demonstrate the capacity of the PD-1:

B7-4 pathway to antagonize a strong B7/CD28 signal at least when antigenic stimulation is weak or limiting, and the inhibition of at least cytokine production in conditions of strong antigenic stimulation.

Example 17

Mechanism of Action of the PD-1:B7-4 Pathway

Cross-linking of CTLA-4 has been shown to inhibit cell cycle progression in naïve T cells (Krummel, M. F. and Allison, J. P. (1996) *J. Exp. Med.* 183:2533–2540; Walunas, T. L. et al. (1996) *J. Exp. Med.* 183:2541–2550). As PD-1 was isolated from murine cell lines undergoing apoptosis, a possible mechanism of action of the PD-1:B7-4 pathway might be to increase programmed cell death. To address this issue, DO11.10 CD4$^+$ T cells were restimulated with 0.01 µg/ml peptide and various CHO transfectants and cell cycle progression was analyzed. CD4$^+$ T cells were restimulated with 0.01 µg/ml peptide as described previously. After 36 hours of culture, cells were recovered and stained with anti CD4-FITC. Cells were washed in PBS, fixed in 70% ethanol for 1 hour on ice and then resuspended in PBS containing 10 µg/ml RNase (Sigma) and 50 µg/ml propidium iodide (Sigma). Analysis was performed within an hour of staining.

Figure 24A:
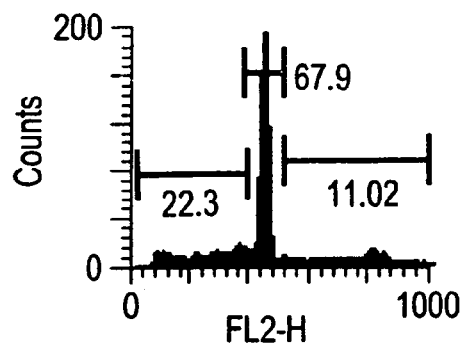
FIGS. 24A–24C illustrate that the mechanism of action of the PD-1:B7-4 pathway is cell-cycle arrest.
Figure 24B:
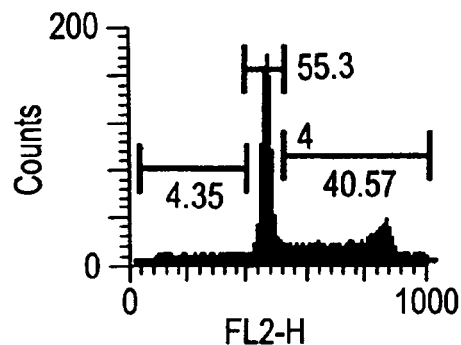
Figure 24C:
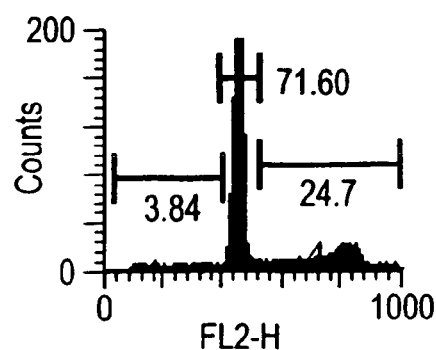

After 48 hours, cells were recovered and stained with CD4-FITC. After permeabilization, cells were incubated with propidium iodide to analyze the $G_0/G_1$, $S/G_2$ and sub-diploid populations. CD4$^+$ T cells restimulated with peptide presented by CHO-IA$^d$ have a large proportion of cells in the sub-diploid population, indicative of apoptosis (FIG. 24A). In cultures where CD4$^+$ T cells were stimulated by peptide presented by CHO-IA$^d$/B7-2, there were increased number of cells in the $S/G_2$ phase, and a decreased number in the sub-diploid population (FIG. 24B), indicating that cells were in cycle and rescued from apoptosis by B7/CD28 costimulation. The introduction of B7-4 led to an increased number of cells in the G0/G1 phase (FIG. 24C). There were comparable levels of apoptosis in the B7-4 cultures to the CHO-IA$^d$/B7 cultures. This was confirmed by annexin staining. The inhibition of cell progression by the PD-1:B7-4 pathway confirms its role in downregulating T cell activation.

Further experiments using PD-L1.Fc confirmed that PD-1:B7-4 engagment on T cells does not lead to apoptosis. Cells were treated with anti-CD3 or anti-CD3/B7-4.Fc, or irradiated, stained with propidium iodide and annexin, and analyzed by flow cytometry. Apoptotic cells were identified as those that were positive for both propidium iodide and annexin. Controls done in parallel showed that anti-CD3/B7.4.Fc inhibited proliferation at 48 and 72 hours. There results were as follows:

| % apoptotic | anti-CD3 | anti-CD3/B7-4.Fc | Irradiated |
| --- | --- | --- | --- |
| 24 hours | 3% | 3% | 18% |
| 48 hours | 5% | 4% | 25% |
| 72 hours | 10% | 12% | 42% |

Still further experiments analyzing DNA content demonstrated that activation of T cells in the presence of B7-4.Fc results in cell cycle arrest. T cells were stimulated with ctrl.Fc or mB7-4.Fc beads. On day 4, the percentage of dividing cells was determined by propidium iodide staining. T cells stimulated with mB7-4.Fc showed half (11% vs. 21% for the control) the number of cells with the increased DNA content indicative of dividing cells. In two other experiements, the percentages were similar: 14% vs. 28% and 11% vs. 24%.

Analysis of mitosis was also examined. T cells were labeled with CSFE and stimulated with ctrl.Fc or mB7-4.Fc beads as in Example 14. At days 1, 2, 3, and 4, FACS analysis was done. Only live-gated events were analyzed. Percentages are for non-dividing cells. As the following data indicates, treatment with B7-4 inhibits cell division:

| % non-dividing | Day 1 | Day 2 | Day 3 | Day 4 |
|---|---|---|---|---|
| Ctrl.Fc | 87.4% | 32.4% | 11.9% | 3.8% |
| mB7-4.Fc | 87.7% | 46.7% | 35.1% | 24.5% |

Figures 28A, 28B:
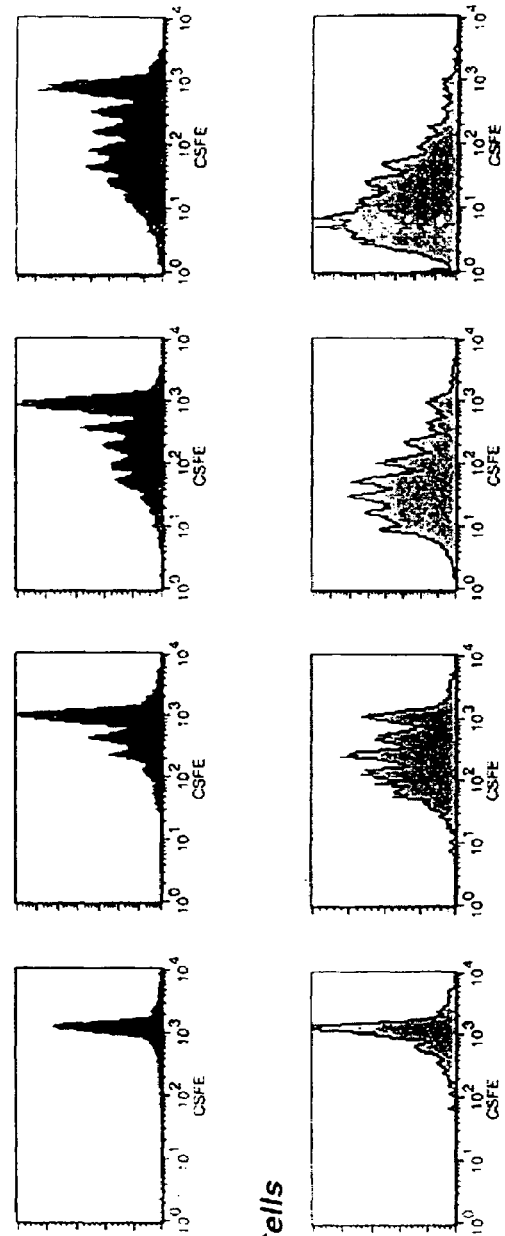
FIGS. 28A–28B illustrate the effect of PD-1:B7-4 interaction on mitotic cell division. T cells were labeled with CSFE and stimulated with ctrl.Fc or mB7-4.Fc beads. At the indicated time points, FACS analysis was done. Live-gated events are depicted.

Mitosis was also examined (as above) separately for CD4+ T cells and CD8+ T cells. The results are set forth in FIGS. 28A (CD4+) and 28B (CD8+).

Example 18

IL-2, Induced By Costimulation or Added Exogenously, Can Overcome Proliferative Inhibition Induced By PD-1:B7-4 Interaction Purified Balb/c LN T cells were stimulated as in Example 14 in the presence or absence of 1 μg/ml soluble anti-CD28 and 10 μg/ml anti-IL-2. Proliferation was measured on day 2. In the presence of costimulation by anti-CD28, addition of anti-IL-2 restores PD-1:B7-4 mediated inhibition, suggesting that anti-CD28 reverses the inhibitory effect by inducing IL-2 production. Addition of anti-IL-2 also restores PD-1:B7-4 mediated inhibition in the presence of costimulation by ICOS ligand.

In another example, Balb/c LN T cells were stimulated as in Example 14 with the addition of exogenous IL-2. When proliferation was measured on day 3, exogenous IL-2 reverses PD-1:B7-4 mediated inhibition of proliferation in a dose-dependent manner (IL-2 concentration range: 3 pg/ml, 10 pg/ml, 30 pg/ml, 100 pg/ml, and 300 pg/ml). Moreover, addition of exogenous IL-2 (at U/ml rhIL-2) reverses PD-1:B7-4 mediated inhibition of proliferation at all time points (proliferation measured on days 2, 3, 4, and 5).

Example 19

CD8+ T Cells Are More Susceptible to Inhibition By B7-4

This example describes the differences between CD4+ and CD8+ T cell activation in response to B7-4.

Figure 29A:
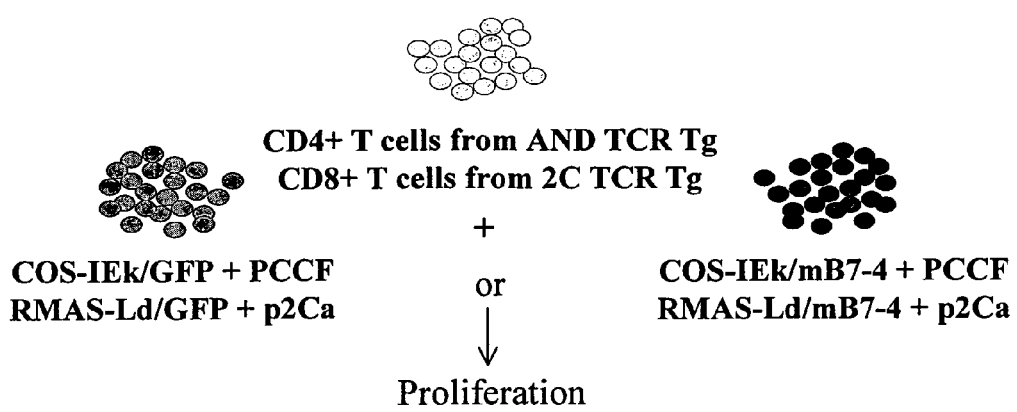
FIGS. 29A–29C illustrate the inhibition of both CD4+ and CD8+ T cells by PD-1:B7-4 interaction.
Figure 29B:
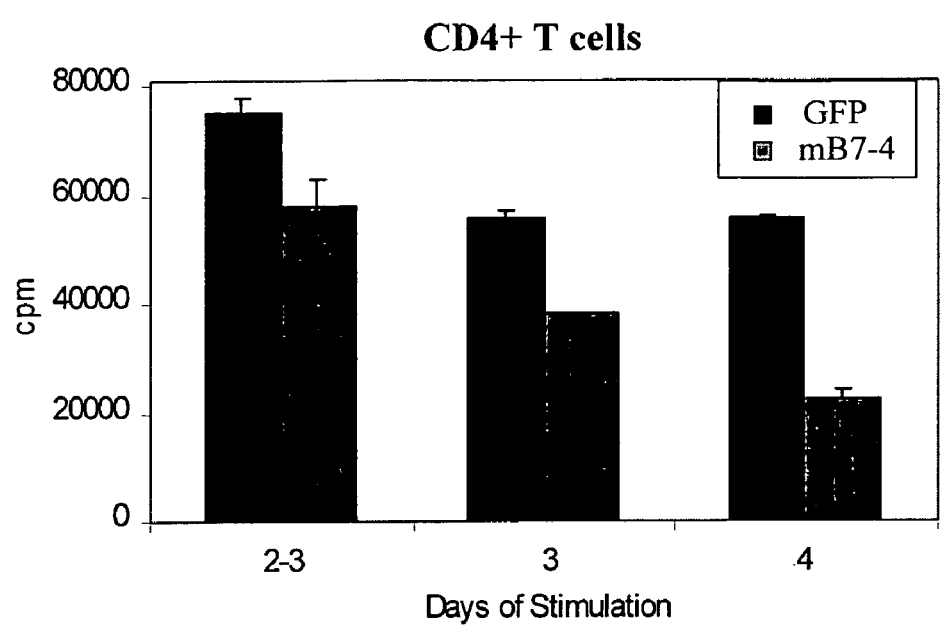
Figure 29C:
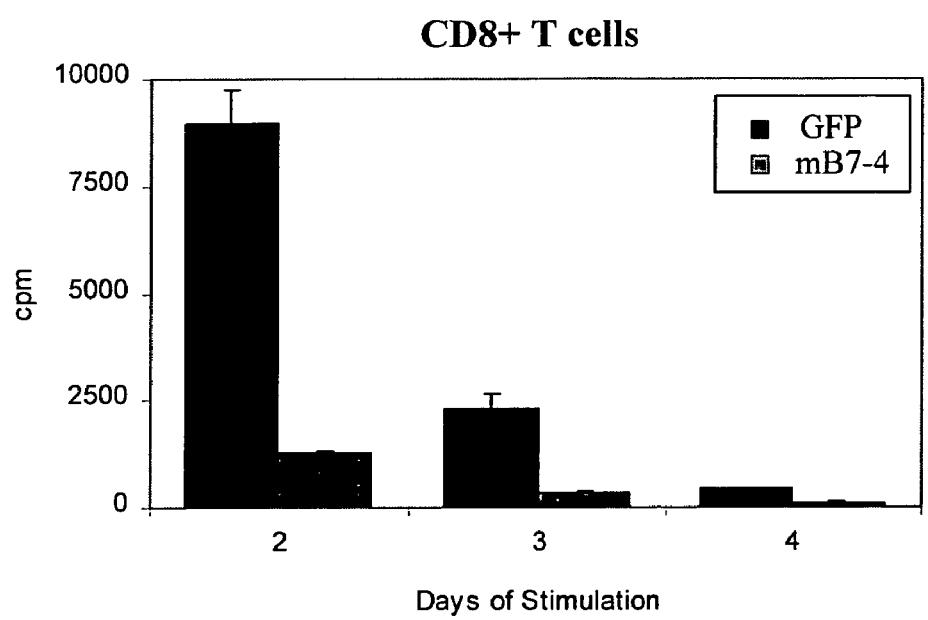

Stable antigen presenting cell (APC) lines were engineered to express GFP or mB7-4/GFP using retroviral technology. FIG. 29A shows a schematic of the cells used. For CD4+ T cell experiments, the APC:T cell ratio was 1:10 with 10 μM PCCF peptide. For CD8+ T cell experiments, the APC:T cell ratio was 1:1 with 1 mM p2Ca peptide. $5 \times 10^4$ purified LN T cells from TCR transgenic mice were stimulated with irradiated APC plus peptide for 2, 3, or 4 days. As shown in FIGS. 29B and 29C, both CD4+ and CD8+ T cells are inhibited by PD-1:B7-4 interactions.

Figure 30A:
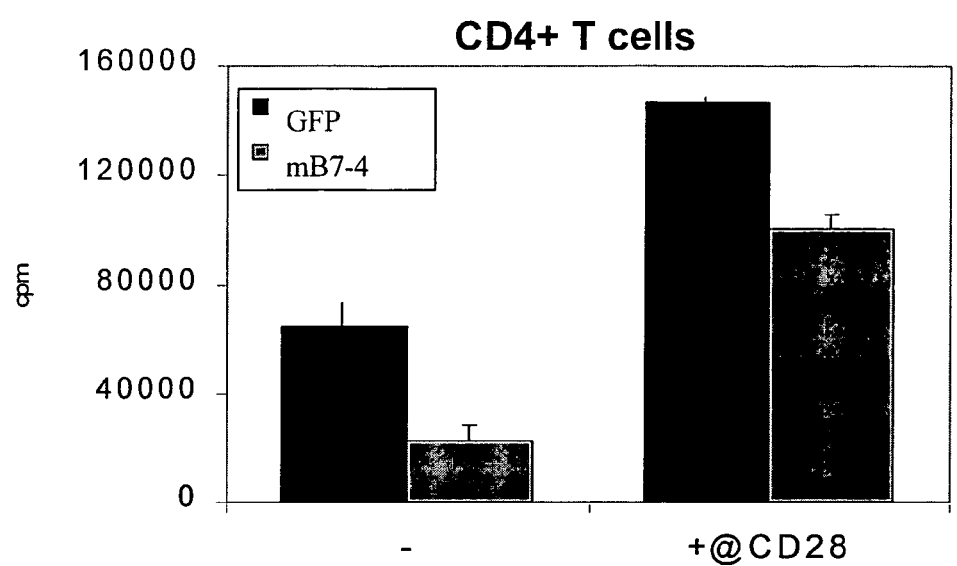
FIGS. 30A–30B illustrate the ability of costimulation to overcome the inhibition of CD4+ but not CD8+ T cell proliferation by PD-1:B7-4 interaction.
Figure 30B:
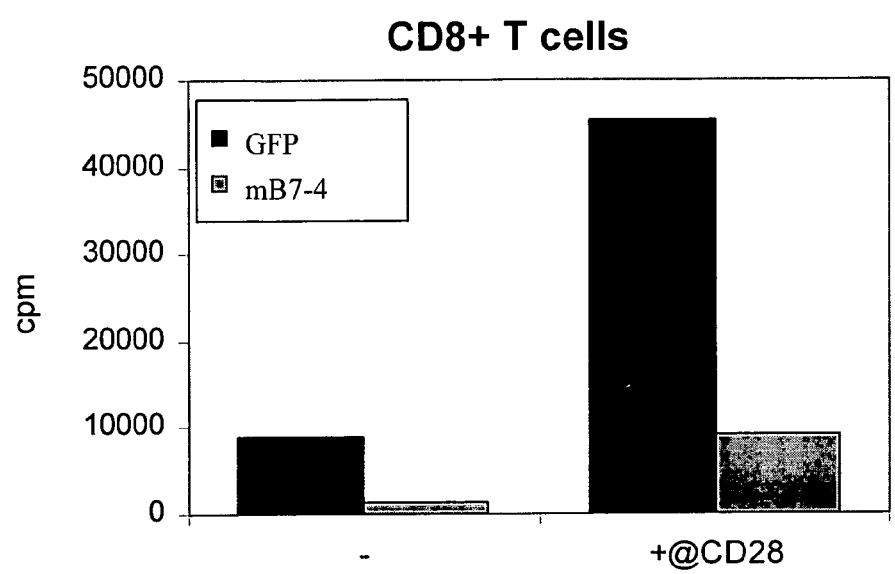

While addition of anti-CD28 can overcome PD-1:B7-4 mediated inhibition of proliferation of CD4+ T cells (FIG. 30A), it cannot overcome the inhibition of CD8+ T cells (FIG. 30B). Furthermore, either exogenous IL-2 or IL-15 (20 U/ml and 50 ng/ml, respectively, added on day 0) can overcome PD-1:B7-4 mediated inhibition of CD8+ T cells (proliferation measured on day 2). CD8+ T cells may be more susceptible to inhibition because of their intrinsic inability to produce IL-2.

Example 20

Recruitment of Signaling Molecules Through Engagement of the PD-1:B7-4 Signaling Pathway To further investigate the mechanism of action of the PD-1:B7-4 pathway in T cells, a Jurkat based system was used. Jurkat cells constitutively express low levels of PD-1. The Jurkat T cells were activated with beads coated with anti-CD3/ctrl.Ig or anti-CD3/hB7-4.Ig. Ligation of PD-1 plus CD3 leads to inhibition of IL-2 secretion by Jurkat cells, compared to cells stimulated with anti-CD3 alone. Cells were lysed and subjected to anti-SHP-2 immunoprecipitation, run on a gel, and transferred to a membrane. The membrane was immunoblotted with 4G10-HRP (horseradish peroxidase conjugated anti-phosphotyrosine antibody) and subsequently with anti-SHP-2 to confirm SHP-2 expression in the immunoprecipitates. With anti-CD3 and hB7-4.Ig., ligation of PD-1 plus the TCR rapidly resulted in the conversion of SHP-2 to the phosphorylated state, compared to TCR activation alone. SHP-1 was not phosphorylated under these conditions. This data indicates that recruitment of SHP-2 is a mechanism for downregulating TCR signaling events via the PD-1:B7-4 pathway.

Under similar experimental conditions, anti-Zap70 immunoprecipitation results in inhibition of Zap70 associated p23 pTyr upon coligation of CD3 and PD-1 (using anti CD-3 and B7-4.Ig). CD3ζ immunoprecipitation of Jurkat lysates and anti-pTyr blotting results in inhibition of CD3ζ phosphorylation upon coligation of CD3 and PD-1 (using anti CD-3 and B7-4.Ig). Inhibition of CD3ζ in this system persists with CD28 stimulation.

Example 21

Inhibition of Binding of Biotinylated Human B7-4 Fc to Human PD-1Fc

Fc fusion proteins were generated by linking the extracellular region of PD-1 or B7-4 to the hinge-CH2-CH3 domains of murine Igγ2a. Recombinant proteins were produced in COS cells transiently transfected with LipofectAMINE (Gibco-BRL) or stably transfected CHO cell lines and purified from conditioned media using protein A-Sepharose.

Figure 25A:
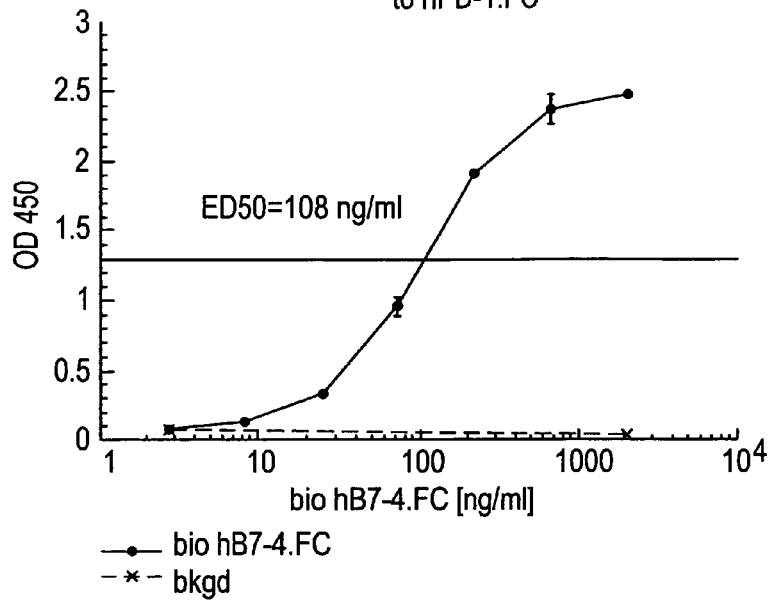
FIGS. 25A–25B illustrate the ability of antibodies to B7-4 to inhibit the interaction between B7-4 and PD-1.

The ability of antibodies to B7-4 or PD-1 to inhibit the interaction of human B7-4Fc and human PD-1 Fc was tested using standard ELISA methods. Briefly, human PD-1Fc molecules were immobilized in 96-well plates, blocked, and washed. Biotinylated B7-4Fc molecules (100 ng/ml) were added to wells at concentrations of approximately 2000, 700, 200, 70, 25, 8, and 1.18 ng/ml (FIG. 25A). The wells were incubated with Streptavidin conjugated horse radish peroxidase, washed, and color was developed using standard methods. The ED50 of B7-4Fc was found to be 108 ng/ml.

Figure 25B:
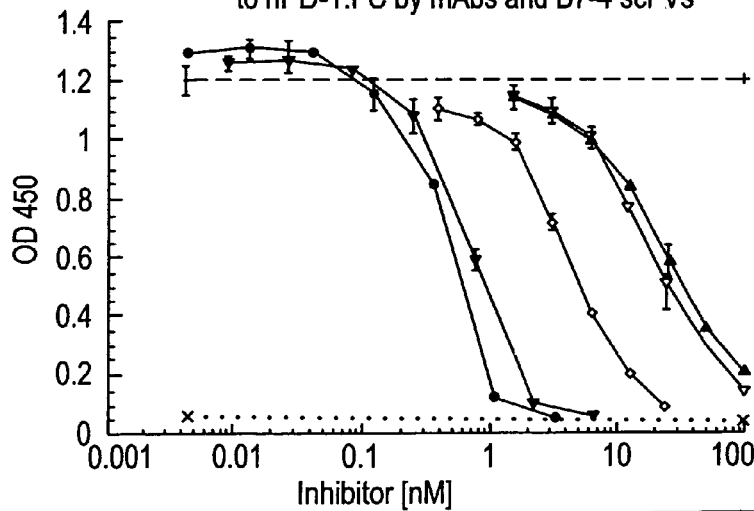

The ability of murine antibodies to human B7-4 (10D9 and 11D12) or scFv portions of human immunoglobulins (B7-4-1, B7-4-6, and B7-4-12) to inhibit the binding of biotinylated human B7-4Fc to human PD-1Fc was tested at 7 concentrations of inhibitors. The IC50 was found to range from 0.5 nM to 24 nM and the data are presented in FIG. 25B.

Figure 26:
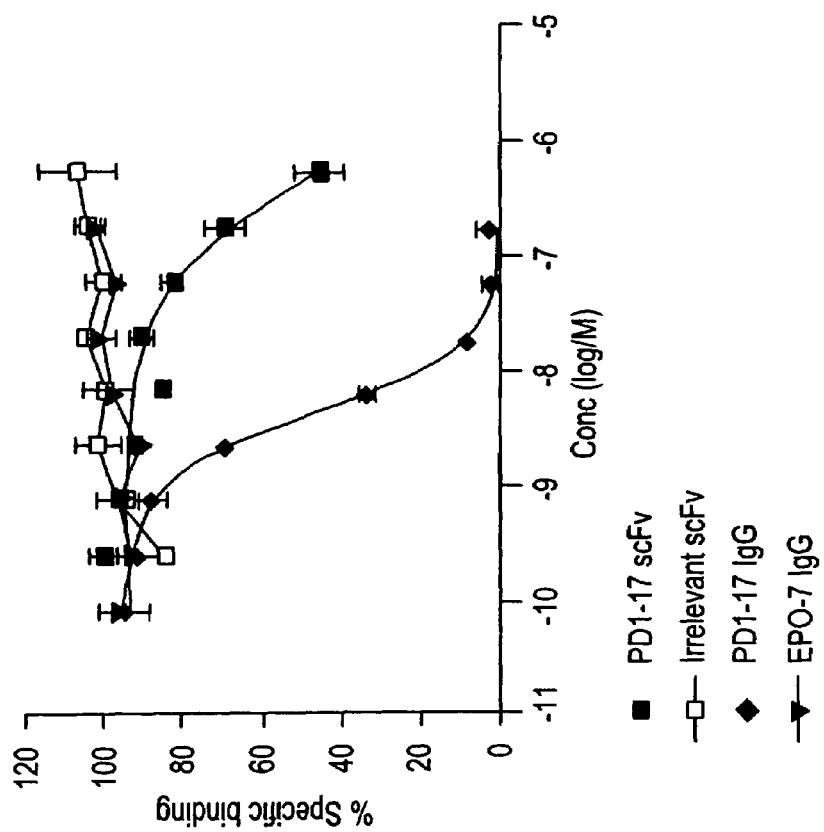
FIG. 26 illustrates the ability of antibodies to PD-1 to inhibit the interaction between B7-4 and PD-1.

The PD-1 specific scFv were also tested for their ability to inhibit the binding of B7-4 Fc to PD-1Fc using the same ELISA methods described above. Human scFv reactive with PD-1 (PD1–17 scFv) were found to inhibit specific binding (EC50 between $10^{-7}$ and $10^{-8}$) as shown in FIG. 26. $V_L$ and $V_H$ domains of the PD1-17scFv were used to generate a complete IgG. In brief, the VH and VL coding regions were linked to genomic CH and CL gene sequences in expression vectors. The resulting expression vectors were transiently transfected into human 293 cells and the IgG harvested from the conditioned medium. The potency of the grafted whole IgG molecule was higher than for the scFv antibody (EC 50 between $10^{-8}$M and $10^{-9}$M).

Example 22

Administration of Soluble B7-4Fc Exacerbates Disease in a Murine Model

To determine if modulation of the B7-4/PD-1 pathway has immunoregulatory activity in vivo, the B7-4Fc protein was evaluated in a murine model of experimental autoimmune encephalomyelitis (EAE) that shares many clinical and pathological features with the human disease multiple sclerosis. Female SJL/J mice were immunized with 100 µg of proteolipid protein (PLP) in complete Freund's adjuvant. Ten days later, spleens were harvested, processed to single cell suspensions and then restimulated in vitro with 5 µg of PLP for 96 hours. Cells were washed three times in PBS and then $15 \times 10^6$ cells transferred to naive SJL/J mice by intraperitoneal injection. The adoptive transfer of autoreactive T cells results in acute paralysis of recipient mice which manifests as loss of tail tone with subsequent progression to full hind limb paralysis. This paralytic episode coincides with marked infiltration of activated T cells and macrophages in the CNS. Under most conditions, this is an acute model of disease with spontaneous recovery occurring after a short period of paralysis. For evaluation of B7-4Fc, mice were injected subcutaneously with 200 µg of the protein in 100 µl of sterile saline on days 0, 2, 4, 7 and 11 after cell transfer (n=10). Control mice (n=10) received an equal volume of saline only. All animals were monitored regularly for clinical signs of disease which were scored as follows: 1. Loss of tail tone; 2. Hind limb weakness/partial hind limb paralysis; 3. Complete hind limb paralysis; 4. Hind and forelimb paralysis; 5. Moribund.

Figure 27:
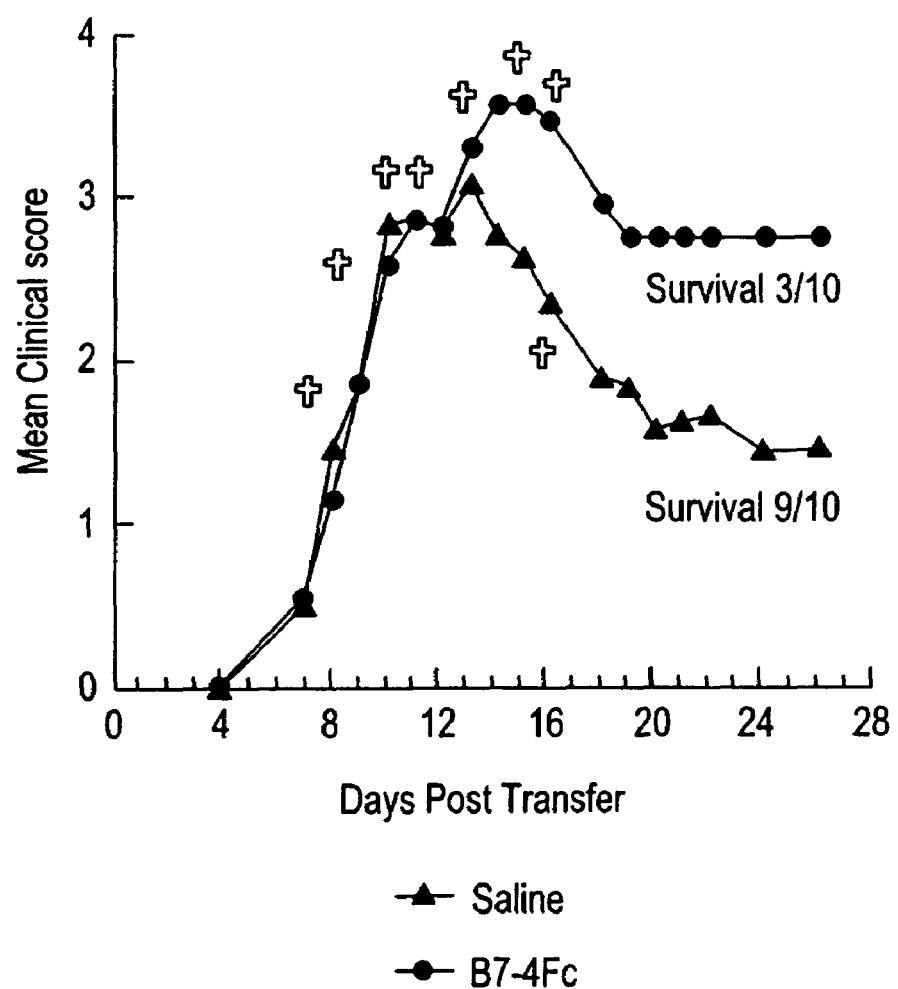
FIG. 27 illustrates the ability of soluble B7-4Fc to exacerbate disease in a murine model of experimental autoimmune encephalomyelitis.

In the experiment shown in FIG. 27, the incidence and onset of clinical disease were similar in both groups. Mice treated with the B7-4Fc however, developed severe disease with the majority of animals rapidly progressing to complete hind and forelimb paralysis (9/10 and 1/10 for B7-4Fc and control mice respectively). Mortality associated with clinical signs of disease was 10% in the control group and 70% in the B7-4Fc treated mice. In addition, recovery from clinical disease was substantially delayed in the B7-4Fc treated mice that did survive despite the fact that treatment was discontinued on day 11.

In conclusion, using an adoptive transfer model of T cell mediated autoimmunity, administration of soluble B7-4Fc exacerbates clinical signs of disease resulting in increased mortality and delayed recovery from paralysis. These findings are consistent with enhanced activation/infiltration of inflammatory cells into the CNS and clearly demonstrate the immunoregulatory potential for the B7-4Fc protein in vivo.

Example 23

Identification of PD-1 Signaling Molecules

This example describes a screening assay for the identification of proteins which are involved in PD-1 signaling pathways. A schematic of the screening assay is shown in FIG. 31A. $1 \times 10^8$ (experiment 1) or $5 \times 10^8$ (experiment 2) Jurkat T cells were treated in the presence and absence of pervanadate. The cells were then lysed in lysis buffer (1% NP-40, 150 mM NaCl, Tris pH 7.6, protease inhibitors, and phosphatase inhibitors). Proteins were then immunoprecipitated with 100 µg biotinylated peptide for 4 hours at 4° C. The following peptides were used for immunoprecipitation: ITIM peptides Y(PO$_4$), F, and Y, and C' (non-ITIM). The sequences of the peptides are shown in FIG. 31B. Streptavidin agarose was added for 30 minutes at 4° C., and samples were then washed 4 times in 1% lysis buffer+0.45 M NaCl, and 2 times with PBS (phosphate buffered saline). Samples were then boiled in SDS-PAGE sample buffer and run on a 4–20% tris-glycine NOVEX gradient gel (reduced). The gel was the silver stained using the Daichi protocol (experiment 1) or the Mann protocol (experiment 2). PD-1 interacting proteins were excised from the gel and analyzed by mass spectrometry analysis.

The following PD-1 interacting proteins were identified:

| Experiment 1 (ITIM peptides): | |
| --- | --- |
| 47 kD Y and pY | −pervanadate |
| 95 kD Y, pY, and F | +pervanadate |
| Experiment 2 (ITIM peptides) | |
| 75 kD Y and pY | −pervanadate |
| 70 kD Y and pY | +pervanadate |
| C-peptide | |
| 22 kD | −pervanadate |
| 46 kD | +pervandaate |

Example 24

Inhibition of ERK1/2 Phosphorylation Through Engagement of the PD-1:B7-4 Signaling Pathway ERK1 and 2 are activated in response to activation of the T cell receptor. This activation is detectable via phosphorylation of the ERK1 and 2 molecules To further elucidate the signaling pathway involved in PD-1 mediated signaling, the effect of PD-1 activation on ERK1/2 activation was investigated.

T cells (otherwise referred to as T cell blasts) were obtained from peripheral blood mononuclear cells which had been stimulated with PHA. The T cells were activated by contact with tosyl-activated beads coated with anti-CD3 (1 µg/$10^7$ beads) and either isotype control Ig (IgG$_{2a}$) or PDL1.Ig fusion protein (4 µg/$10^7$ beads), in the presence of soluble anti-CD28 (5 µg/ml) for either 5, 30, or 90 minutes. Following stimulation, cells and beads were washed once with ice cold PBS, lysed and fractionated by SDS-PAGE. The fractionated cells were then transferred to a nitrocellulose filter, which was then probed with a rabbit polyclonal antibody which specifically recognizes phosphorylated ERK 1 and 2 (Cell Signaling Technologies). The blot was then probed with a secondary antibody, HRP conjugated anti-rabbit IgG (Santa Cruz Biotechnologies). Bound antibody, indicating phosphorylated ERK1 and ERK2, was detected using chemiluminescence. The nitrocellulose filter was then stripped and reprobed with and antibody specific for ERK1 and ERK2, whether or not phosphorylated, to verify that equal amounts of total ERK1 and ERK2 were present in the cell extracts.

Figure 32:
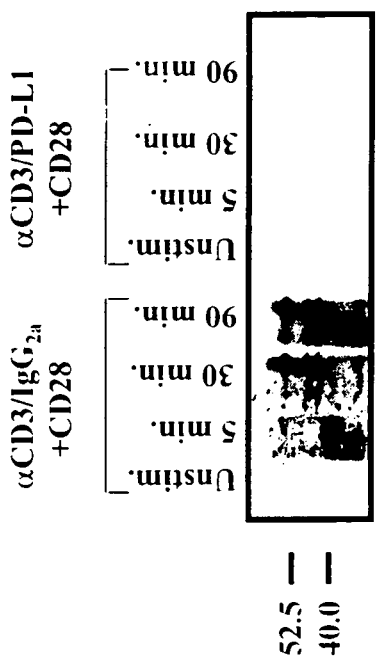
FIG. 32 is a photograph of a Western blot containing fractionated cell extracts of human T cells which were unstimulated or stimulated for 5 min., 30 min, or 90 min, in the presence or absence of a PDL1.Ig fusion protein. The blot was probed with an antibody specific for phosphorylated ERK1 and 2.

The results of probing with anti-phospho ERK specific antibody are shown in FIG. 32. Unstimulated T cells had no detectable phosphorylated ERK1/2. T cells stimulated with anti-CD3 and CD28 had detectable phosphorylated ERK1/2 as little as 5 minutes after stimulation. In contrast, T cells stimulated with anti-CD3 and CD28, and PD-L1 (to activate PD-1), exhibited no detectable increase in ERK1/2 phosphorylation. These results indicate that PD-1 signaling suppresses ERK activation.

Example 25

Inhibition of PKC-θ Phosphorylation Through Engagement of the PD-1:B7-4 Signaling Pathway PKC-θ is known to be activated in response to activation of the T cell receptor. To further elucidate the signaling pathway involved in PD-1 mediated signaling, the effect of activation of PD-1 on PKC-θ activation was investigated.

Human CD28$^+$ T cells, isolated as in Example 24, were activated by contact with tosyl-activated beads coated with anti-CD3 (1 µg/10$^7$ beads) and either isotype control Ig (IgG$_{2a}$) or PDL1.Ig fusion protein (4 µg/10$^7$ beads), in the presence of soluble anti-CD28 (5 µg/ml) for either 5 min, 30 min, or 90 min or 2 hr. Following stimulation, cells and beads were washed once with ice cold PBS, lysed and fractionated by SDS-PAGE. The fractionated cells were then transferred to a nitrocellulose filter, which was then probed with a rabbit polyclonal antibody which specifically recognizes PKC-θ which is phosphorylated at $T_{538}$ (anti-phospho $T_{538}$ antibody, obtained from Cell Signaling Technologies). The nitrocellulose filter was then probed with a secondary antibody, HRP-conjugated anti-murine IgG (Transduction Laboratories). The bound antibody, indicative of phosphorylated PKC-θ, was detected using chemiluminescence. The nitrocellulose filter was then stripped and reprobed with a monoclonal antibody specific for PKC-θ (anti-PKC-θ, E7, obtained from Santa Cruz Biotechnologies to verify equal amounts of PKC-θ were present in the cell extracts.

Figure 33:
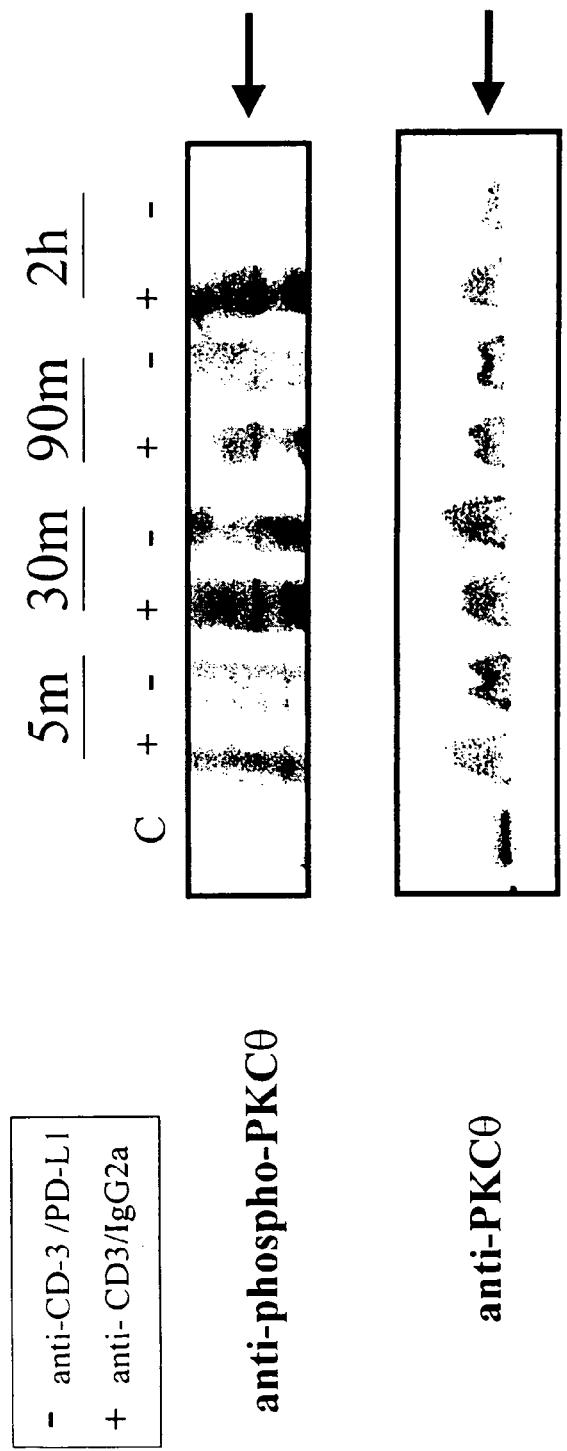
FIG. 33 is a photograph of a Western blot containing fractionated cell extracts of human T cells which were unstimulated, or stimulated for 5 min, 30 min, 90 min. or 2 hr., in the presence (+) or absence (–) of a PDL1.Ig fusion protein. The blot was probed with an antibody specific for phorphorylated PKC-θ to specifically detect phosphorylated PKC-θ (anti-phospho-PKC-θ ). The gel was stripped and then probed with an antibody which recognizes both phosphorylated and unphosphorylated PKC-θ (anti-PKC-θ ).

The results of probing with anti-phospho PKC-θ specific antibody are shown in FIG. 33. Unstimulated T cells had no detectable phosphorylated PKC-θ. T cells stimulated with anti-phospho PKC-θ and CD28 had phosphorylated PKC-θ detectable after 30 minutes of stimulation. This phosphorylation was significantly higher than that of T cells stimulated with anti-CD3 and CD28, and also PD-L1 (to activate PD-1). The fact that similar amounts of total PKC-θ were present in all cell extracts indicates that the increase in phosphorylated PKC-θ does not result from an overall increase in the presence of the PKC-θ molecule, but rather an increase in its phosphorylation by a regulatory kinase, or a decrease in its de-phosphorylation by a regulatory phosphatase. This phosphorylation of the PKC-θ molecule is reported to correlate with an increased activation competent conformation of the PKC-θ enzyme (Liu et al., *Biochem. J.* 361: 255–265 (2002)). The reduced phosphorylation of the PKC-θ molecule in response to activation of PD-1 signaling indicates that PD-1 signaling suppresses PKC-θ activation.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method for screening for compounds which modulate PD-1 signaling comprising:
    a) contacting a T cell activated in the presence of PD-L1 with a test compound;
    b) contacting a T cell activated in the absence of PD-L1 with the test compound; and
    c) determining the ability of the test compound to modulate phosphorylation of ERK 1 or ERK 2;

wherein modulation of phosphorylation of ERK 1 or ERK 2 in the presence of PD-L1 and not in the absence of PD-L1 indicates modulation of PD-1 signaling, thereby identifying a compound which modulates PD-1 signaling.

2. The method of claim 1 wherein the test compound upmodulates PD-1 signaling and thereby downmodulates of ERK 1 or ERK 2.

3. The method of claim 1 wherein the test compound downmodulates PD-1 signaling and thereby upmodulates of ERK 1 or ERK 2.

4. A method for screening for compounds which modulate PD-1 signaling comprising:
    a) contacting a T cell activated in the presence of PD-L1 with a test compound;
    b) contacting a T cell activated in the absence of PD-L1 with the test compound; and
    c) determining the ability of the test compound to modulate phosphorylation of PKC-$\theta$;

wherein modulation of phosphorylation of PKC-$\theta$ in the presence of PD-L1 and not in the absence of PD-L1 indicates modulation of PD-1 signaling, thereby identifying a compound which modulates PD-1 signaling.

5. The method of claim 4 wherein the test compound upmodulates PD-1 signaling and thereby downmodulates phosphorylation of PKC-$\theta$.

6. The method of claim 4 wherein the test compound downmodulates PD-1 signaling and thereby upmodulates phosphorylation of PKC-$\theta$.

* * * * *

UNITED STATES PATENT AND TRADEMARK OFFICE
CERTIFICATE OF CORRECTION

PATENT NO. : 7,105,328 B2  
APPLICATION NO. : 10/115615  
DATED : September 12, 2006  
INVENTOR(S) : Clive Wood et al.

Page 1 of 1

It is certified that error appears in the above-identified patent and that said Letters Patent is hereby corrected as shown below:

In the Specification

At column 1, under Government Funding should read:

--This invention was made with government support under AI039671, AI044690, CA084500 and AI041584 awarded by the National Institutes of Health. The government has certain rights in the invention.--

Signed and Sealed this
Eighth Day of September, 2015

Michelle K. Lee
*Director of the United States Patent and Trademark Office*

SEQUENCE LISTING

```
<160> NUMBER OF SEQ ID NOS: 37

<210> SEQ ID NO 1
<211> LENGTH: 968
<212> TYPE: DNA
<213> ORGANISM: Homo sapiens
<220> FEATURE:
<221> NAME/KEY: CDS
<222> LOCATION: (59)..(793)

<400> SEQUENCE: 1
gcttcccgag gctccgcacc agccgcgctt ctgtccgcct gcagggcatt ccagaaag          58 atg agg ata ttt gct gtc ttt ata ttc atg acc tac tgg cat ttg ctg        106
Met Arg Ile Phe Ala Val Phe Ile Phe Met Thr Tyr Trp His Leu Leu
  1               5                  10                  15 aac gca ttt act gtc acg gtt ccc aag gac cta tat gtg gta gag tat        154
Asn Ala Phe Thr Val Thr Val Pro Lys Asp Leu Tyr Val Val Glu Tyr
             20                  25                  30 ggt agc aat atg aca att gaa tgc aaa ttc cca gta gaa aaa caa tta        202
Gly Ser Asn Met Thr Ile Glu Cys Lys Phe Pro Val Glu Lys Gln Leu
         35                  40                  45 gac ctg gct gca cta att gtc tat tgg gaa atg gag gat aag aac att        250
Asp Leu Ala Ala Leu Ile Val Tyr Trp Glu Met Glu Asp Lys Asn Ile
     50                  55                  60 att caa ttt gtg cat gga gag gaa gac ctg aag gtt cag cat agt agc        298
Ile Gln Phe Val His Gly Glu Glu Asp Leu Lys Val Gln His Ser Ser
 65                  70                  75                  80
```

```
tac aga cag agg gcc cgg ctg ttg aag gac cag ctc tcc ctg gga aat      346
Tyr Arg Gln Arg Ala Arg Leu Leu Lys Asp Gln Leu Ser Leu Gly Asn
                85                  90                  95 gct gca ctt cag atc aca gat gtg aaa ttg cag gat gca ggg gtg tac      394
Ala Ala Leu Gln Ile Thr Asp Val Lys Leu Gln Asp Ala Gly Val Tyr
            100                 105                 110 cgc tgc atg atc agc tat ggt ggt gcc gac tac aag cga att act gtg      442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg      490
Lys Val Asn Ala Pro Tyr Asn Lys Ile Asn Gln Arg Ile Leu Val Val
    130                 135                 140 gat cca gtc acc tct gaa cat gaa ctg aca tgt cag gct gag ggc tac      538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt      586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat      634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac      682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg      730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca      778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt      833
Leu Ser Pro Ser Thr
                245 gaataaatga atgaatgaat aacactatgt ttacaaaata tatcctaatt cctcacctcc    893 attcatccaa accatattgt tacttaataa acattcagca gatatttatg gaataaaaaa    953 aaaaaaaaaa aaaaa                                                     968

<210> SEQ ID NO 2
<211> LENGTH: 245
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
 65                 70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110
```

```
Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245

<210> SEQ ID NO 3
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 3
cgaggctccg caccagccgc gcttctgtcc gcctgcaggg cattccagaa ag atg agg      58
                                                          Met Arg
                                                          1 ata ttt gct gtc ttt ata ttc atg acc tac tgg cat ttg ctg aac gca     106
Ile Phe Ala Val Phe Ile Phe Met Thr Tyr Trp His Leu Leu Asn Ala
    5                   10                  15 ttt act gtc acg gtt ccc aag gac cta tat gtg gta gag tat ggt agc     154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg     202
Asn Met Thr Ile Glu Cys Lys Phe Pro Val Glu Lys Gln Leu Asp Leu
 35                  40                  45                  50 gct gca cta att gtc tat tgg gaa atg gag gat aag aac att att caa     250
Ala Ala Leu Ile Val Tyr Trp Glu Met Glu Asp Lys Asn Ile Ile Gln
                55                  60                  65 ttt gtg cat gga gag gaa gac ctg aag gtt cag cat agt agc tac aga     298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca     346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc     394
Leu Gln Ile Thr Asp Val Lys Leu Gln Asp Ala Gly Val Tyr Arg Cys
    100                 105                 110 atg atc agc tat ggt ggt gcc gac tac aag cga att act gtg aaa gtc     442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca     490
Asn Ala Pro Tyr Asn Lys Ile Asn Gln Arg Ile Leu Val Val Asp Pro
                135                 140                 145
```

```
gtc acc tct gaa cat gaa ctg aca tgt cag gct gag ggc tac ccc aag        538
Val Thr Ser Glu His Glu Leu Thr Cys Gln Ala Glu Gly Tyr Pro Lys
            150                 155                 160 gcc gaa gtc atc tgg aca agc agt gac cat caa gtc ctg agt ggt aag        586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc        634
Thr Thr Thr Thr Asn Ser Lys Arg Glu Glu Lys Leu Phe Asn Val Thr
    180                 185                 190 agc aca ctg aga atc aac aca aca act aat gag att ttc tac tgc act        682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc        730
Phe Arg Arg Leu Asp Pro Glu Glu Asn His Thr Ala Glu Leu Val Ile
            215                 220                 225 cca gaa cta cct ctg gca cat cct cca aat gaa agg act cac ttg gta        778
Pro Glu Leu Pro Leu Ala His Pro Pro Asn Glu Arg Thr His Leu Val
        230                 235                 240 att ctg gga gcc atc tta tta tgc ctt ggt gta gca ctg aca ttc atc        826
Ile Leu Gly Ala Ile Leu Leu Cys Leu Gly Val Ala Leu Thr Phe Ile
    245                 250                 255 ttc cgt tta aga aaa ggg aga atg atg gat gtg aaa aaa tgt ggc atc        874
Phe Arg Leu Arg Lys Gly Arg Met Met Asp Val Lys Lys Cys Gly Ile
260                 265                 270 caa gat aca aac tca aag aag caa agt gat aca cat ttg gag gag acg        922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttaggggt      982 tcatcgggc tgagcgtgac aagaggaagg aatgggcccg tgggatgcag caatgtggg       1042 acttaaaagg cccaagcact gaaaatggaa cctggcgaaa gcagaggagg agaatgaaga     1102
aagatggagt caaacaggga gcctggaggg agaccttgat actttcaaat gcctgagggg    1162
ctcatcgacg cctgtgacag ggagaaagga tacttctgaa caaggagcct ccaagcaaat     1222
catccattgc tcatcctagg aagacgggtt gagaatccct aatttgaggg tcagttcctg     1282
cagaagtgcc ctttgcctcc actcaatgcc tcaatttgtt ttctgcatga ctgagagtct     1342
cagtgttgga acgggacagt attttatgtat gagttttttcc tatttatttt gagtctgtga   1402
ggtcttcttg tcatgtgagt gtggttgtga atgatttctt ttgaagatat attgtagtag    1462
atgttacaat tttgtcgcca aactaaactt gctgcttaat gatttgctca catctagtaa    1522
aacatggagt atttgtaaaa aaaaaaaaa a                                     1553
```

<210> SEQ ID NO 4
<211> LENGTH: 290
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
```

```
                 65                  70                  75                  80
Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 5
<211> LENGTH: 24
<212> TYPE: DNA
<213> ORGANISM: Homo sapiens

<400> SEQUENCE: 5
cagctatggt ggtgccgact acaa                                              24

<210> SEQ ID NO 6
<211> LENGTH: 25
<212> TYPE: DNA
<213> ORGANISM: Homo sapiens

<400> SEQUENCE: 6
aggtgctagg ggacagtgtt agaca                                             25

<210> SEQ ID NO 7
<211> LENGTH:
<212> TYPE:
<213> ORGANISM:

<400> SEQUENCE: 7

000

<210> SEQ ID NO 8
<211> LENGTH:
<212> TYPE:
<213> ORGANISM:
```

<400> SEQUENCE: 8

000

<210> SEQ ID NO 9
<211> LENGTH: 24
<212> TYPE: DNA
<213> ORGANISM: Homo sapiens

<400> SEQUENCE: 9
tcgcttgtag tcggcaccac cata                                            24

<210> SEQ ID NO 10
<211> LENGTH: 864
<212> TYPE: DNA
<213> ORGANISM: Homo sapiens

<400> SEQUENCE: 10
atgcagatcc cacaggcgcc ctggccagtc gtctgggcgg tgctacaact gggctggcgg     60
ccaggatggt tcttagactc cccagacagg ccctggaacc ccccaccctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccacccag ccctcaccc     480 aggtcagccg ccagttcca aaccctggtg gttggtgtcg tgggcggcct gctgggcagc    540
ctggtgctgc tagtctgggt cctggccgtc atctgctccc gggccgcacg agggacaata    600
ggagccaggc gcaccggcca gcccctgaag gaggacccct cagccgtgcc tgtgttctct    660
gtggactatg gggagctgga tttccagtgg cgagagaaga ccccggagcc ccccgtgccc    720
tgtgtccctg agcagacgga gtatgccacc attgtctttc ctagcggaat gggcacctca    780 tccccgccc gcaggggctc agctgacggc cctcggagtg cccagccact gaggcctgag    840
gatggacact gctcttggcc cctc                                           864

<210> SEQ ID NO 11
<211> LENGTH: 921
<212> TYPE: DNA
<213> ORGANISM: Homo sapiens
<220> FEATURE:
<221> NAME/KEY: CDS
<222> LOCATION: (25)..(888)

<400> SEQUENCE: 11
cactctggtg gggctgctcc aggc atg cag atc cca cag gcg ccc tgg cca       51
                             Met Gln Ile Pro Gln Ala Pro Trp Pro
                               1               5 gtc gtc tgg gcg gtg cta caa ctg ggc tgg cgg cca gga tgg ttc tta      99
Val Val Trp Ala Val Leu Gln Leu Gly Trp Arg Pro Gly Trp Phe Leu
 10                  15                  20                  25 gac tcc cca gac agg ccc tgg aac ccc ccc acc ttc tcc cca gcc ctg     147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc     195
Leu Val Val Thr Glu Gly Asp Asn Ala Thr Phe Thr Cys Ser Phe Ser
 45                  50                  55

| | | | | | | | | | | | | | | | | |
|---|---|---|---|---|---|---|---|---|---|---|---|---|---|---|---|---|
| aac | aca | tcg | gag | agc | ttc | gtg | cta | aac | tgg | tac | cgc | atg | agc | ccc | agc | 243 |
| Asn | Thr | Ser | Glu | Ser | Phe | Val | Leu | Asn | Trp | Tyr | Arg | Met | Ser | Pro | Ser | |
| | | | 60 | | | | 65 | | | | | 70 | | | | |
| aac | cag | acg | gac | aag | ctg | gcc | gcc | ttc | ccc | gag | gac | cgc | agc | cag | ccc | 291 |
| Asn | Gln | Thr | Asp | Lys | Leu | Ala | Ala | Phe | Pro | Glu | Asp | Arg | Ser | Gln | Pro | |
| | | 75 | | | | | 80 | | | | | 85 | | | | |
| ggc | cag | gac | tgc | cgc | ttc | cgt | gtc | aca | caa | ctg | ccc | aac | ggg | cgt | gac | 339 |
| Gly | Gln | Asp | Cys | Arg | Phe | Arg | Val | Thr | Gln | Leu | Pro | Asn | Gly | Arg | Asp | |
| | 90 | | | | | 95 | | | | | 100 | | | | 105 | |
| ttc | cac | atg | agc | gtg | gtc | agg | gcc | cgg | cgc | aat | gac | agc | ggc | acc | tac | 387 |
| Phe | His | Met | Ser | Val | Val | Arg | Ala | Arg | Arg | Asn | Asp | Ser | Gly | Thr | Tyr | |
| | | | | 110 | | | | | 115 | | | | | 120 | | |
| ctc | tgt | ggg | gcc | atc | tcc | ctg | gcc | ccc | aag | gcg | cag | atc | aaa | gag | agc | 435 |
| Leu | Cys | Gly | Ala | Ile | Ser | Leu | Ala | Pro | Lys | Ala | Gln | Ile | Lys | Glu | Ser | |
| | | | 125 | | | | | 130 | | | | | 135 | | | |
| ctg | cgg | gca | gag | ctc | agg | gtg | aca | gag | aga | agg | gca | gaa | gtg | ccc | aca | 483 |
| Leu | Arg | Ala | Glu | Leu | Arg | Val | Thr | Glu | Arg | Arg | Ala | Glu | Val | Pro | Thr | |
| | | 140 | | | | | 145 | | | | | 150 | | | | |
| gcc | cac | ccc | agc | ccc | tca | ccc | agg | tca | gcc | ggc | cag | ttc | caa | acc | ctg | 531 |
| Ala | His | Pro | Ser | Pro | Ser | Pro | Arg | Ser | Ala | Gly | Gln | Phe | Gln | Thr | Leu | |
| | 155 | | | | | 160 | | | | | 165 | | | | | |
| gtg | gtt | ggt | gtc | gtg | ggc | ggc | ctg | ctg | ggc | agc | ctg | gtg | ctg | cta | gtc | 579 |
| Val | Val | Gly | Val | Val | Gly | Gly | Leu | Leu | Gly | Ser | Leu | Val | Leu | Leu | Val | |
| 170 | | | | | 175 | | | | | 180 | | | | | 185 | |
| tgg | gtc | ctg | gcc | gtc | atc | tgc | tcc | cgg | gcc | gca | cga | ggg | aca | ata | gga | 627 |
| Trp | Val | Leu | Ala | Val | Ile | Cys | Ser | Arg | Ala | Ala | Arg | Gly | Thr | Ile | Gly | |
| | | | 190 | | | | | 195 | | | | | 200 | | | |
| gcc | agg | cgc | acc | ggc | cag | ccc | ctg | aag | gag | gac | ccc | tca | gcc | gtg | cct | 675 |
| Ala | Arg | Arg | Thr | Gly | Gln | Pro | Leu | Lys | Glu | Asp | Pro | Ser | Ala | Val | Pro | |
| | | 205 | | | | | 210 | | | | | 215 | | | | |
| gtg | ttc | tct | gtg | gac | tat | ggg | gag | ctg | gat | ttc | cag | tgg | cga | gag | aag | 723 |
| Val | Phe | Ser | Val | Asp | Tyr | Gly | Glu | Leu | Asp | Phe | Gln | Trp | Arg | Glu | Lys | |
| | 220 | | | | | 225 | | | | | 230 | | | | | |
| acc | ccg | gag | ccc | ccc | gtg | ccc | tgt | gtc | cct | gag | cag | acg | gag | tat | gcc | 771 |
| Thr | Pro | Glu | Pro | Pro | Val | Pro | Cys | Val | Pro | Glu | Gln | Thr | Glu | Tyr | Ala | |
| | 235 | | | | | 240 | | | | | 245 | | | | | |
| acc | att | gtc | ttt | cct | agc | gga | atg | ggc | acc | tca | tcc | ccc | gcc | cgc | agg | 819 |
| Thr | Ile | Val | Phe | Pro | Ser | Gly | Met | Gly | Thr | Ser | Ser | Pro | Ala | Arg | Arg | |
| 250 | | | | | 255 | | | | | 260 | | | | | 265 | |
| ggc | tca | gct | gac | ggc | cct | cgg | agt | gcc | cag | cca | ctg | agg | cct | gag | gat | 867 |
| Gly | Ser | Ala | Asp | Gly | Pro | Arg | Ser | Ala | Gln | Pro | Leu | Arg | Pro | Glu | Asp | |
| | | | 270 | | | | | 275 | | | | | 280 | | | |
| gga | cac | tgc | tct | tgg | ccc | ctc | tgaccggctt | ccttggccac | cagtgttctg | cag | | | | | | 921 |
| Gly | His | Cys | Ser | Trp | Pro | Leu | | | | | | | | | | |
| | | | 285 | | | | | | | | | | | | | |

<210> SEQ ID NO 12
<211> LENGTH: 288
<212> TYPE: PRT
<213> ORGANISM: Homo sapiens

<400> SEQUENCE: 12

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val

```
                50                   55                   60
Leu Asn Trp Tyr Arg Met Ser Pro Ser Asn Gln Thr Asp Lys Leu Ala
 65                   70                   75                   80

Ala Phe Pro Glu Asp Arg Ser Gln Pro Gly Gln Asp Cys Arg Phe Arg
                85                   90                   95

Val Thr Gln Leu Pro Asn Gly Arg Asp Phe His Met Ser Val Val Arg
               100                  105                  110

Ala Arg Arg Asn Asp Ser Gly Thr Tyr Leu Cys Gly Ala Ile Ser Leu
               115                  120                  125

Ala Pro Lys Ala Gln Ile Lys Glu Ser Leu Arg Ala Glu Leu Arg Val
               130                  135                  140

Thr Glu Arg Arg Ala Glu Val Pro Thr Ala His Pro Ser Pro Ser Pro
145                  150                  155                  160

Arg Ser Ala Gly Gln Phe Gln Thr Leu Val Val Gly Val Val Gly Gly
               165                  170                  175

Leu Leu Gly Ser Leu Val Leu Leu Val Trp Val Leu Ala Val Ile Cys
               180                  185                  190

Ser Arg Ala Ala Arg Gly Thr Ile Gly Ala Arg Arg Thr Gly Gln Pro
               195                  200                  205

Leu Lys Glu Asp Pro Ser Ala Val Pro Val Phe Ser Val Asp Tyr Gly
               210                  215                  220

Glu Leu Asp Phe Gln Trp Arg Glu Lys Thr Pro Glu Pro Pro Val Pro
225                  230                  235                  240

Cys Val Pro Glu Gln Thr Glu Tyr Ala Thr Ile Val Phe Pro Ser Gly
               245                  250                  255

Met Gly Thr Ser Ser Pro Ala Arg Arg Gly Ser Ala Asp Gly Pro Arg
               260                  265                  270

Ser Ala Gln Pro Leu Arg Pro Glu Asp Gly His Cys Ser Trp Pro Leu
               275                  280                  285

<210> SEQ ID NO 13
<211> LENGTH: 20
<212> TYPE: DNA
<213> ORGANISM: Homo sapiens

<400> SEQUENCE: 13
gccgaagtca tctggacaag                                              20

<210> SEQ ID NO 14
<211> LENGTH: 20
<212> TYPE: DNA
<213> ORGANISM: Homo sapiens

<400> SEQUENCE: 14
tctcagtgtg ctggtcacat                                              20

<210> SEQ ID NO 15
<211> LENGTH: 20
<212> TYPE: DNA
<213> ORGANISM: Homo sapiens

<400> SEQUENCE: 15
caccaccacc aattccaaga                                              20

<210> SEQ ID NO 16
<211> LENGTH: 23
<212> TYPE: DNA
<213> ORGANISM: Homo sapiens
```

```
<400> SEQUENCE: 16
acgtgaccaa ggaagtgaaa gaa                                              23

<210> SEQ ID NO 17
<211> LENGTH: 23
<212> TYPE: DNA
<213> ORGANISM: Homo sapiens

<400> SEQUENCE: 17
tgccagctct tcaacagaaa cat                                              23

<210> SEQ ID NO 18
<211> LENGTH: 23
<212> TYPE: DNA
<213> ORGANISM: Homo sapiens

<400> SEQUENCE: 18
tggcaacgct gtcctgtggt cac                                              23

<210> SEQ ID NO 19
<211> LENGTH: 19
<212> TYPE: DNA
<213> ORGANISM: Homo sapiens

<400> SEQUENCE: 19
gggccgcaca agttttgat                                                   19

<210> SEQ ID NO 20
<211> LENGTH: 22
<212> TYPE: DNA
<213> ORGANISM: Homo sapiens

<400> SEQUENCE: 20
gcccttgtcc ttgatctgaa ga                                               22

<210> SEQ ID NO 21
<211> LENGTH: 27
<212> TYPE: DNA
<213> ORGANISM: Homo sapiens

<400> SEQUENCE: 21
cggacagttg gaccctgaga cttcaca                                          27

<210> SEQ ID NO 22
<211> LENGTH: 3593
<212> TYPE: DNA
<213> ORGANISM: Mus musculus
<220> FEATURE:
<221> NAME/KEY: CDS
<222> LOCATION: (17)..(889)

<400> SEQUENCE: 22
agatagttcc caaaac atg agg ata ttt gct ggc att ata ttc aca gcc tgc      52
                Met Arg Ile Phe Ala Gly Ile Ile Phe Thr Ala Cys
                 1               5                  10 tgt cac ttg cta cgg gcg ttt act atc acg gct cca aag gac ttg tac       100
Cys His Leu Leu Arg Ala Phe Thr Ile Thr Ala Pro Lys Asp Leu Tyr
         15                  20                  25 gtg gtg gag tat ggc agc aac gtc acg atg gag tgc aga ttc cct gta       148
Val Val Glu Tyr Gly Ser Asn Val Thr Met Glu Cys Arg Phe Pro Val
 30                  35                  40 gaa cgg gag ctg gac ctg ctt gcg tta gtg gtg tac tgg gaa aag gaa       196
```

```
Glu Arg Glu Leu Asp Leu Leu Ala Leu Val Val Tyr Trp Glu Lys Glu
 45              50                  55                  60 gat gag caa gtg att cag ttt gtg gca gga gag gag gac ctt aag cct      244
Asp Glu Gln Val Ile Gln Phe Val Ala Gly Glu Glu Asp Leu Lys Pro
                 65                  70                  75 cag cac agc aac ttc agg ggg aga gcc tcg ctg cca aag gac cag ctt      292
Gln His Ser Asn Phe Arg Gly Arg Ala Ser Leu Pro Lys Asp Gln Leu
                     80                  85                  90 ttg aag gga aat gct gcc ctt cag atc aca gac gtc aag ctg cag gac      340
Leu Lys Gly Asn Ala Ala Leu Gln Ile Thr Asp Val Lys Leu Gln Asp
             95                 100                 105 gca ggc gtt tac tgc tgc ata atc agc tac ggt ggt gcg gac tac aag      388
Ala Gly Val Tyr Cys Cys Ile Ile Ser Tyr Gly Gly Ala Asp Tyr Lys
        110                 115                 120 cga atc acg ctg aaa gtc aat gcc cca tac cgc aaa atc aac cag aga      436
Arg Ile Thr Leu Lys Val Asn Ala Pro Tyr Arg Lys Ile Asn Gln Arg
125                 130                 135                 140 att tcc gtg gat cca gcc act tct gag cat gaa cta ata tgt cag gcc      484
Ile Ser Val Asp Pro Ala Thr Ser Glu His Glu Leu Ile Cys Gln Ala
                    145                 150                 155 gag ggt tat cca gaa gct gag gta atc tgg aca aac agt gac cac caa      532
Glu Gly Tyr Pro Glu Ala Glu Val Ile Trp Thr Asn Ser Asp His Gln
                160                 165                 170 ccc gtg agt ggg aag aga agt gtc acc act tcc cgg aca gag ggg atg      580
Pro Val Ser Gly Lys Arg Ser Val Thr Thr Ser Arg Thr Glu Gly Met
            175                 180                 185 ctt ctc aat gtg acc agc agt ctg agg gtc aac gcc aca gcg aat gat      628
Leu Leu Asn Val Thr Ser Ser Leu Arg Val Asn Ala Thr Ala Asn Asp
        190                 195                 200 gtt ttc tac tgt acg ttt tgg aga tca cag cca ggg caa aac cac aca      676
Val Phe Tyr Cys Thr Phe Trp Arg Ser Gln Pro Gly Gln Asn His Thr
205                 210                 215                 220 gcg gag ctg atc atc cca gaa ctg cct gca aca cat cct cca cag aac      724
Ala Glu Leu Ile Ile Pro Glu Leu Pro Ala Thr His Pro Pro Gln Asn
                    225                 230                 235 agg act cac tgg gtg ctt ctg gga tcc atc ctg ttg ttc ctc att gta      772
Arg Thr His Trp Val Leu Leu Gly Ser Ile Leu Leu Phe Leu Ile Val
                240                 245                 250 gtg tcc acg gtc ctc ctc ttc ttg aga aaa caa gtg aga atg cta gat      820
Val Ser Thr Val Leu Leu Phe Leu Arg Lys Gln Val Arg Met Leu Asp
            255                 260                 265 gtg gag aaa tgt ggc gtt gaa gat aca agc tca aaa aac cga aat gat      868
Val Glu Lys Cys Gly Val Glu Asp Thr Ser Ser Lys Asn Arg Asn Asp
        270                 275                 280 aca caa ttc gag gag acg taa gcagtgttga accctctgat cgtcgattgg         919
Thr Gln Phe Glu Glu Thr
285                 290 cagcttgtgg tctgtgaaag aaagggccca tgggacatga gtccaaagac tcaagatgga    979
acctgaggga gagaaccaag aaagtgttgg gagaggagcc tggaacaacg acatttttt    1039 ccagggagac actgctaagc aagttgccca tcagtcgtct tgggaaatgg attgagggtt   1099
cctggcttag cagctggtcc ttgcacagtg accttttcct ctgctcagtg ccgggatgag   1159
agatggagtc atgagtgttg aagaataagt gccttctatt tattttgagt ctgtgtgttc   1219
tcactttggg catgtaatta tgactggtga attctgacga catgatagat cttaagatgt   1279
agtcaccaaa ctcaactgct gcttagcatc ctccgtaact actgatacaa gcagggaaca   1339
cagaggtcac ctgcttggtt tgacaggctc ttgctgtctg actcaaataa tctttatttt   1399
```

-continued

```
tcagtcctca aggctcttcg atagcagttg ttctgtatca gccttatagg tgtcaggtat    1459
agcactcaac atctcatctc attacaatag caaccctcat caccatagca acagctaacc    1519
tctgttatcc tcacttcata gccaggaagc tgagcgacta agtcacttgc ccacagagta    1579
tcagctctca gatttctgtt cttcagccac tgtcctttca ggatagaatt tgtcgttaag    1639
aaattaattt aaaaactgat tattgagtag cattgtatat caatcacaac atgccttgtg    1699
cactgtgctg gcctctgagc ataaagatgt acgccggagt accggtcgga catgtttatg    1759
tgtgttaaat actcagagaa atgttcatta acaaggagct tgcattttag agacactgga    1819
aagtaactcc agttcattgt ctagcattac atttaccctca tttgctatcc ttgccataca    1879
gtctcttgtt ctccatgaag tgtcatgaat cttgttgaat agttctttta tttttttaaat   1939
gtttctattt aaatgatatt gacatctgag gcgatagctc agttggtaaa accctttcct    1999
cacaagtgtg aaaccctgag tcttatccct agaacccaca taaaaaacag ttgcgtatgt    2059
ttgtgcatgc ttttgatccc agcactaggg aggcagaggc aggcagatcc tgagctctca    2119
ttgaccaccc agcctagcct acatggttag ctccaggcct acaggagctg gcagagcctg    2179
aaaaacgatg cctagacaca cacacacaca cacacacaca cacacacaca cacacacacc    2239
atgtactcat agacctaagt gcaccctcct acacatgcac acacatacaa ttcaaacaca    2299
aatcaacagg gaattgtctc agaatggtcc ccaagacaaa aagaagaaa acaccaaac     2359
cagctctatt ccctcagcct atcctctcta ctccttccta gaagcaacta ctattgtttt    2419
tgtatataaa tttacccaac gacagttaat atgtagaata tatattaaag tgtctgtcaa    2479
tatatattat ctcttctttt ctttcttcct ttctttcttt ctttctttct ttctttcttt    2539
ctttctttct ttctttcttt cttccttcct tccttccttc cttccttcct tccttccttt    2599
ctttctttct ttcttttttt ctgtctatct gtacctaaat ggttgctcac tatgcatttt    2659
ctgtgctctt cgccctttt atttaatgta tggatattta tgctgcttcc agaatggatc      2719
taaagctctt tgtttctagg ttttctcccc catccttcta ggcatctctc acactgtcta    2779
ggccagacac catgtctgct gcctgaatct gtagacacca tttataaagc acgtactcac    2839
cgagtttgta tttggcttgt tctgtgtctg attaaaggga gaccatgagt ccccagggta    2899
cactgagtta ccccagtacc aagggggagc cttgtttgtg tctccatggc agaagcaggc    2959
ctggagccat tttggtttct tccttgactt ctctcaaaca cagacgcctc acttgctcat    3019
tacaggttct cctttgggaa tgtcagcatt gctccttgac tgctggctgc cctggaagga    3079
gcccattagc tctgtgtgag cccttgacag ctactgcctc tccttaccac aggggcctct    3139
aagatactgt tacctagagg tcttgaggat ctgtgttctc tgggggagg aaaggaggag     3199
gaacccagaa ctttcttaca gttttccttg ttctgtcaca tgtcaagact gaaggaacag    3259
gctgggctac gtagtgagat cctgtctcaa aggaaagacg agcatagccg aaccccggt     3319
ggaacccct ctgttacctg ttcacacaag cttattgatg agtctcatgt taatgtcttg     3379
tttgtatgaa gtttaagaaa atatcgggtt gggcaacaca ttctatttat tcattttatt    3439
tgaaatctta atgccatctc atggtgttgg attggtgtgg cactttattc ttttgtgttg    3499
tgtataacca taaattttat tttgcatcag attgtcaatg tattgcatta atttaataaa    3559
tattttattt tattaaaaaa aaaaaaaaaa aaaa                                3593
```

<210> SEQ ID NO 23
<211> LENGTH: 290
<212> TYPE: PRT
<213> ORGANISM: Mus musculus

```
<400> SEQUENCE: 23

Met Arg Ile Phe Ala Gly Ile Ile Phe Thr Ala Cys Cys His Leu Leu
 1               5                  10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 24
<211> LENGTH: 120
<212> TYPE: PRT
<213> ORGANISM: Homo sapiens

<400> SEQUENCE: 24

Leu Val Val Gly Val Val Gly Gly Leu Leu Gly Ser Leu Val Leu Leu
 1               5                  10                  15

Val Trp Val Leu Ala Val Ile Cys Ser Arg Ala Ala Arg Gly Thr Ile
                20                  25                  30

Gly Ala Arg Arg Thr Gly Gln Pro Leu Lys Glu Asp Pro Ser Ala Val
            35                  40                  45

Pro Val Phe Ser Val Asp Tyr Gly Glu Leu Asp Phe Gln Trp Arg Glu
        50                  55                  60
```

```
Lys Thr Pro Glu Pro Val Pro Cys Val Pro Glu Gln Thr Glu Tyr
65                  70                  75                  80

Ala Thr Ile Val Phe Pro Ser Gly Met Gly Thr Ser Pro Ala Arg
                85                  90                  95

Arg Gly Ser Ala Asp Gly Pro Arg Ser Ala Gln Pro Leu Arg Pro Glu
            100                 105                 110

Asp Gly His Cys Ser Trp Pro Leu
        115                 120

<210> SEQ ID NO 25
<211> LENGTH: 120
<212> TYPE: PRT
<213> ORGANISM: Mus musculus

<400> SEQUENCE: 25

Met Val Ile Gly Ile Met Ser Ala Leu Val Gly Ile Pro Val Leu Leu
1               5                   10                  15

Leu Leu Ala Trp Ala Leu Ala Val Phe Cys Ser Thr Ser Met Ser Glu
            20                  25                  30

Ala Arg Gly Ala Gly Ser Lys Asp Asp Thr Leu Lys Glu Glu Pro Ser
        35                  40                  45

Ala Ala Pro Val Pro Ser Val Ala Tyr Glu Glu Leu Asp Phe Gln Gly
    50                  55                  60

Arg Glu Lys Thr Pro Glu Leu Pro Thr Ala Cys Val His Thr Glu Tyr
65                  70                  75                  80

Ala Thr Ile Val Phe Thr Glu Gly Leu Gly Ala Ser Ala Met Gly Arg
                85                  90                  95

Arg Gly Ser Ala Asp Gly Leu Gln Gly Pro Arg Pro Arg His Glu
            100                 105                 110

Asp Gly His Cys Ser Trp Pro Leu
        115                 120

<210> SEQ ID NO 26
<211> LENGTH: 23
<212> TYPE: PRT
<213> ORGANISM: Artificial sequence
<220> FEATURE:
<223> OTHER INFORMATION: peptides identified in screening assay

<400> SEQUENCE: 26

Lys Glu Asp Pro Ser Ala Val Pro Val Phe Ser Val Asp Tyr Gly Glu
1               5                   10                  15

Leu Asp Phe Gln Trp Arg Glu
            20

<210> SEQ ID NO 27
<211> LENGTH: 23
<212> TYPE: PRT
<213> ORGANISM: Artificial sequence
<220> FEATURE:
<223> OTHER INFORMATION: peptides identified in screening assay

<400> SEQUENCE: 27

Lys Glu Asp Pro Ser Ala Val Pro Val Phe Ser Val Asp Phe Gly Glu
1               5                   10                  15

Leu Asp Phe Gln Trp Arg Glu
            20

<210> SEQ ID NO 28
```

```
<211> LENGTH: 23
<212> TYPE: PRT
<213> ORGANISM: Artificial sequence
<220> FEATURE:
<223> OTHER INFORMATION: peptides identified in screening assay

<400> SEQUENCE: 28

Lys Glu Asp Pro Ser Ala Val Pro Val Phe Ser Val Asp Tyr Gly Glu
 1               5                  10                  15

Leu Asp Phe Gln Trp Arg Glu
            20

<210> SEQ ID NO 29
<211> LENGTH: 29
<212> TYPE: PRT
<213> ORGANISM: Artificial sequence
<220> FEATURE:
<223> OTHER INFORMATION: peptides identified in screening assay

<400> SEQUENCE: 29

Lys Thr Pro Glu Pro Pro Val Pro Ser Val Pro Glu Gln Thr Glu Tyr
 1               5                  10                  15

Ala Thr Ile Val Phe Pro Ser Gly Met Gly Thr Ser Ser
            20                  25

<210> SEQ ID NO 30
<211> LENGTH: 29
<212> TYPE: PRT
<213> ORGANISM: Artificial sequence
<220> FEATURE:
<223> OTHER INFORMATION: peptides identified in screening assay

<400> SEQUENCE: 30

Lys Thr Pro Glu Pro Pro Val Pro Ser Val Pro Glu Gln Thr Glu Phe
 1               5                  10                  15

Ala Thr Ile Val Phe Pro Ser Gly Met Gly Thr Ser Ser
            20                  25

<210> SEQ ID NO 31
<211> LENGTH: 29
<212> TYPE: PRT
<213> ORGANISM: Artificial sequence
<220> FEATURE:
<223> OTHER INFORMATION: peptides identified in screening assay

<400> SEQUENCE: 31

Lys Thr Pro Glu Pro Pro Val Pro Ser Val Pro Glu Gln Thr Glu Tyr
 1               5                  10                  15

Ala Thr Ile Val Phe Pro Ser Gly Met Gly Thr Ser Ser
            20                  25

<210> SEQ ID NO 32
<211> LENGTH: 24
<212> TYPE: PRT
<213> ORGANISM: Artificial sequence
<220> FEATURE:
<223> OTHER INFORMATION: peptides identified in screening assay

<400> SEQUENCE: 32

Arg Gly Thr Ile Gly Ala Arg Arg Thr Gly Gln Pro Leu Lys Glu Asp
 1               5                  10                  15

Pro Ser Ala Val Pro Val Phe Ser
            20
```

```
<210> SEQ ID NO 33
<211> LENGTH: 24
<212> TYPE: PRT
<213> ORGANISM: Artificial sequence
<220> FEATURE:
<223> OTHER INFORMATION: peptides identified in screening assay

<400> SEQUENCE: 33

Arg Gly Thr Ile Gly Ala Arg Arg Thr Gly Gln Pro Leu Asp Glu Asp
 1               5                  10                  15

Pro Ser Ala Val Pro Val Phe Ser
            20

<210> SEQ ID NO 34
<211> LENGTH: 19
<212> TYPE: PRT
<213> ORGANISM: Artificial sequence
<220> FEATURE:
<223> OTHER INFORMATION: peptides identified in screening assay

<400> SEQUENCE: 34

Asp Phe Gln Trp Arg Glu Lys Thr Pro Glu Pro Pro Val Pro Cys Val
 1               5                  10                  15

Pro Glu Gln

<210> SEQ ID NO 35
<211> LENGTH: 19
<212> TYPE: PRT
<213> ORGANISM: Artificial sequence
<220> FEATURE:
<223> OTHER INFORMATION: peptides identified in screening assay

<400> SEQUENCE: 35

Asp Phe Gln Trp Arg Glu Asp Thr Pro Glu Pro Pro Val Pro Cys Val
 1               5                  10                  15

Pro Glu Gln

<210> SEQ ID NO 36
<211> LENGTH: 23
<212> TYPE: PRT
<213> ORGANISM: Artificial sequence
<220> FEATURE:
<223> OTHER INFORMATION: peptides identified in screening assay

<400> SEQUENCE: 36

Val Phe Pro Ser Gly Met Gly Thr Ser Ser Pro Ala Arg Arg Gly Ser
 1               5                  10                  15

Ala Asp Gly Pro Arg Ser Ala
            20

<210> SEQ ID NO 37
<211> LENGTH: 26
<212> TYPE: PRT
<213> ORGANISM: Artificial sequence
<220> FEATURE:
<223> OTHER INFORMATION: peptides identified in screening assay

<400> SEQUENCE: 37

Ala Arg Arg Gly Ser Ala Asp Gly Pro Arg Ser Ala Gln Pro Leu Arg
 1               5                  10                  15

Pro Glu Asp Gly His Cys Ser Trp Pro Leu
            20                  25
```